(12) United States Patent
Caroff et al.

(10) Patent No.: US 8,664,203 B2
(45) Date of Patent: Mar. 4, 2014

(54) THIAZOLE DERIVATIVES AND THEIR USE AS P2Y12 RECEPTOR ANTAGONISTS

(75) Inventors: Eva Caroff, Allschwil (CH); Kurt Hilpert, Allschwil (CH); Francis Hubler, Allschwil (CH); David Lehmann, Allschwil (CH); Emmanuel Meyer, Allschwil (CH); Dorte Renneberg, Allschwil (CH)

(73) Assignee: Actelion Pharmaceuticals Ltd., Allschwil (CH)

( * ) Notice: Subject to any disclaimer, the term of this patent is extended or adjusted under 35 U.S.C. 154(b) by 191 days.

(21) Appl. No.: 13/265,493

(22) PCT Filed: Apr. 21, 2010

(86) PCT No.: PCT/IB2010/051742
§ 371 (c)(1),
(2), (4) Date: Oct. 20, 2011

(87) PCT Pub. No.: WO2010/122504
PCT Pub. Date: Oct. 28, 2010

(65) Prior Publication Data
US 2012/0053149 A1    Mar. 1, 2012
US 2013/0281406 A2    Oct. 24, 2013

(30) Foreign Application Priority Data

Apr. 22, 2009   (WO) .................. PCT/IB2009/051647

(51) Int. Cl.
A61K 31/496   (2006.01)
A61K 31/675   (2006.01)
C07D 417/04   (2006.01)
C07F 9/38   (2006.01)

(52) U.S. Cl.
USPC ............... 514/85; 514/235.8; 514/254.03; 544/337; 544/121; 544/369

(58) Field of Classification Search
None
See application file for complete search history.

(56) References Cited

U.S. PATENT DOCUMENTS

| | | | |
|---|---|---|---|
| 8,044,055 | B2 | 10/2011 | Caroff et al. |
| 8,048,881 | B2 | 11/2011 | Caroff et al. |
| 8,058,263 | B2 | 11/2011 | Caroff et al. |
| 8,067,419 | B2 | 11/2011 | Binkert et al. |
| 8,093,250 | B2 | 1/2012 | Caroff et al. |
| 8,466,156 | B2 | 6/2013 | Caroff et al. |
| 2010/0261678 | A1 | 10/2010 | Caroff et al. |
| 2011/0028484 | A1 | 2/2011 | Caroff et al. |

FOREIGN PATENT DOCUMENTS

| | | |
|---|---|---|
| WO | WO 02/098856 | 12/2002 |
| WO | WO 2004/052366 | 6/2004 |
| WO | WO 2006/114774 | 11/2006 |
| WO | WO 2008/044217 | 4/2008 |
| WO | WO 2008/050301 | 5/2008 |
| WO | WO 2008/128647 | 10/2008 |
| WO | WO 2009/069100 | 6/2009 |
| WO | WO 2009/080226 | 7/2009 |
| WO | WO 2009/080227 | 7/2009 |
| WO | WO 2009/125365 | 10/2009 |
| WO | WO 2009/125366 | 10/2009 |
| WO | WO 2010/116328 | 10/2010 |

OTHER PUBLICATIONS

Norgard, Expert Opin.Invest.Drugs, vol. 18(8), pp. 1219-1230 (2009).*
CAPRIE Steering Committee, The Lancet vol. 348, pp. 1329-1339 (1996).*
Gould, P.L., "Salt Selection for Basic Drugs", International Journal of Pharmaceutics, 1986, vol. 33, 201-217.
Parlow, J. J., et al., "Piperazinyl-glutamate-pyrimidines as Potent Orally Bioavailable P2Y$_{12}$ Antagonists for Inhibition of Platelet Aggregation", Bioorganic & Medicinal Chemistry Letters, vol. 19, pp. 4657-4663, (2009).
Parlow, J. J., et al., "Piperazinyl-glutamate-pyrimidines as Potent P2Y$_{12}$ Antagonists for Inhibition of Platelet Aggregation", Bioorganic & Medicinal Chemistry Letters, vol. 19, pp. 6148-6156, (2009).
Remington, The Science and Practice of Pharmacy, 21$^{st}$ Edition (2005), Part 5, "Pharmaceutical Manufacturing", [published by Lippincott Williams & Wilkins] (Table of Contents).
Parlow, J.J. et al., "Piperazinyl glutamate pyridines as potent orally bioavailable P2Y$_{12}$ antagonists for inhibition of platelet aggregation," *J. Med. Chem.*, 2010, 53, 2010-2037.

* cited by examiner

*Primary Examiner* — Emily Bernhardt
(74) *Attorney, Agent, or Firm* — Hoxie & Associates LLC

(57) ABSTRACT

The present invention relates to thiazole derivatives of formula I and their use as P2Y$_{12}$ receptor antagonists in the treatment and/or prevention of peripheral vascular, of visceral-, hepatic- and renal-vascular, of cardiovascular and of cerebrovascular diseases or conditions associated with platelet aggregation, including thrombosis in humans and other mammals.

formula I

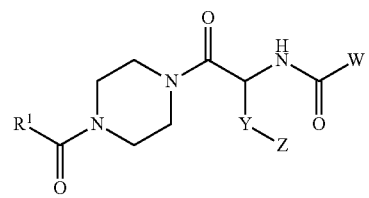

14 Claims, No Drawings

THIAZOLE DERIVATIVES AND THEIR USE AS P2Y12 RECEPTOR ANTAGONISTS

CROSS REFERENCE TO RELATED APPLICATIONS

This application is a United States Application under 35 U.S.C. 371 claiming benefit of PCT Application No. PCT/IB2010/051742, filed on Apr. 21, 2010, which claims the benefit of PCT Application No. PCT/IB2009/051647, filed on Apr. 22, 2009, the contents of each of which are incorporated herein by reference in their entirety.

FIELD OF THE INVENTION

The present invention relates to certain thiazole derivatives and their use as $P2Y_{12}$ receptor antagonists in the treatment and/or prevention of peripheral vascular, of visceral-, hepatic- and renal-vascular, of cardiovascular and of cerebrovascular diseases or conditions associated with platelet aggregation, including thrombosis in humans and other mammals.

BACKGROUND OF THE INVENTION

Haemostasis is referred to as the natural balance of maintaining the fluidity of the blood in the vascular system and preventing excessive blood loss subsequent to blood vessel injury by rapid formation of a solid blood clot. After vascular damage, contraction of the vessels and platelet adhesion occur immediately followed by aggregation of the platelets, activation of the coagulation cascade and finally also of the fibrinolytic system. Haemostatic abnormalities can lead to excessive bleeding or thrombosis, both life-threatening situations.

A series of antiplatelet agents have been developed over the past several years based on different mechanisms of action. The most widely used agent in antiplatelet therapy is aspirin, which irreversibly inhibits cyclooxygenase-1 and thereby affecting the thromboxane pathway. Although not optimally efficacious, treatment with aspirin remains the standard therapy against which new therapeutics are compared and judged.

Other drugs like the phosphodiesterase inhibitors dipyridamole and cilostazol, as well as the vitamin K antagonists (warfarin), are marketed but do not show all desirable features for such drugs. Three intravenously applicable, potent GPIIb/IIIa receptor antagonists (abciximab, eptifibatide, and tirofiban) blocking platelet aggregation are available on the market. Besides, some orally active GPIIb/IIIa antagonists (e.g. sibrafiban, xemilofiban or orbofiban) have not been successful in clinical development so far.

Adenosine 5'-diphosphate (ADP) is a key mediator in platelet activation and aggregation interfering with two platelet ADP receptors $P2Y_1$ and $P2Y_{12}$.

Antagonists of the platelet ADP receptor have been identified and display inhibition of platelet aggregation and antithrombotic activity. The most effective antagonists known so far are the thienopyridines ticlopidine, clopidogrel and CS-747, which have been used clinically as antithrombotic agents. It could be shown that these drugs, via their reactive metabolites, irreversibly block the ADP receptor subtype $P2Y_{12}$.

Some $P2Y_{12}$ antagonists like AR-C69931MX (Cangrelor) or AZD6140 have reached clinical studies. These inhibitors are selective platelet ADP receptor antagonists, which inhibit ADP-dependent platelet aggregation, and are effective in vivo.

Piperazino-carbonylmethylaminocarbonyl-naphtyl or -quinolyl derivatives have been described as ADP receptor antagonists in WO 02/098856 and WO 04/052366.

WO 06/114774 describes 2-phenyl-4-(carbonylmethylaminocarbonyl)-pyrimidine derivatives as $P2Y_{12}$ receptor antagonists. 2-Aminocarbonyl-pyridine derivatives are described in WO 08/044,217.

DESCRIPTION OF THE INVENTION

Various embodiments of the invention are presented hereafter:

1) The present invention firstly relates to the compounds of formula I

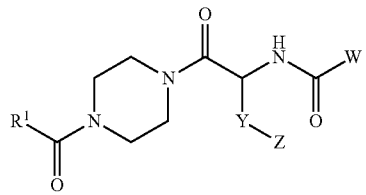

formula I wherein
$R^1$ represents $(C_1-C_6)$alkoxy;
Y represents a bond and Z represents hydrogen; or
Y represents $(C_1-C_3)$alkandiyl and Z represents hydrogen, hydroxy, —COOH, —COOR$^5$, —P(O)(OH)$_2$, —P(O)(OR$^6$)$_2$, —P(O)(NHR$^7$)$_2$ or phenyl, wherein the phenyl is substituted with —P(O)(OH)$_2$ or —P(O)(OR$^8$)$_2$;
W represents a group selected from

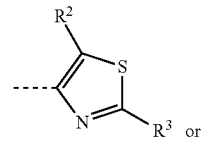

(G1)

or

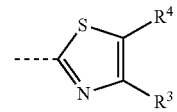

(G2)

$R^2$ represents hydrogen; halogen; $(C_1-C_4)$alkyl which is monosubstituted with $(C_1-C_4)$alkoxy, —COOH or —COOR$^9$; $(C_2-C_4)$alkenyl which is monosubstituted with $(C_1-C_4)$alkoxy, —COOH or —COOR$^9$; phenyl which is unsubstituted or monosubstituted with halogen; $(C_1-C_4)$alkyl-amino, wherein the alkyl-group is monosubstituted with hydroxy, $(C_1-C_4)$alkoxy, —COOH or —COOR$^9$; di-$(C_1-C_4)$alkyl-amino; heterocyclyl which is unsubstituted or monosubstituted with $(C_1-C_4)$alkyl or $(C_1-C_4)$alkoxy; or 2-methoxymethyl-cycloprop-1-yl (notably (1S,2S)-2-methoxymethyl-cycloprop-1-yl);
$R^3$ represents aryl which is unsubstituted or mono- or di-substituted, wherein the substituents are independently selected from the group consisting of halogen, $(C_1-C_4)$alkyl, $(C_1-C_4)$alkoxy and phenoxy;
$R^4$ represents halogen; $(C_1-C_4)$alkyl which is monosubstituted with $(C_1-C_4)$alkoxy, —COOH, or —COOR$^9$; $(C_2-C_4)$alkenyl which is monosubstituted with $(C_1-C_4)$alkoxy or —COOR$^9$; phenyl; or di-$(C_1-C_6)$alkyl-amino;
$R^5$ represents $(C_1-C_4)$alkyl;
$R^6$ represents $(C_1-C_4)$alkyl, $(C_1-C_4)$alkyl-C(O)—OCH$_2$— or $(C_1-C_4)$alkoxy-C(O)—OCH$_2$—;
$R^7$ represents $(C_1-C_4)$alkoxy-C(O)—$(C_1-C_4)$alkyl-;
$R^8$ represents $(C_1-C_4)$alkyl;
$R^9$ represents $(C_1-C_4)$alkyl;
and to the salts (in particular pharmaceutically acceptable salts) of such compounds.

The compounds of formula I may contain one or more stereogenic or asymmetric centers, such as one or more asymmetric carbon atoms. The compounds of formula I may thus be present as mixtures of stereoisomers or preferably as pure stereoisomers. Mixtures of stereoisomers may be separated in a manner known to a person skilled in the art. Substituents at a double bond may be present in the (Z)- or (E)-configuration (preferably in (E)-configuration) unless indicated otherwise.

The compounds of formula I are $P2Y_{12}$ receptor antagonists. Accordingly, they are useful in therapy (including combination therapy), where they can be widely used as inhibitors of platelet activation, aggregation and degranulation, as promoters of platelet disaggregation or as anti-thrombotic agents.

The following paragraphs provide definitions of the various chemical moieties for the compounds according to the invention. Said definitions are intended to apply uniformly throughout the specification and claims unless an otherwise expressly set out definition provides a broader or narrower definition.

The term "halogen" refers to fluorine, chlorine, bromine or iodine.

In case $R^2$ represents halogen, the term preferably refers to chlorine or bromine and more preferably to chlorine.

In case $R^4$ represents halogen, the term preferably refers to chlorine or bromine and more preferably to bromine In case the halogen is attached to a phenyl or to an aryl group the term preferably refers to fluorine, chlorine or bromine and more preferably to fluorine.

The term "alkyl", used alone or in combination, refers to a saturated straight or branched chain alkyl group containing one to six carbon atoms. The term "$(C_x$—$C_y)$alkyl" (x and y each being an integer) refers to an alkyl group as defined before containing x to y carbon atoms. For example a $(C_1$-$C_6)$alkyl group contains from one to six carbon atoms. Representative examples of alkyl groups include methyl, ethyl, n-propyl, iso-propyl, n-butyl, iso-butyl, sec-butyl, tert-butyl, n-pentyl, 1-methyl-butyl, 2-methyl-butyl, 3-methyl-butyl, 1,1-dimethyl-propyl, 1,2-dimethyl-propyl, 2,2-dimethyl-propyl, 1-ethyl-propyl, n-hexyl, 1-methyl-pentyl, 2-methyl-pentyl, 3-methyl-pentyl, 4-methyl-pentyl, 1-ethyl-butyl, 2-ethyl-butyl, 1,1-dimethyl-butyl, 1,2-dimethyl-butyl, 2,2-dimethyl-butyl, 1,3-dimethyl-butyl, 2,3-dimethyl-butyl, 3,3-dimethyl-butyl, 1,1,2-trimethyl-propyl, 1,2,2-trimethyl-propyl, 1-ethyl-1-methyl-propyl and 1-ethyl-2-methyl-propyl. The alkyl group may be unsubstituted or substituted as explicitly defined.

In case $R^2$ represents "$(C_1$-$C_4)$alkyl" the term refers to an $(C_1$-$C_4)$alkyl group as defined above. Preferred examples are methyl, ethyl and n-propyl. More preferred are ethyl and n-propyl. The above-mentioned $(C_1$-$C_4)$alkyl groups are monosubstituted with $(C_1$-$C_4)$ alkoxy, —COOH or —COOR$^9$ (and preferably with methoxy and —COOH).

In case $R^2$ represents "heterocyclyl which is monosubstituted with $(C_1$-$C_4)$alkyl" the term "$(C_1$-$C_4)$alkyl" refers to an $(C_1$-$C_4)$alkyl group as defined above. Preferred examples are methyl and ethyl. More preferred is methyl.

In case $R^3$ represents "aryl which is substituted with $(C_1$-$C_4)$alkyl" the term "$(C_1$-$C_4)$alkyl" refers to an $(C_1$-$C_4)$ alkyl group as defined above. Preferred examples are methyl and ethyl. More preferred is methyl.

In case $R^4$ represents "$(C_1$-$C_4)$alkyl" the term refers to an $(C_1$-$C_4)$alkyl group as defined above. Preferred examples are methyl, ethyl and n-propyl. More preferred are ethyl and n-propyl. The above-mentioned $(C_1$-$C_4)$alkyl groups are monosubstituted with $(C_1$-$C_4)$ alkoxy, —COOH or —COOR$^9$ (and preferably with methoxy and —COOH).

In case $R^5$ represents "$(C_1$-$C_4)$alkyl" the term refers to an $(C_1$-$C_4)$alkyl group as defined above. Preferred examples are methyl, ethyl, n-propyl, iso-propyl and tert-butyl. More preferred is tert-butyl.

In case $R^6$ represents "$(C_1$-$C_4)$alkyl" the term refers to an $(C_1$-$C_4)$alkyl group as defined above. Preferred examples are methyl and ethyl. More preferred is ethyl.

In case $R^6$ represents "$(C_1$-$C_4)$alkyl-C(O)—OCH$_2$—" the term $(C_1$-$C_4)$alkyl refers to an $(C_1$-$C_4)$alkyl group as defined above. Preferred examples are methyl and ethyl. More preferred is methyl.

In case $R^8$ represents "$(C_1$-$C_4)$alkyl" the term refers to an $(C_1$-$C_4)$alkyl group as defined above. Preferred examples are methyl and ethyl. More preferred is ethyl.

In case $R^9$ represents "$(C_1$-$C_4)$alkyl" the term refers to an $(C_1$-$C_4)$alkyl group as defined above. Preferred examples are methyl and ethyl.

The term "$(C_1$-$C_3)$alkandiyl" as used in Y refers to a carbon chain containing from one to three carbon atoms, which is attached to the substituent Z and to the α-carbon atom of the amino acid part of the rest of the molecule as depicted in formula I. The respective two residues may be attached to the same or to different carbon atoms of the alkandiyl group. Preferred examples of $(C_1$-$C_3)$alkandiyl groups are methandiyl, ethan-1,2-diyl and propan-2,2-diyl. More preferred are methandiyl and ethan-1,2-diyl. Most preferred is methandiyl.

The term "alkenyl", used alone or in combination, refers to a straight or branched chain alkenyl group containing two to four carbon atoms. The term "$(C_x$—$C_y)$alkenyl" (x and y each being an integer) refers to an alkenyl group as defined before containing x to y carbon atoms. For example a $(C_2$-$C_4)$alkenyl group contains from two to four carbon atoms. Representative examples of alkenyl groups include vinyl, allyl, 2-methyl-propenyl and butenyl. The alkenyl group may be unsubstituted or substituted as explicitly defined.

In case $R^2$ represents "$(C_2$-$C_4)$alkenyl" the term refers to an $(C_2$-$C_4)$alkenyl group as defined above. Preferred examples are vinyl and allyl. The above-mentioned $(C_2$-$C_4)$alkenyl groups are monosubstituted with $(C_1$-$C_4)$ alkoxy, —COOH or —COOR$^9$ (and preferably with methoxy and —COOH). Vinyl groups are most preferably substituted in 2-position with —COOH; allyl groups are most preferably substituted in 3-position with methoxy.

In case $R^4$ represents "$(C_2$-$C_4)$alkenyl" the term refers to an $(C_2$-$C_4)$alkenyl group as defined above. Preferred examples are vinyl and allyl. The above-mentioned $(C_2$-$C_4)$alkenyl groups are monosubstituted with $(C_1$-$C_4)$ alkoxy or —COOR$^9$ (and preferably with methoxy). Vinyl groups are most preferably substituted in 2-position with —COOR$^9$; allyl groups are most preferably substituted in 3-position with methoxy.

The term "alkoxy", used alone or in combination, refers to a saturated straight or branched chain alkoxy group containing one to four carbon atoms. The term "$(C_x$—$C_y)$ alkoxy" (x and y each being an integer) refers to an alkoxy group as defined before containing x to y carbon atoms. For example a $(C_1$-$C_6)$alkoxy group contains from one to six carbon atoms. Representative examples of alkoxy groups include methoxy, ethoxy, n-propoxy, iso-propoxy, n-butoxy, iso-butoxy, sec-butoxy, tert-butoxy, n-pentoxy, 1-methyl-butoxy, 2-methyl-butoxy, 3-methyl-butoxy, 1,1-dimethyl-propoxy, 1,2-dimethyl-propoxy, 2,2-dimethyl-propoxy and n-hexyloxy (notably methoxy, ethoxy, n-propoxy, iso-propoxy, n-butoxy, iso-butoxy, sec-butoxy and tert-butoxy).

In case $R^1$ represents "$(C_1-C_6)$alkoxy" the term refers to an $(C_1-C_6)$alkoxy group as defined above. Preferred examples are methoxy, ethoxy, n-propoxy, n-butoxy, n-pentoxy and n-hexyloxy. More preferred are ethoxy and n-butoxy and most preferred is n-butoxy.

In case $R^1$ represents "$(C_1-C_4)$alkoxy" the term refers to an $(C_1-C_4)$alkoxy group as defined above. Preferred examples are ethoxy and n-butoxy. More preferred is n-butoxy.

In case $R^2$ represents "$(C_1-C_4)$alkyl which is monosubstituted with $(C_1-C_4)$alkoxy" the term "$(C_1-C_4)$alkoxy" refers to an $(C_1-C_4)$alkoxy group as defined above. Preferred examples are methoxy and ethoxy. More preferred is methoxy.

In case $R^2$ represents "$(C_2-C_4)$alkenyl which is monosubstituted with $(C_1-C_4)$alkoxy" the term "$(C_1-C_4)$alkoxy" refers to an $(C_1-C_4)$alkoxy group as defined above. Preferred examples are methoxy and ethoxy. More preferred is methoxy.

In case $R^2$ represents "$(C_1-C_4)$alkyl-amino which is monosubstituted with $(C_1-C_4)$alkoxy" the term "$(C_1-C_4)$alkoxy" refers to an $(C_1-C_4)$alkoxy group as defined above. Preferred examples are methoxy and ethoxy. More preferred is methoxy.

In case $R^2$ represents "heterocyclyl which is monosubstituted with $(C_1-C_4)$alkoxy" the term "$(C_1-C_4)$alkoxy" refers to an $(C_1-C_4)$alkoxy group as defined above. Preferred examples are methoxy and ethoxy. More preferred is methoxy.

In case $R^3$ represents "aryl which is substituted with $(C_1-C_4)$alkoxy" the term "$(C_1-C_4)$alkoxy" refers to an $(C_1-C_4)$alkoxy group as defined above. Preferred examples are methoxy and ethoxy. More preferred is methoxy.

In case $R^4$ represents "$(C_1-C_4)$alkyl which is monosubstituted with $(C_1-C_4)$alkoxy" the term "$(C_1-C_4)$alkoxy" refers to an $(C_1-C_4)$alkoxy group as defined above. Preferred examples are methoxy and ethoxy. More preferred is methoxy.

In case $R^4$ represents "$(C_2-C_4)$alkenyl which is monosubstituted with $(C_1-C_4)$alkoxy" the term "$(C_1-C_4)$alkoxy" refers to an $(C_1-C_4)$alkoxy group as defined above. Preferred examples are methoxy and ethoxy. More preferred is methoxy.

In case $R^6$ represents "$(C_1-C_4)$alkoxy-C(O)—OCH$_2$—" the term $(C_1-C_4)$alkoxy refers to an $(C_1-C_4)$alkoxy group as defined above. Preferred examples are methoxy and ethoxy. More preferred is ethoxy.

The term "$(C_1-C_4)$alkyl-amino", used alone or in combination, refers to an amino group which is monosubstituted with a $(C_1-C_4)$alkyl group as defined above. Representative examples of $(C_1-C_4)$alkyl-amino groups include methyl-amino, ethyl-amino, n-propyl-amino, iso-propyl-amino, n-butyl-amino, iso-butyl-amino, sec-butyl-amino and tert-butyl-amino. The $(C_1-C_4)$alkyl-amino group may be unsubstituted or monosubstituted in the $(C_1-C_4)$alkyl part as explicitly defined.

In case $R^2$ represents "$(C_1-C_4)$alkyl-amino" the term refers to a $(C_1-C_4)$alkyl-amino group as defined above. Preferred examples are methyl-amino, ethyl-amino and n-propyl-amino. More preferred are ethyl-amino and n-propyl-amino. The $(C_1-C_4)$alkyl group of the above-mentioned $(C_1-C_4)$alkyl-amino groups is monosubstituted with hydroxy, $(C_1-C_4)$alkoxy, —COOH or —COOR$^9$ (and preferably with hydroxy, methoxy or —COOH).

The term "di-alkyl-amino", used alone or in combination, refers to an amino group which is substituted by two alkyl groups as defined above, wherein the two alkyl groups are each containing one to six carbon atoms and may be the same or different. The term "di-$(C_x—C_y)$alkyl-amino" (x and y each being an integer) refers to an amino group which is substituted by two $(C_x—C_y)$alkyl groups as defined above, wherein the two $(C_x—C_y)$alkyl groups may be the same or different. Representative examples of di-alkyl-amino groups include di-methyl-amino, ethyl-methyl-amino, methyl-n-propyl-amino, methyl-iso-propyl-amino, n-butyl-methyl-amino, iso-butyl-methyl-amino, sec-butyl-methyl-amino, tert-butyl-methyl-amino, methyl-n-pentyl-amino, n-hexyl-methyl-amino, di-ethyl-amino, ethyl-n-propyl-amino, ethyl-iso-propyl-amino, n-butyl-ethyl-amino, iso-butyl-ethyl-amino, sec-butyl-ethyl-amino, tert-butyl-ethyl-amino, ethyl-n-pentyl-amino and n-hexyl-ethyl-amino.

In case $R^2$ represents "di-$(C_1-C_4)$alkyl-amino" the term refers to an amino group which is substituted by two $(C_1-C_4)$alkyl groups as defined above, wherein the two $(C_1-C_4)$alkyl groups may be the same or different. Preferred examples are di-methyl-amino, ethyl-methyl-amino, methyl-n-propyl-amino and n-butyl-methyl-amino. More preferred is n-butyl-methyl-amino.

In case $R^4$ represents "di-$(C_1-C_6)$alkyl-amino" the term refers to an amino group which is substituted by two $(C_1-C_6)$alkyl groups as defined above, wherein the two $(C_1-C_6)$alkyl groups may be the same or different. Preferred examples are di-methyl-amino, ethyl-methyl-amino, methyl-n-propyl-amino, n-butyl-methyl-amino, methyl-n-pentyl-amino and n-hexyl-methyl-amino. More preferred is n-hexyl-methyl-amino.

The term "$(C_1-C_4)$alkoxy-C(O)—$(C_1-C_4)$alkyl-" as used in $R^7$ refers to an $(C_1-C_4)$alkyl-group as defined above, wherein one hydrogen atom has been replaced by a "$(C_1-C_4)$alkoxy-C(O)-" group, wherein the term "$(C_1-C_4)$alkoxy" refers to an $(C_1-C_4)$alkoxy-group as defined above. Preferably the $(C_1-C_4)$alkoxy-C(O)— group is attached to the same carbon atom of the $(C_1-C_4)$alkyl-group as the nitrogen atom of the —P(O)(NHR$^7$)$_2$ group. Preferred examples of $(C_1-C_4)$alkoxy-C(O)—$(C_1-C_4)$alkyl-groups are methoxycarbonyl-methyl, 1-methoxycarbonyl-ethyl, ethoxycarbonyl-methyl and 1-ethoxycarbonyl-ethyl. More preferred is 1-ethoxycarbonyl-ethyl.

The term "aryl", used alone or in any combination, refers to phenyl (preferred) or naphthyl. The aryl group is unsubstituted or mono- or di-substituted (preferably unsubstituted or mono-substituted), wherein the substituents are independently selected from the group consisting of halogen (preferred), $(C_1-C_4)$alkyl, $(C_1-C_4)$alkoxy and phenoxy. Examples are phenyl, 2-methylphenyl, 2-methoxyphenyl, 3-methoxyphenyl, 4-fluorophenyl and 2-phenoxyphenyl. Preferred examples are phenyl and 4-fluorophenyl. Most preferred is phenyl.

The term "heterocyclyl", alone or in combination, refers to a 4- to 6-membered saturated monocyclic ring containing 1 or 2 heteroatoms independently selected from the group consisting of sulfur, oxygen and nitrogen (preferably oxygen and nitrogen). Examples of such heterocyclyl groups are azetidinyl, oxetanyl, pyrrolidinyl, tetrahydrofuranyl, tetrahydrothiophenyl, oxazolidinyl, thiazolidinyl, piperidinyl, piperazinyl, morpholinyl, thiomorpholinyl and dioxanyl. The heterocyclyl group may be unsubstituted or substituted as explicitly defined.

In case $R^2$ represents "heterocyclyl" the term refers to a heterocyclyl group as defined above. The heterocyclyl group is unsubstituted or monosubstituted with $(C_1-C_4)$alkyl or $(C_1-C_4)$alkoxy. Preferred examples are pyrrolidinyl, 3-methoxy-pyrrolidinyl (notably (S)-3-methoxy-pyrrolidinyl), 4-methyl-piperazinyl and morpholinyl. More preferred are pyrrolidinyl and (S)-3-methoxy-pyrrolidinyl.

In this patent application, a dotted line shows the point of attachment of the radical drawn. For example, the radical drawn below

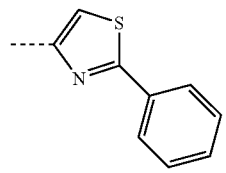

is the 2-phenyl-thiazol-4-yl group.

Besides, the following paragraphs provide definitions of various other terms. Said definitions are intended to apply uniformly throughout the specification and claims unless an otherwise expressly set out definition provides a broader or narrower definition.

The term "pharmaceutically acceptable salts" refers to non-toxic, inorganic or organic acid and/or base addition salts. Reference can be made to "Salt selection for basic drugs", *Int. J. Pharm.* (1986), 33, 201-217.

The term "room temperature" as used herein refers to a temperature of around 25° C.

Unless used regarding temperatures, the term "about" (or alternatively the term "around") placed before a numerical value "X" refers in the current application to an interval extending from X minus 10% of X to X plus 10% of X, and preferably to an interval extending from X minus 5% of X to X plus 5% of X. In the particular case of temperatures, the term "about" (or alternatively the term "around") placed before a temperature "Y" refers in the current application to an interval extending from the temperature Y minus 10° C. to Y plus 10° C., and preferably to an interval extending from Y minus 5° C. to Y plus 5° C.

2) A further embodiment of the invention relates to thiazole derivatives of formula I according to embodiment 1) which are also compounds of formula $I_P$,

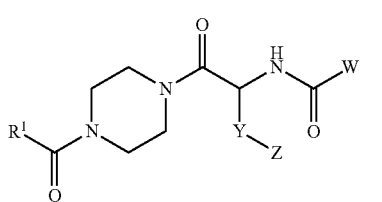

formula $I_P$ wherein
$R^1$ represents $(C_1-C_4)$alkoxy;
Y represents a bond and Z represents hydrogen; or
Y represents $(C_1-C_3)$alkandiyl and Z represents hydrogen, hydroxy, —COOH, —COOR$^5$, —P(O)(OH)$_2$, —P(O)(OR$^6$)$_2$, —P(O)(NHR$^7$)$_2$ or phenyl, wherein the phenyl is substituted with —P(O)(OH)$_2$ or —P(O)(OR$^8$)$_2$;
W represents a group selected from

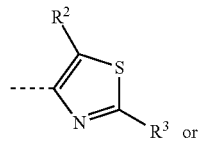
(G1)

or

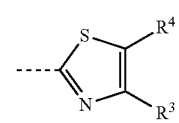
(G2)

$R^2$ represents hydrogen; halogen; $(C_1-C_4)$alkyl which is monosubstituted with $(C_1-C_4)$alkoxy, —COOH or —COOR$^9$; $(C_2-C_4)$alkenyl which is monosubstituted with $(C_1-C_4)$alkoxy, —COOH or —COOR$^9$; phenyl which is unsubstituted or monosubstituted with halogen; $(C_1-C_4)$alkyl-amino, wherein the alkyl-group is monosubstituted with hydroxy, $(C_1-C_4)$alkoxy, —COOH or —COOR$^9$; di-$(C_1-C_4)$alkyl-amino; heterocyclyl which is unsubstituted or monosubstituted with $(C_1-C_4)$alkyl or $(C_1-C_4)$alkoxy; or 2-methoxymethyl-cycloprop-1-yl (notably (1S,2S)-2-methoxymethyl-cycloprop-1-yl);
$R^3$ represents aryl which is unsubstituted or mono- or di-substituted, wherein the substituents are independently selected from the group consisting of halogen, $(C_1-C_4)$alkyl, $(C_1-C_4)$alkoxy and phenoxy;
$R^4$ represents halogen; $(C_1-C_4)$alkyl which is monosubstituted with $(C_1-C_4)$alkoxy, —COOH, or —COOR$^9$; $(C_2-C_4)$alkenyl which is monosubstituted with $(C_1-C_4)$alkoxy or —COOR$^9$; phenyl; or di-$(C_1-C_6)$alkyl-amino;
$R^5$ represents $(C_1-C_4)$alkyl;
$R^6$ represents $(C_1-C_4)$alkyl, $(C_1-C_4)$alkyl-C(O)—OCH$_2$— or $(C_1-C_4)$alkoxy-C(O)—OCH$_2$—;
$R^7$ represents $(C_1-C_4)$alkoxy-C(O)—$(C_1-C_4)$alkyl-;
$R^8$ represents $(C_1-C_4)$alkyl;
$R^9$ represents $(C_1-C_4)$alkyl;
and to the salts (in particular pharmaceutically acceptable salts) of such compounds.

3) A further embodiment of the invention relates to thiazole derivatives of formula I according to any one of embodiments 1) or 2), wherein
$R^1$ represents $(C_1-C_4)$alkoxy;
Y represents a bond and Z represents hydrogen; or
Y represents $(C_1-C_3)$alkandiyl and Z represents hydrogen, hydroxy, —COOH or —COOR$^5$;
W represents a group selected from G1 or G2;
$R^2$ represents hydrogen; halogen; $(C_1-C_4)$alkyl which is monosubstituted with $(C_1-C_4)$alkoxy, —COOH or —COOR$^9$; $(C_2-C_4)$alkenyl which is monosubstituted with $(C_1-C_4)$alkoxy, —COOH or —COOR$^9$; phenyl which is unsubstituted or monosubstituted with halogen; $(C_1-C_4)$alkyl-amino, wherein the alkyl-group is monosubstituted with hydroxy, $(C_1-C_4)$alkoxy, —COOH or —COOR$^9$; di-$(C_1-C_4)$alkyl-amino; heterocyclyl which is unsubstituted or monosubstituted with $(C_1-C_4)$alkyl or $(C_1-C_4)$alkoxy; or 2-methoxymethyl-cycloprop-1-yl (notably (1S,2S)-2-methoxymethyl-cycloprop-1-yl);
$R^3$ represents aryl which is unsubstituted or mono- or di-substituted, wherein the substituents are independently selected from the group consisting of halogen, $(C_1-C_4)$alkyl, $(C_1-C_4)$alkoxy and phenoxy;

$R^4$ represents halogen; $(C_1\text{-}C_4)$alkyl which is monosubstituted with $(C_1\text{-}C_4)$alkoxy, —COOH, or —COOR$^9$; $(C_2\text{-}C_4)$alkenyl which is monosubstituted with $(C_1\text{-}C_4)$alkoxy or —COOR$^9$; phenyl; or di-$(C_1\text{-}C_6)$alkyl-amino;
$R^5$ represents $(C_1\text{-}C_4)$alkyl;
$R^9$ represents $(C_1\text{-}C_4)$alkyl;
and to the salts (in particular pharmaceutically acceptable salts) of such compounds.

4) A further embodiment of the invention relates to thiazole derivatives of formula I according to any one of embodiments 1) or 2), wherein
$R^1$ represents $(C_1\text{-}C_4)$alkoxy;
Y represents $(C_1\text{-}C_3)$alkandiyl and Z represents —P(O)(OH)$_2$, —P(O)(OR$^6$)$_2$, —P(O)(NHR$^7$)$_2$ or phenyl, wherein the phenyl is substituted with —P(O)(OH)$_2$ or —P(O)(OR$^8$)$_2$;
W represents a group selected from G1 or G2;
$R^2$ represents hydrogen; halogen; $(C_1\text{-}C_4)$alkyl which is monosubstituted with $(C_1\text{-}C_4)$alkoxy, —COOH or —COOR$^9$; $(C_2\text{-}C_4)$alkenyl which is monosubstituted with $(C_1\text{-}C_4)$alkoxy, —COOH or —COOR$^9$; phenyl which is unsubstituted or monosubstituted with halogen; $(C_1\text{-}C_4)$alkyl-amino, wherein the alkyl-group is monosubstituted with hydroxy, $(C_1\text{-}C_4)$alkoxy, —COOH or —COOR$^9$; di-$(C_1\text{-}C_4)$alkyl-amino; heterocyclyl which is unsubstituted or monosubstituted with $(C_1\text{-}C_4)$alkyl or $(C_1\text{-}C_4)$alkoxy; or 2-methoxymethyl-cycloprop-1-yl (notably (1S,2S)-2-methoxymethyl-cycloprop-1-yl);
$R^3$ represents aryl which is unsubstituted or mono- or di-substituted, wherein the substituents are independently selected from the group consisting of halogen, $(C_1\text{-}C_4)$alkyl, $(C_1\text{-}C_4)$alkoxy and phenoxy;
$R^4$ represents halogen; $(C_1\text{-}C_4)$alkyl which is monosubstituted with $(C_1\text{-}C_4)$alkoxy, —COOH, or —COOR$^9$; $(C_2\text{-}C_4)$alkenyl which is monosubstituted with $(C_1\text{-}C_4)$alkoxy or —COOR$^9$; phenyl; or di-$(C_1\text{-}C_6)$alkyl-amino;
$R^6$ represents $(C_1\text{-}C_4)$alkyl, $(C_1\text{-}C_4)$alkyl-C(O)—OCH$_2$— or $(C_1\text{-}C_4)$alkoxy-C(O)—OCH$_2$—;
$R^7$ represents $(C_1\text{-}C_4)$alkoxy-C(O)—$(C_1\text{-}C_4)$alkyl-;
$R^8$ represents $(C_1\text{-}C_4)$alkyl;
$R^9$ represents $(C_1\text{-}C_4)$alkyl;
and to the salts (in particular pharmaceutically acceptable salts) of such compounds.

5) A further embodiment of the invention relates to thiazole derivatives of formula I according to any one of embodiments 1) or 2), wherein
$R^1$ represents $(C_1\text{-}C_4)$alkoxy;
Y represents $(C_1\text{-}C_3)$alkandiyl and Z represents —P(O)(OH)$_2$, —P(O)(OR$^6$)$_2$, —P(O)(NHR$^7$)$_2$ or phenyl, wherein the phenyl is substituted with —P(O)(OH)$_2$ or —P(O)(OR$^8$)$_2$;
W represents a group selected from G1 or G2;
$R^2$ represents hydrogen; phenyl; di-$(C_1\text{-}C_4)$alkyl-amino; or heterocyclyl which is mono-substituted with $(C_1\text{-}C_4)$alkyl;
$R^3$ represents aryl which is unsubstituted or mono-substituted with halogen;
$R^4$ represents halogen or phenyl;
$R^6$ represents $(C_1\text{-}C_4)$alkyl, $(C_1\text{-}C_4)$alkyl-C(O)—OCH$_2$— or $(C_1\text{-}C_4)$alkoxy-C(O)—OCH$_2$—;
$R^7$ represents $(C_1\text{-}C_4)$alkoxy-C(O)—$(C_1\text{-}C_4)$alkyl-;
$R^8$ represents $(C_1\text{-}C_4)$alkyl;
and to the salts (in particular pharmaceutically acceptable salts) of such compounds.

6) A further embodiment of the invention relates to thiazole derivatives of formula I according to any one of embodiments 1) or 2), wherein
$R^1$ represents $(C_1\text{-}C_4)$alkoxy;
Y represents $(C_1\text{-}C_3)$alkandiyl (preferably methandiyl) and Z represents —P(O)(OH)$_2$ or phenyl, wherein the phenyl is substituted with —P(O)(OH)$_2$;
W represents a group G1;
$R^2$ represents hydrogen; phenyl; or di-$(C_1\text{-}C_4)$alkyl-amino;
$R^3$ represents phenyl which is unsubstituted or mono-substituted with halogen;
and to the salts (in particular pharmaceutically acceptable salts) of such compounds.

7) A further embodiment of the invention relates to thiazole derivatives of formula I according to any one of embodiments 1) to 6) and to the salts (in particular pharmaceutically acceptable salts) of such compounds, which have a configuration as depicted in formula I$_{ST1}$

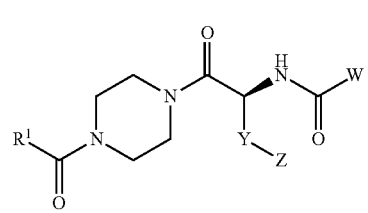

formula I$_{ST1}$

8) A further embodiment of the invention relates to thiazole derivatives of formula I according to any one of embodiments 1) to 7), wherein
$R^1$ represents ethoxy or n-butoxy (preferably n-butoxy);
and to the salts (in particular pharmaceutically acceptable salts) of such compounds.

9) A further embodiment of the invention relates to thiazole derivatives of formula I according to any one of embodiments 1), 2), 3), 7) or 8), wherein
Y represents a bond and Z represents hydrogen;
and to the salts (in particular pharmaceutically acceptable salts) of such compounds.

10) A further embodiment of the invention relates to thiazole derivatives of formula I according to any one of embodiments 1), 2), 3), 7) or 8)), wherein
Y represents $(C_1\text{-}C_3)$alkandiyl and Z represents hydroxy or —COOH;
and to the salts (in particular pharmaceutically acceptable salts) of such compounds.

11) A further embodiment of the invention relates to thiazole derivatives of formula I according to any one of embodiments 1), 2), 3), 7) or 8), wherein
Y represents methandiyl and Z represents hydroxy;
and to the salts (in particular pharmaceutically acceptable salts) of such compounds.

12) A further embodiment of the invention relates to thiazole derivatives of formula I according to any one of embodiments 1), 2), 3), 7) or 8), wherein
Y represents ethan-1,2-diyl and Z represents —COOH;
and to the salts (in particular pharmaceutically acceptable salts) of such compounds.

13) A further embodiment of the invention relates to thiazole derivatives of formula I according to any one of embodiments 1), 2), 4), 5), 7) or 8), wherein
Y represents $(C_1\text{-}C_3)$alkandiyl and Z represents —P(O)(OH)$_2$, —P(O)(OR$^6$)$_2$, —P(O)(NHR$^7$)$_2$ or phenyl, wherein the phenyl is substituted with —P(O)(OH)$_2$ or —P(O)(OR$^8$)$_2$;
and to the salts (in particular pharmaceutically acceptable salts) of such compounds.

14) A further embodiment of the invention relates to thiazole derivatives of formula I according to any one of embodiments 1), 2), 4), 5), 7) or 8), wherein
Y represents ($C_1$-$C_3$)alkandiyl (preferably methandiyl) and Z represents —P(O)(OR$^6$)$_2$, —P(O)(NHR$^7$)$_2$ or phenyl, wherein the phenyl is substituted with —P(O)(OR$^8$)$_2$;
and to the salts (in particular pharmaceutically acceptable salts) of such compounds.

15) A further embodiment of the invention relates to thiazole derivatives of formula I according to any one of embodiments 1), 2) or 4) to 8), wherein
Y represents ($C_1$-$C_3$)alkandiyl (preferably methandiyl) and Z represents —P(O)(OH)$_2$ or phenyl,
wherein the phenyl is substituted with —P(O)(OH)$_2$;
and to the salts (in particular pharmaceutically acceptable salts) of such compounds.

16) A further embodiment of the invention relates to thiazole derivatives of formula I according to any one of embodiments 1), 2) or 4) to 8), wherein
Y represents methandiyl and Z represents —P(O)(OH)$_2$;
and to the salts (in particular pharmaceutically acceptable salts) of such compounds.

17) A further embodiment of the invention relates to thiazole derivatives of formula I according to any one of embodiments 1), 2) or 4) to 8), wherein
Y represents methandiyl and Z represents phenyl, wherein the phenyl is substituted with —P(O)(OH)$_2$ (preferably attached to the phenyl group in para-position);
and to the salts (in particular pharmaceutically acceptable salts) of such compounds.

18) A further embodiment of the invention relates to thiazole derivatives of formula I according to any one of embodiments 1) to 17), wherein
W represents the group G1;
and to the salts (in particular pharmaceutically acceptable salts) of such compounds.

19) A further embodiment of the invention relates to thiazole derivatives of formula I according to any one of embodiments 1) to 5) or 7) to 17), wherein
W represents the group G2;
and to the salts (in particular pharmaceutically acceptable salts) of such compounds.

20) A further embodiment of the invention relates to thiazole derivatives of formula I according to any one of embodiments 1) to 4) or 7) to 18), wherein
$R^2$ represents hydrogen; halogen; ($C_1$-$C_4$)alkyl which is monosubstituted with ($C_1$-$C_4$)alkoxy or —COOH; ($C_2$-$C_4$) alkenyl which is monosubstituted with ($C_1$-$C_4$)alkoxy or —COOH; phenyl; ($C_1$-$C_4$)alkyl-amino, wherein the alkyl-group is monosubstituted with hydroxy, ($C_1$-$C_4$)alkoxy or —COOH; di-($C_1$-$C_4$)alkyl-amino; heterocyclyl which is unsubstituted or monosubstituted with ($C_1$-$C_4$)alkyl or ($C_1$-$C_4$)alkoxy; or (1S,2S)-2-methoxymethyl-cycloprop-1-yl;
and to the salts (in particular pharmaceutically acceptable salts) of such compounds.

21) A further embodiment of the invention relates to thiazole derivatives of formula I according to any one of embodiments 1) to 4) or 7) to 18), wherein
$R^2$ represents hydrogen; halogen (preferably chlorine or bromine); ($C_1$-$C_4$)alkyl (preferably ethyl or n-propyl) which is monosubstituted with methoxy or —COOH; ($C_2$-$C_4$)alkenyl (preferably vinyl) which is monosubstituted with methoxy or —COOH; phenyl; ($C_1$-$C_4$)alkyl-amino, wherein the alkyl-group is monosubstituted with hydroxy, methoxy or COOH (preferably hydroxy or methoxy); di-($C_1$-$C_4$)alkyl-amino (preferably n-butyl-methyl-amino); heterocyclyl (preferably pyrrolidinyl, piperazinyl or morpholinyl) which is unsubstituted or monosubstituted with ($C_1$-$C_4$)alkyl (preferably methyl) or ($C_1$-$C_4$)alkoxy (preferably methoxy); or (1S,2S)-2-methoxymethyl-cycloprop-1-yl;
and to the salts (in particular pharmaceutically acceptable salts) of such compounds.

22) A further embodiment of the invention relates to thiazole derivatives of formula I according to any one of embodiments 1) to 5) or 7) to 18), wherein
$R^2$ represents hydrogen; phenyl; di-($C_1$-$C_4$)alkyl-amino; or heterocyclyl which is mono-substituted with ($C_1$-$C_4$)alkyl;
and to the salts (in particular pharmaceutically acceptable salts) of such compounds.

23) A further embodiment of the invention relates to thiazole derivatives of formula I according to any one of embodiments 1) to 18), wherein
$R^2$ represents hydrogen; phenyl; or di-($C_1$-$C_4$)alkyl-amino;
and to the salts (in particular pharmaceutically acceptable salts) of such compounds.

24) A further embodiment of the invention relates to thiazole derivatives of formula I according to any one of embodiments 1) to 18), wherein
$R^2$ represents hydrogen;
and to the salts (in particular pharmaceutically acceptable salts) of such compounds.

25) A further embodiment of the invention relates to thiazole derivatives of formula I according to any one of embodiments 1) to 24), wherein
$R^3$ represents aryl (preferably phenyl) which is unsubstituted or mono-substituted with halogen (preferably fluorine);
and to the salts (in particular pharmaceutically acceptable salts) of such compounds.

26) A further embodiment of the invention relates to thiazole derivatives of formula I according to any one of embodiments 1) to 24), wherein
$R^3$ represents phenyl;
and to the salts (in particular pharmaceutically acceptable salts) of such compounds.

27) A further embodiment of the invention relates to thiazole derivatives of formula I according to any one of embodiments 1) to 5), 7) to 17), 19), 25) or 26), wherein
$R^4$ represents halogen (preferably bromine) or phenyl;
and to the salts (in particular pharmaceutically acceptable salts) of such compounds.

28) A further embodiment of the invention relates to thiazole derivatives of formula I according to any one of embodiments 1), 2), 4), 5), 7), 8), 13), 14) or 18) to 27), wherein
$R^6$ represents ($C_1$-$C_4$)alkyl (preferably ethyl), CH$_3$—C(O)—OCH$_2$— or CH$_3$CH$_2$O—C(O)—OCH$_2$—;
and to the salts (in particular pharmaceutically acceptable salts) of such compounds.

29) A further embodiment of the invention relates to thiazole derivatives of formula I according to any one of embodiments 1), 2), 4), 5), 7), 8), 13), 14) or 18) to 27), wherein
$R^7$ represents CH$_3$CH$_2$O—C(O)—CH(CH$_3$)—;
and to the salts (in particular pharmaceutically acceptable salts) of such compounds.

30) A further embodiment of the invention relates to thiazole derivatives of formula I according to any one of embodiments 1), 2), 4), 5), 7), 8), 13), 14) or 18) to 27), wherein
$R^8$ represents ethyl;
and to the salts (in particular pharmaceutically acceptable salts) of such compounds.

31) Preferred compounds of formula (I) as defined in embodiment 1) are selected from the group consisting of:
4-{2-[(2-Phenyl-thiazole-4-carbonyl)-amino]-acetyl}-piperazine-1-carboxylic acid ethyl ester;
4-{(S)-4-Carboxy-2-[(2-phenyl-thiazole-4-carbonyl)-amino]-butyryl}-piperazine-1-carboxylic acid ethyl ester;
4-((S)-4-Carboxy-2-{[2-(2-phenoxy-phenyl)-thiazole-4-carbonyl]-amino}-butyryl)-piperazine-1-carboxylic acid butyl ester;

4-((S)-4-Carboxy-2-{[2-(3-methoxy-phenyl)-thiazole-4-carbonyl]-amino}-butyryl)-piperazine-1-carboxylic acid butyl ester;

4-((S)-4-Carboxy-2-{[2-(2-methoxy-phenyl)-thiazole-4-carbonyl]-amino}-butyryl)-piperazine-1-carboxylic acid butyl ester;

4-{(S)-4-Carboxy-2-[(2-o-tolyl-thiazole-4-carbonyl)-amino]-butyryl}-piperazine-1-carboxylic acid butyl ester;

4-{(S)-4-Carboxy-2-[(2-phenyl-thiazole-4-carbonyl)-amino]-butyryl}-piperazine-1-carboxylic acid butyl ester;

4-{(R)-3-(Diethoxy-phosphoryl)-2-[(2-phenyl-thiazole-4-carbonyl)-amino]-propionyl}-piperazine-1-carboxylic acid butyl ester;

4-{(R)-2-[(2-Phenyl-thiazole-4-carbonyl)-amino]-3-phosphono-propionyl}-piperazine-1-carboxylic acid butyl ester;

4-{(S)-3-[4-(Diethoxy-phosphoryl)-phenyl]-2-[(2-phenyl-thiazole-4-carbonyl)-amino]-propionyl}-piperazine-1-carboxylic acid butyl ester;

4-[(S)-2-[(2-Phenyl-thiazole-4-carbonyl)-amino]-3-(4-phosphono-phenyl)-propionyl]-piperazine-1-carboxylic acid butyl ester;

4-{(S)-3-[4-(Diethoxy-phosphoryl)-phenyl]-2-[(2-phenyl-thiazole-4-carbonyl)-amino]-propionyl}-piperazine-1-carboxylic acid ethyl ester;

4-[(S)-2-[(2-Phenyl-thiazole-4-carbonyl)-amino]-3-(4-phosphono-phenyl)-propionyl]-piperazine-1-carboxylic acid ethyl ester;

4-{(S)-2-[(5-Bromo-2-phenyl-thiazole-4-carbonyl)-amino]-4-tert-butoxycarbonyl-butyryl}-piperazine-1-carboxylic acid butyl ester;

4-{(S)-2-[(5-Bromo-2-phenyl-thiazole-4-carbonyl)-amino]-4-carboxy-butyryl}-piperazine-1-carboxylic acid butyl ester;

4-{(S)-4-Carboxy-2-[(5-chloro-2-phenyl-thiazole-4-carbonyl)-amino]-butyryl}-piperazine-1-carboxylic acid butyl ester;

4-{(S)-4-Carboxy-2-[(2,5-diphenyl-thiazole-4-carbonyl)-amino]-butyryl}-piperazine-1-carboxylic acid butyl ester;

4-((S)-4-Carboxy-2-{[5-((1S,2S)-2-methoxymethyl-cyclopropyl)-2-phenyl-thiazole-4-carbonyl]-amino}-butyryl)-piperazine-1-carboxylic acid butyl ester;

4-((S)-4-Carboxy-2-{[5-((E)-2-carboxy-vinyl)-2-phenyl-thiazole-4-carbonyl]-amino}-butyryl)-piperazine-1-carboxylic acid butyl ester;

4-((S)-4-Carboxy-2-{[5-(2-carboxy-ethyl)-2-phenyl-thiazole-4-carbonyl]-amino}-butyryl)-piperazine-1-carboxylic acid butyl ester;

4-((S)-4-Carboxy-2-{[5-((E)-3-methoxy-propenyl)-2-phenyl-thiazole-4-carbonyl]-amino}-butyryl)-piperazine-1-carboxylic acid butyl ester;

4-((S)-4-Carboxy-2-{[5-(3-methoxy-propyl)-2-phenyl-thiazole-4-carbonyl]-amino}-butyryl)-piperazine-1-carboxylic acid butyl ester;

4-{(S)-4-Carboxy-2-[(5-morpholin-4-yl-2-phenyl-thiazole-4-carbonyl)-amino]-butyryl}-piperazine-1-carboxylic acid butyl ester;

4-{(S)-4-Carboxy-2-[(2-phenyl-5-pyrrolidin-1-yl-thiazole-4-carbonyl)-amino]-butyryl}-piperazine-1-carboxylic acid butyl ester;

4-((S)-4-Carboxy-2-{[5-((S)-3-methoxy-pyrrolidin-1-yl)-2-phenyl-thiazole-4-carbonyl]-amino}-butyryl)-piperazine-1-carboxylic acid butyl ester;

4-{2-[(2-Phenyl-thiazole-4-carbonyl)-amino]-acetyl}-piperazine-1-carboxylic acid butyl ester;

4-(2-{[5-(3-Hydroxy-propylamino)-2-phenyl-thiazole-4-carbonyl]-amino}-acetyl)-piperazine-1-carboxylic acid butyl ester;

4-(2-{[5-(3-Methoxy-propylamino)-2-phenyl-thiazole-4-carbonyl]-amino}-acetyl)-piperazine-1-carboxylic acid butyl ester;

4-(2-{[5-(3-Fluoro-phenyl)-2-phenyl-thiazole-4-carbonyl]-amino}-acetyl)-piperazine-1-carboxylic acid butyl ester;

4-(2-{[5-((E)-2-Ethoxycarbonyl-vinyl)-2-phenyl-thiazole-4-carbonyl]-amino}-acetyl)-piperazine-1-carboxylic acid butyl ester;

4-(2-{[5-((E)-2-Carboxy-vinyl)-2-phenyl-thiazole-4-carbonyl]-amino}-acetyl)-piperazine-1-carboxylic acid butyl ester;

4-(2-{[5-(2-Ethoxycarbonyl-ethyl)-2-phenyl-thiazole-4-carbonyl]-amino}-acetyl)-piperazine-1-carboxylic acid butyl ester;

4-(2-{[5-(2-Carboxy-ethyl)-2-phenyl-thiazole-4-carbonyl]-amino}-acetyl)-piperazine-1-carboxylic acid butyl ester;

4-(2-{[5-(3-Methoxy-propenyl)-2-phenyl-thiazole-4-carbonyl]-amino}-acetyl)-piperazine-1-carboxylic acid butyl ester;

4-(2-{[5-(3-Methoxy-propyl)-2-phenyl-thiazole-4-carbonyl]-amino}-acetyl)-piperazine-1-carboxylic acid butyl ester;

4-{(S)-3-Methyl-2-[(2-phenyl-thiazole-4-carbonyl)-amino]-butyryl}-piperazine-1-carboxylic acid butyl ester;

4-{(S)-2-[(5-Bromo-2-phenyl-thiazole-4-carbonyl)-amino]-3-hydroxy-propionyl}-piperazine-1-carboxylic acid butyl ester;

4-{(S)-3-Hydroxy-2-[(2-phenyl-thiazole-4-carbonyl)-amino]-propionyl}-piperazine-1-carboxylic acid butyl ester;

4-((S)-2-{[5-((E)-2-Carboxy-vinyl)-2-phenyl-thiazole-4-carbonyl]-amino}-3-hydroxy-propionyl)-piperazine-1-carboxylic acid butyl ester;

4-((S)-2-{[5-(2-Carboxy-ethyl)-2-phenyl-thiazole-4-carbonyl]-amino}-3-hydroxy-propionyl)-piperazine-1-carboxylic acid butyl ester;

4-((R)-2-{[2-(4-Fluoro-phenyl)-thiazole-4-carbonyl]-amino}-3-phosphono-propionyl)-piperazine-1-carboxylic acid butyl ester;

4-{(R)-3-(Diethoxy-phosphoryl)-2-[(2,5-diphenyl-thiazole-4-carbonyl)-amino]-propionyl}-piperazine-1-carboxylic acid butyl ester;

4-{(R)-2-[(2,5-Diphenyl-thiazole-4-carbonyl)-amino]-3-phosphono-propionyl}-piperazine-1-carboxylic acid butyl ester;

4-((R)-3-(Diethoxy-phosphoryl)-2-{[5-(4-methyl-piperazin-1-yl)-2-phenyl-thiazole-4-carbonyl]-amino}-propionyl)-piperazine-1-carboxylic acid butyl ester;

4-((R)-2-{[5-(4-Methyl-piperazin-1-yl)-2-phenyl-thiazole-4-carbonyl]-amino}-3-phosphono-propionyl)-piperazine-1-carboxylic acid butyl ester;

4-[(R)-2-{[5-(Butyl-methyl-amino)-2-phenyl-thiazole-4-carbonyl]-amino}-3-(diethoxy-phosphoryl)-propionyl]-piperazine-1-carboxylic acid butyl ester;

4-((R)-2-{[5-(Butyl-methyl-amino)-2-phenyl-thiazole-4-carbonyl]-amino}-3-phosphono-propionyl)-piperazine-1-carboxylic acid butyl ester;

4-{(R)-2-[(5-Bromo-4-phenyl-thiazole-2-carbonyl)-amino]-3-phosphono-propionyl}-piperazine-1-carboxylic acid butyl ester;

4-{(R)-2-[(4,5-Diphenyl-thiazole-2-carbonyl)-amino]-3-phosphono-propionyl}-piperazine-1-carboxylic acid butyl ester;

4-{2-[(4,5-Diphenyl-thiazole-2-carbonyl)-amino]-acetyl}-piperazine-1-carboxylic acid butyl ester;

4-(2-{[5-((E)-3-Methoxy-propenyl)-4-phenyl-thiazole-2-carbonyl]-amino}-acetyl)-piperazine-1-carboxylic acid butyl ester;

4-(2-{[5-(3-Methoxy-propyl)-4-phenyl-thiazole-2-carbonyl]-amino}-acetyl)-piperazine-1-carboxylic acid butyl ester;

4-(2-{[5-((E)-2-Ethoxycarbonyl-vinyl)-4-phenyl-thiazole-2-carbonyl]-amino}-acetyl)-piperazine-1-carboxylic acid butyl ester;

4-(2-{[5-(2-Methoxycarbonyl-ethyl)-4-phenyl-thiazole-2-carbonyl]-amino}-acetyl)-piperazine-1-carboxylic acid butyl ester;

4-(2-{[5-(2-Carboxy-ethyl)-4-phenyl-thiazole-2-carbonyl]-amino}-acetyl)-piperazine-1-carboxylic acid butyl ester;

4-{(S)-2-[(5-Bromo-4-phenyl-thiazole-2-carbonyl)-amino]-4-carboxy-butyryl}-piperazine-1-carboxylic acid butyl ester;

4-{(R)-3-[Bis-(acetoxymethoxy)-phosphoryl]-2-[(2-phenyl-thiazole-4-carbonyl)-amino]-propionyl}-piperazine-1-carboxylic acid butyl ester;

N,N'-Bis-((S)-1-Ethoxycarbonylethyl)-(R)-2-[(2-phenyl-thiazole-4-carbonyl)-amino]-3-oxo-3-(4-butoxy-carbonyl-piperazin-1-yl)-propyl-phosphonic acid diamide;

4-{(R)-3-[Bis-(ethoxycarbonyloxymethoxy)-phosphoryl]-2-[(2-phenyl-thiazole-4-carbonyl)-amino]-propionyl}-piperazine-1-carboxylic acid butyl ester;

4-(2-{[5-(Hexyl-methyl-amino)-4-phenyl-thiazole-2-carbonyl]amino}-acetyl)-piperazine-1-carboxylic acid butyl ester;

4-(2-{[5-(2-Carboxy-ethylamino)-2-phenyl-thiazole-4-carbonyl]-amino}-acetyl)-piperazine-1-carboxylic acid butyl ester; and 4-(2-{[5-(2-Ethoxycarbonyl-ethylamino)-2-phenyl-thiazole-4-carbonyl]-amino}-acetyl)-piperazine-1-carboxylic acid butyl ester;

or a salt (in particular a pharmaceutically acceptable salt) of such a compound;

wherein it is well understood that any stereogenic center of any above listed compound, which is not explicitly assigned, may be in absolute (R)- or (S)-configuration; if not explicitly assigned, any double bond of any above listed compound may be in (E)- or (Z)-configuration.

32) A further object of the invention is the compounds of formula I as defined in one of embodiments 1) to 31) above, or their pharmaceutically acceptable salts, as medicaments.

The compounds of formula I and their pharmaceutically acceptable salts can be used as medicaments, e.g. in the form of pharmaceutical compositions for enteral or parenteral administration.

33) The invention thus also relates to pharmaceutical compositions containing at least one compound according to one of embodiments 1) to 31) above, or a pharmaceutically acceptable salt thereof, and a pharmaceutically acceptable carrier, diluent or excipient. In particular, the invention relates to pharmaceutical compositions containing at least one compound of formula I and one or more pharmaceutically acceptable carriers, diluents or excipients.

The production of the pharmaceutical compositions can be effected in a manner which will be familiar to any person skilled in the art (see for example Remington, *The Science and Practice of Pharmacy*, 21st Edition (2005), Part 5, "Pharmaceutical Manufacturing" [published by Lippincott Williams & Wilkins]) by bringing the described compounds of formula I or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

34) The compounds according to formula I as defined in embodiments 1) to 31) above and the pharmaceutically acceptable salts thereof may be used for the preparation of a medicament, and are suitable:

for the treatment or prophylaxis of diseases including stable angina, unstable angina, myocardial infarction, embolism (including complications of atherosclerosis, notably embolic stroke), arterial thrombosis (including primary arterial thrombotic complications of atherosclerosis, notably thrombotic stroke), venous thrombosis (notably deep vein thrombosis), thrombosis secondary to vascular damage or to inflammation (including vasculitis, arteritis and glomerulonephritis), venoocclusive diseases, transient ischaemic attacks, peripheral vascular diseases, myocardial infarction with or without thrombolysis, myeloproliferative disease, thrombocythaemia, sickle cell disease, inflammatory bowel disease, thrombotic thrombocytopaenic purpura, haemolytic uraemic syndrome;

for preventing thrombotic complications of septicaemia, adult respiratory distress syndrome, anti-phospholipid syndrome, heparin-induced thrombocytopaenia and pre-eclampsia/eclampsia;

for preventing cardiovascular complications after certain surgery procedures (notably coronary revascularisation like angioplasty (PTCA), other vascular graft surgery, endarterectomy or stent placement) or after accidental trauma;

for preventing organ graft rejection;

for preventing complications in conditions in which vasospasms lead to vasoconstriction and thus tissue-ischemia or tissue-death (necrosis).

35) Therefore, a particular object of this invention is the use of a compound of formula I as defined in one of embodiments 1) to 31) above, or of a pharmaceutically acceptable salt thereof, for the manufacture of a medicament for the uses listed in embodiment 34) above, and for the manufacture of a medicament for the treatment of occlusive vascular disorders in general.

36) More generally, the invention relates to the use of a compound of formula I as defined in one of embodiments 1) to 31) above, or of a pharmaceutically acceptable salt thereof, for the manufacture of a medicament for the treatment and/or prevention of occlusive vascular disorders as well as to the use of a compound of formula I for the manufacture of a medicament for the treatment and/or prevention of peripheral vascular, of visceral-, hepatic- and renal-vascular, of cardiovascular and of cerebrovascular diseases or conditions associated with platelet aggregation, including thrombosis in humans and other mammals.

37) Among the above-mentioned uses of compounds of formula I or of pharmaceutically acceptable salts thereof for the manufacture of medicaments according to embodiment 35) above, the uses for manufacturing medicaments for the treatment or prophylaxis of myocardial infarction, arterial thrombosis (notably thrombotic stroke), transient ischaemic attacks, peripheral vascular disease and stable and unstable angina will be preferred.

38) The invention further relates to the use of a compound of formula I according to one of embodiments 1) to 31) above, or of a pharmaceutically acceptable salt thereof, for the preservation of blood products in vitro (e.g. the preservation of platelet concentrates), or for the prevention of occlusion in extra-corporeal blood or blood product treatment machines (such as renal dialysis machines or plasmapheresis machines).

39) The invention also relates to methods of treatment for the disorders mentioned in embodiment 34) above, said methods comprising the administration to a patient in need thereof of an effective amount of a compound of formula I according to one of embodiments 1) to 31), or of a pharmaceutically acceptable salt of such a compound.

The present invention also includes isotopically labelled, especially $^2$H (deuterium) labelled compounds of formula I, which compounds are identical to the compounds of formula I except that one or more atoms have each been replaced by an atom having the same atomic number but an atomic mass different from the atomic mass usually found in nature. Isotopically labelled, especially $^2$H (deuterium) labelled compounds of formula I and salts thereof are within the scope of the present invention. Substitution of hydrogen with the heavier isotope $^2$H (deuterium) may lead to greater metabolic stability, resulting e.g. in increased in-vivo half-life or reduced dosage requirements, or may lead to reduced inhibition of cytochrome P450 enzymes, resulting e.g. in an improved safety profile. In one embodiment of the invention, the compounds of formula I are not isotopically labelled, or they are labelled only with one or more deuterium atoms. In a sub-embodiment, the compounds of formula I are not isotopically labelled at all. Isotopically labelled compounds of formula I may be prepared in analogy to the methods described hereinafter, but using the appropriate isotopic variation of suitable reagents or starting materials.

Any reference to a compound of formula I, $I_P$ or $I_{STI}$ in this text is to be understood as referring also to the salts (and especially the pharmaceutically acceptable salts) of such compounds, as appropriate and expedient. The preferences indicated for the compounds of formula I of course apply mutatis mutandis to the compounds of formula $I_P$ and to the compounds of formula $I_{STI}$, as well as to the salts and pharmaceutically acceptable salts of the compounds of formula I, of formula $I_P$ or of formula $I_{STI}$. The same applies to these compounds as medicaments, to pharmaceutical compositions containing these compounds as active principles or to the uses of these compounds for the manufacture of a medicament for the treatment of the diseases according to this invention.

Preparation of the Compounds of Formula I
Abbreviations:

The following abbreviations are used throughout the specification and the examples:
Ac acetyl
ADP adenosine diphosphate
anh. anhydrous
aq. aqueous
Boc tert-butoxycarbonyl
BSA bovine serum albumin
Bu butyl
Cbz benzyloxycarbonyl
CC column chromatography
CV column volume
DIPEA diisopropylethylamine
DME 1,2-dimethoxyethane
DMF N,N-dimethylformamide
DMPU N,N'-dimethylpropyleneurea
DMSO dimethyl sulfoxide
dpm decays per minute
EDCI N-(3-dimethylaminopropyl)-N'-ethylcarbodiimide
EDTA ethylenediaminetetraacetic acid
Et ethyl
EtOAc ethyl acetate
eq. equivalent
HATU 2-(7-aza-1H-benzotriazole-1-yl)-1,1,3,3-tetramethyluronium hexafluorophosphate
Hept heptane
HOBT 1-hydroxybenzotriazole
HPLC High-performance liquid chromatography
HV high vacuum
iPr isopropyl
LC-MS Liquid Chromatography Mass Spectrometry
MCPBA meta-chloroperbenzoic acid
Me methyl
NBS N-bromosuccinimide
NMP N-methylpyrrolidone
org. organic
Pd/C palladium on carbon
Ph phenyl
PyBOP benzotriazole-1-yl-oxy-tris-pyrrolidino-phosphonium hexafluorophosphate
RT room temperature
sat. saturated
SDS sodium dodecyl sulfate
TBAF tetrabutylammonium fluoride
TBTU N,N,N',N'-Tetramethyl-O-(benzotriazol-1-yl)uronium tetrafluoroborate
TEMPO 2,2,6,6-tetramethylpiperidine-1-oxyl
TFA trifluoroacetic acid
THF tetrahydrofuran
TLC thin layer chromatography
$t_R$ retention time
Tris tris(hydroxymethyl)aminomethane General Preparation Routes (Part I):

A further aspect of the invention is a process for the preparation of compounds of formula (I). Compounds of formula (I) of the present invention can be prepared according to the general sequence of reactions outlined in the schemes below wherein G1, G2, W, Y, Z, $R^1$, $R^2$, $R^3$, $R^4$, $R^5$, $R^6$, $R^7$, $R^8$ and $R^9$ are as defined for formula (I). The compounds obtained may also be converted into pharmaceutically acceptable salts thereof in a manner known per se.

In general, all chemical transformations can be performed according to well-known standard methodologies as described in the literature or as described in the procedures below or in the experimental part. It is to be understood that any chiral starting material used in any procedure described below may also be used in enantiopure form.

The various compounds of formula I, wherein W represents the group G1, can be for instance prepared using the general routes summarized in Scheme 1 hereafter.

The compounds of formula I.1 can be obtained by hydrolysis of the corresponding compounds of formula II wherein Z' is —COOR$^5$ either under basic conditions using standard reagents such as NaOH or LiOH in a mixture of water and a suitable organic solvent such as THF, MeOH or EtOH, or under acidic conditions using standard reagents such as TFA in a suitable organic solvent such as $CH_2Cl_2$.

The compounds of formula I.2 can be prepared by treating the compounds of formula II wherein Z' is —P(O)(OR$^6$)$_2$, wherein R$^6$ represents ($C_1$-$C_4$)alkyl, with HCl optionally in the presence of $H_2O$, in a suitable organic solvent such as THF, EtOAc, dioxane or $Et_2O$ and preferably at a temperature around RT, or with trimethylsilyl bromide or trimethylsilyl iodide in a suitable solvent such as $CH_2Cl_2$ or $CH_3CN$ and preferably at a temperature around RT. Compounds of formula I, wherein Z represents phenyl, wherein the phenyl is substituted with P(O)(OH)$_2$, can be prepared from compounds of formula II, wherein Z' is phenyl, wherein the phenyl is substituted with P(O)(OR$^8$)$_2$ in analogy to the compounds of formula I.2.

The compounds of formula I.3, wherein R$^6$ represents ($C_1$-$C_4$)alkyl-C(O)—OCH$_2$— or ($C_1$-$C_4$)alkoxy-C(O)—OCH$_2$—, can be prepared by the reaction between a phosphonic acid of formula I.2 and an appropriate compound of formula ($C_1$-$C_4$)alkyl-C(O)—OCH$_2$—X or ($C_1$-$C_4$)alkoxy-C(O)—OCH$_2$—X, X being a leaving group such as chloride, bromide or iodide, in the presence of a suitable base (e.g. NEt$_3$, DIPEA) in a suitable solvent such as DMF, NMP or DMPU, optionally in the presence of NaI and preferably at a temperature between 45 and 90° C.

The compounds of formula I.4 can be prepared by the reaction between a phosphonic acid of formula I.2 and an appropriate amino acid alkyl ester (preferably an α-amino acid alkyl ester) of formula ($C_1$-$C_4$)alkoxy-C(O)—($C_1$-$C_4$)alkyl-NH$_2$ in the presence of a suitable base (e.g. NEt$_3$) and an activating mixture of reagents such as a combination of 2,2'-dipyridyl disulfide and PPh$_3$ in a suitable solvent such as anhydrous pyridine and preferably at a temperature of about 60° C.

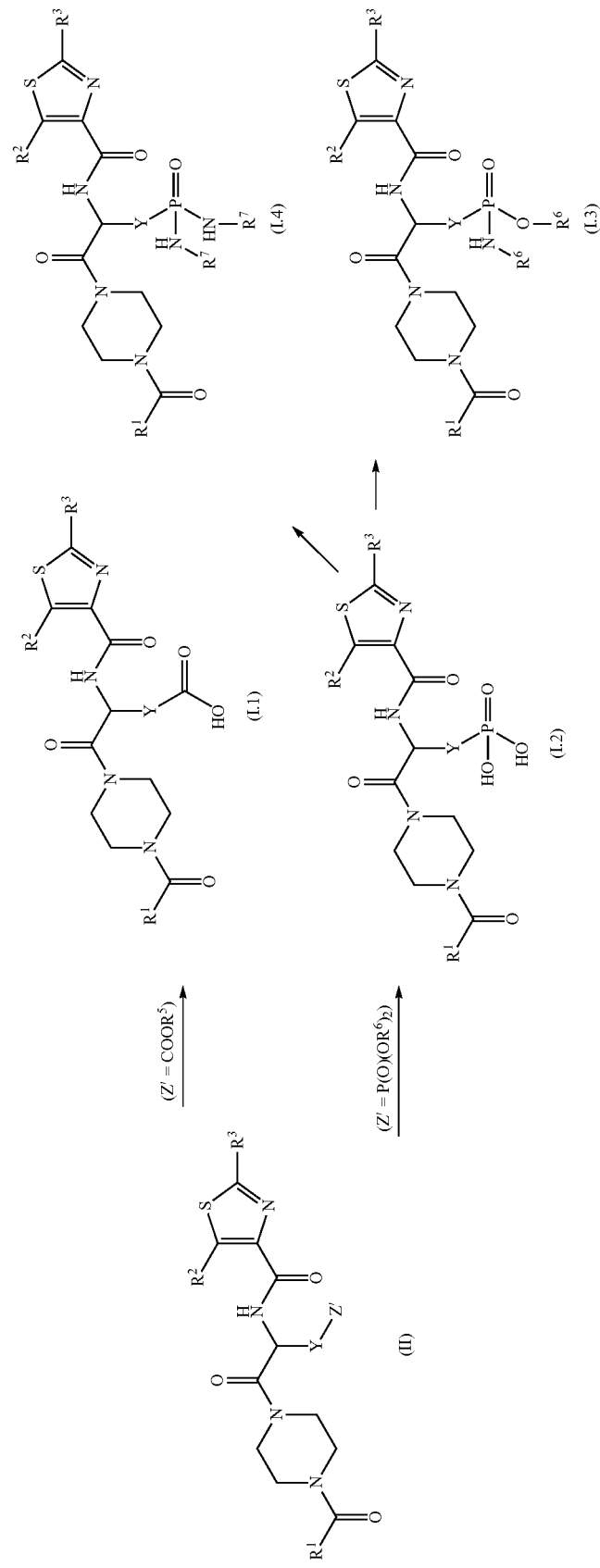

Furthermore, the compounds of formula I or II, wherein $R^2$ represents $(C_2-C_4)$alkenyl which is monosubstituted with $(C_1-C_4)$alkoxy, —COOH or —COOR$^9$, can be hydrogenated to lead to the compounds of formula I or II, wherein $R^2$ represents $(C_2-C_4)$alkyl which is monosubstituted with $(C_1-C_4)$alkoxy, —COOH or —COOR$^9$, using standard conditions for the hydrogenation of a double bond such as palladium on charcoal in a suitable solvent such as EtOH or MeOH, at a temperature preferably around RT and under hydrogen.

In addition, the compounds of formula I or II wherein $R^2$ contains a carboxylic ester function can lead to compounds of formula I or II wherein $R^2$ contains an carboxylic acid function by hydrolysis of the ester, using standard conditions as those already described above.

Compounds of formula I, which are also compounds of formula II, wherein

Y represents a bond and Z' represents hydrogen; or

Y represents $(C_1-C_3)$alkandiyl and Z' represents hydrogen, hydroxy, —COOR$^5$, —P(O)(OR$^6$)$_2$ [R$^6$ being $(C_1-C_4)$alkyl] or phenyl, wherein the phenyl is substituted with —P(O)(OR$^8$)$_2$, can be prepared according to Scheme 2, Scheme 2a or Scheme 2b below.

Preparation of the Compounds of Formula II

The compounds of formula II wherein $R^2$ represents $R^a$, $R^a$ being hydrogen or halogen (notably hydrogen, chlorine or bromine) can be prepared (Scheme 2) by coupling a compound of formula III with a compound of formula IV wherein $R^a$ represents hydrogen or halogen (notably hydrogen, chlorine or bromine) using standard peptide coupling reagents such as TBTU, HOBT, EDCI hydrochloride, HATU, PyBOP, in the presence of a suitable base such as NEt$_3$ or DIPEA and in a suitable solvent such as CH$_2$Cl$_2$, THF or DMF, preferably at a temperature around RT.

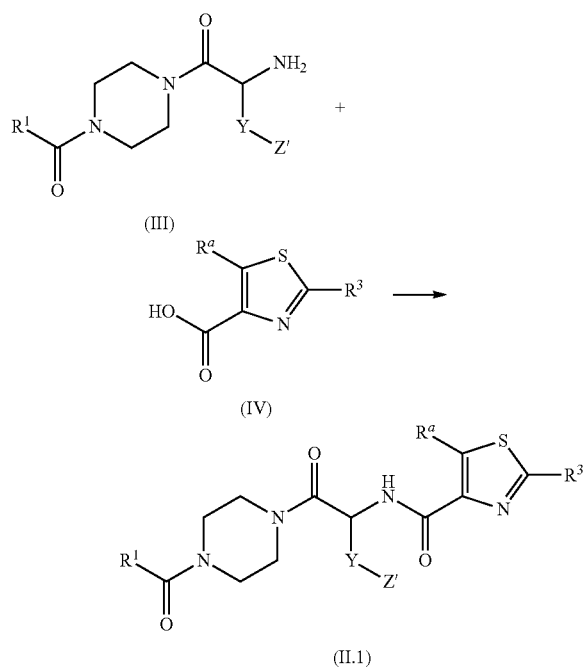

Scheme 2

The compounds of formula II wherein $R^2$ is different from hydrogen or halogen can be prepared from compounds of formula II.1, wherein $R^a$ represents bromine, using the general route summarized in Scheme 2a hereafter.

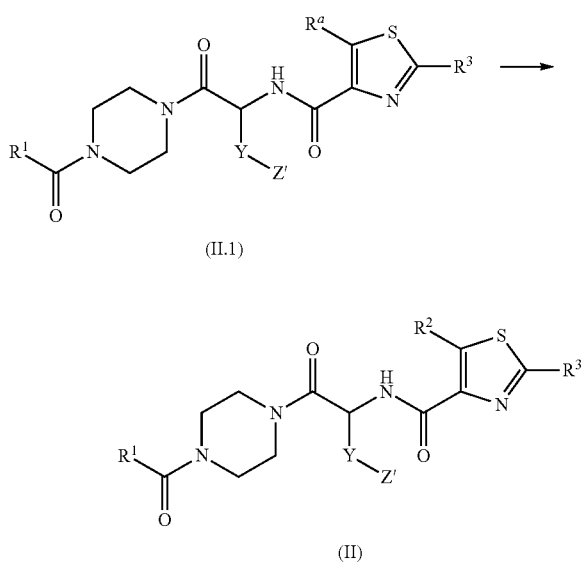

Scheme 2a

The compounds of formula II.1 can be converted into compounds of formula II wherein $R^2$ is an amino group by aromatic substitution reaction with the respective amine in the presence of a suitable base such as cesium carbonate, optionally in a suitable solvent such as THF or CH$_3$CN and preferably heating between 60° C. and 80° C.; said amino groups are defined by di-$(C_1-C_4)$alkyl-amino; or heterocyclyl which is unsubstituted or monosubstituted with $(C_1-C_4)$alkyl or $(C_1-C_4)$alkoxy. Alternatively, compounds of formula II, wherein $R^2$ represents $(C_1-C_4)$alkyl-amino wherein the alkyl group is monosubstituted with hydroxy or $(C_1-C_4)$alkoxy, can be obtained by heating compounds of formula II.1, wherein $R^a$ represents bromine, at a temperature of around 80 to 120° C. in the respective amine as solvent. Compounds of formula II, wherein $R^2$ represents $(C_1-C_4)$alkyl-amino wherein the alkyl group is monosubstituted with —COOH, can be prepared from the respective primary alcohols (obtained as described above) by oxidation using conditions known to one skilled in the art such as diacetoxyiodobenzene and TEMPO in a solvent mixture like water/CH$_3$CN. The obtained carboxylic acids can be transferred to the respective esters in an acid-catalyzed esterification.

The intermediates of formula II.1, wherein $R^a$ represents bromine, can furthermore be converted into compounds of formula II, wherein $R^2$ represents $(C_2-C_4)$alkenyl which is monosubstituted with $(C_1-C_4)$alkoxy or —COOR$^9$; or phenyl which is unsubstituted or monosubstituted with halogen, using a reagent of formula $R^2$—B(OR$^b$)$_2$, wherein OR$^b$ represents hydroxy or $(C_1-C_4)$alkoxy or the group B(OR$^b$)$_2$ represents a dioxaborolane ring which ring is unsubstituted or substituted with up to four methyl groups. The reaction is performed using standard conditions for a Suzuki reaction, and preferably with a boronic acid or ester derivative as mentioned above in the presence of a suitable base such as K$_2$CO$_3$, in the presence of a suitable palladium catalyst such as Pd(PPh$_3$)$_4$, in a suitable solvent such as a DME, dioxane/H$_2$O, EtOH/toluene/H$_2$O or CH$_3$CN/H$_2$O mixture, and preferably heating between 80° C. and 100° C. Besides, the intermediate of formula II.1 can also be converted into a compound of formula II wherein R$^2$ represents for instance 2-methoxymethyl-cycloprop-1-yl using a reagent of formula R$^2$—SnBu$_3$, using standard conditions for a Stille reaction, and preferably a tributylstannyl derivative, in presence of a suitable catalyst such as tetrakis(triphenylphosphine)palladium in a suitable solvent such as toluene, and preferably heating at about 120° C.

Alternatively, the compounds of formula II, wherein R$^2$ represents hydrogen, can be prepared (Scheme 2b) from intermediates of formula II.2, wherein R$^2$ represents hydrogen, using a reagent of formula R$^3$—B(OR$^b$)$_2$, wherein B(OR$^b$)$_2$ has the meaning as defined above, using standard conditions for a Suzuki reaction, and preferably a boronic acid derivative as mentioned above in the presence of a suitable base such as Na$_2$CO$_3$, in the presence of a suitable palladium catalyst such as Pd(PPh$_3$)$_4$, in a suitable solvent such as a toluene/EtOH mixture, and preferably heating around 75° C.

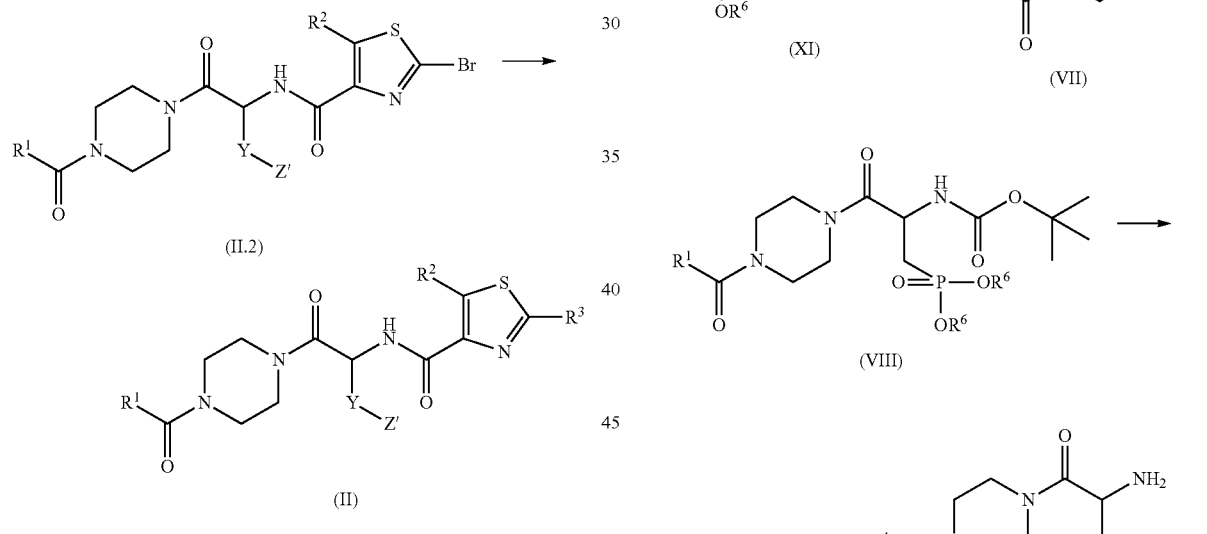

Compounds of formula II.2 can be prepared in analogy to compounds of formula II.1 as described for Scheme 2 using 2-bromo-thiazole-4-carboxylic acid which is commercially available.

Preparation of the Compounds of Formula III

The compounds of formula III, wherein Y represents a bond and Z' represents hydrogen; or Y represents (C$_1$-C$_3$) alkandiyl and Z' represents hydrogen, hydroxy, —COOH or —COOR$^5$ can be prepared using the route described in WO06114774 (preparation of compounds of formula III, Scheme 3).

The compounds of formula III wherein Y represents —CH$_2$— and Z' is —P(O)(OR$^6$)$_2$, R$^6$ being (C$_1$-C$_4$)alkyl and preferably ethyl, can be prepared using the route summarized in Scheme 3 hereafter.

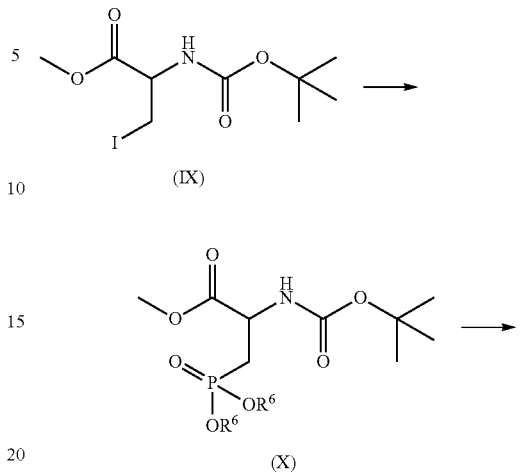

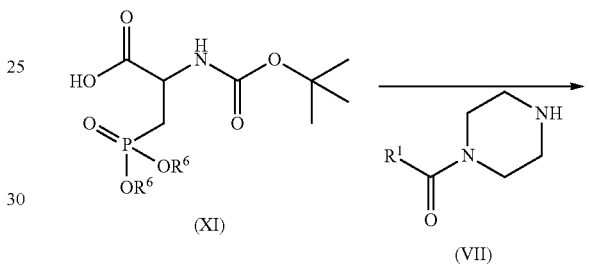

The compounds of formula VIII can be obtained in three steps starting from commercially available Boc-3-iodo-Ala-OMe IX in an Arbuzov reaction e.g. using P(OR$^6$)$_3$, R$^6$ being (C$_1$-C$_4$)alkyl and preferably ethyl, at reflux to give compound X followed by a saponification reaction using standard basic conditions such as those already described for Scheme 1 to give XI, which finally is coupled with a compound of formula VII using standard peptide coupling methods such as those described for the synthesis of compounds of formula II (see Scheme 2). The compounds of formula III.1 can then be obtained by standard acidic conditions for the removal of a Boc group that are well known to one skilled in the art. The compounds of formula VII can be prepared using the route described in WO06114774 (preparation of the compounds of formula V, Schemes 5 and 5a).

The compounds of formula III wherein Y represents —CH$_2$— and Z' represents phenyl, wherein the phenyl is substituted with —P(O)(OR$^8$)$_2$ can be prepared using the route summarized in Scheme 3a hereafter.

The Boc protected iodophenylalanine derivatives (XII), if not commercially available, can be prepared starting from the iodophenylalanine compounds using standard conditions for Boc protections known to one skilled in the art. The compounds XII thus obtained can then be coupled with compounds of formula VII using conditions already described in Scheme 3. The iodinated intermediates XIII can be converted into the phosphonic ester derivatives XIV using HP(O)(OR$^8$)$_2$ (preferably HP(O)(OEt)$_2$), in the presence of a suitable base such as NEt$_3$ and of a suitable palladium catalyst such as Pd(PPh$_3$)$_4$, in a suitable solvent such as CH$_3$CN or toluene, and preferably heating around reflux temperature. The compounds of formula III.2 can then be obtained by standard acidic conditions for the removal of a Boc group that are well known to one skilled in the art.

The compounds of formula III wherein Y represents —CH$_2$—CH$_2$— can be prepared using the route summarized in Scheme 3b hereafter.

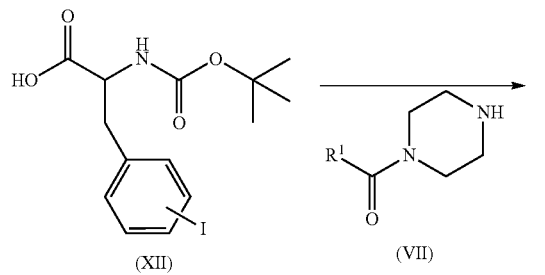

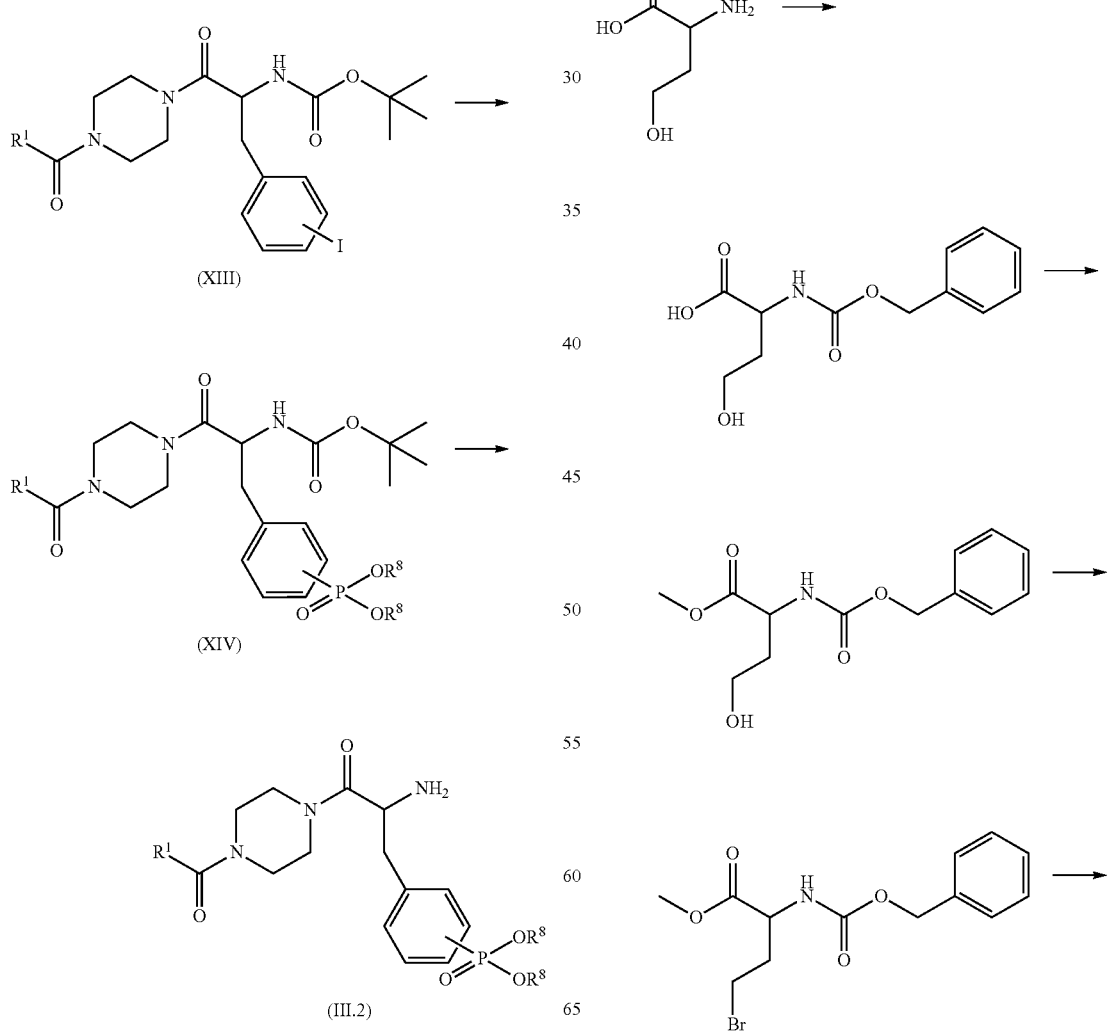

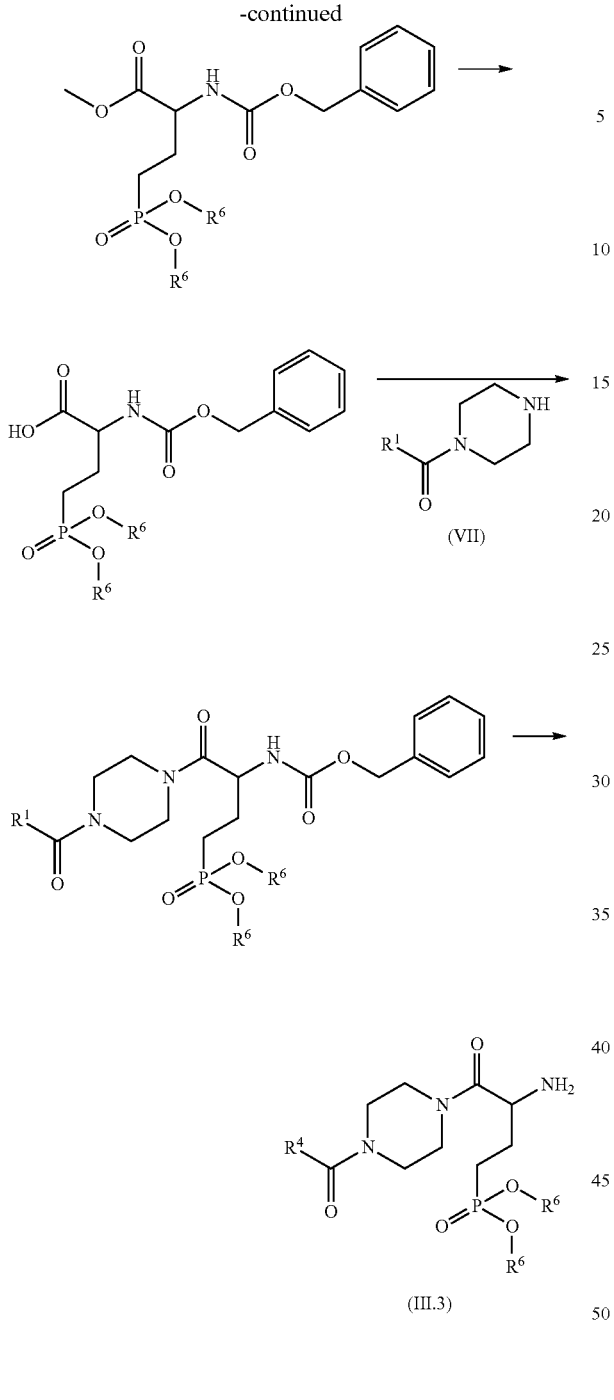

(VII)

(III.3)

Homoserine is first protected on the nitrogen atom with a Cbz group using standard conditions known to one skilled in the art (e.g. Cbz-Cl, aq. NaOH in dioxane). The dicyclohexylamine salt of the obtained molecule is prepared and the methyl ester is formed using MeI in DMF at a temperature around RT. The hydroxy function is then substituted by a bromide using standard conditions such as PPh₃ and CBr₄, in a suitable solvent such as CH₂Cl₂, preferably between 0° C. and RT. The next three steps are performed using conditions such as those already described for the synthesis of the compounds of formula VIII (see Scheme 3). The compounds of formula III.3 can then be obtained by cleaving the Cbz protecting group using standard conditions known to one skilled in the art (e.g. hydrogen, Pd/C in MeOH).

The compounds of formula III wherein Y represents —CH₂—CH₂—CH₂— can be prepared using the route summarized in Scheme 3c hereafter.

Scheme 3c

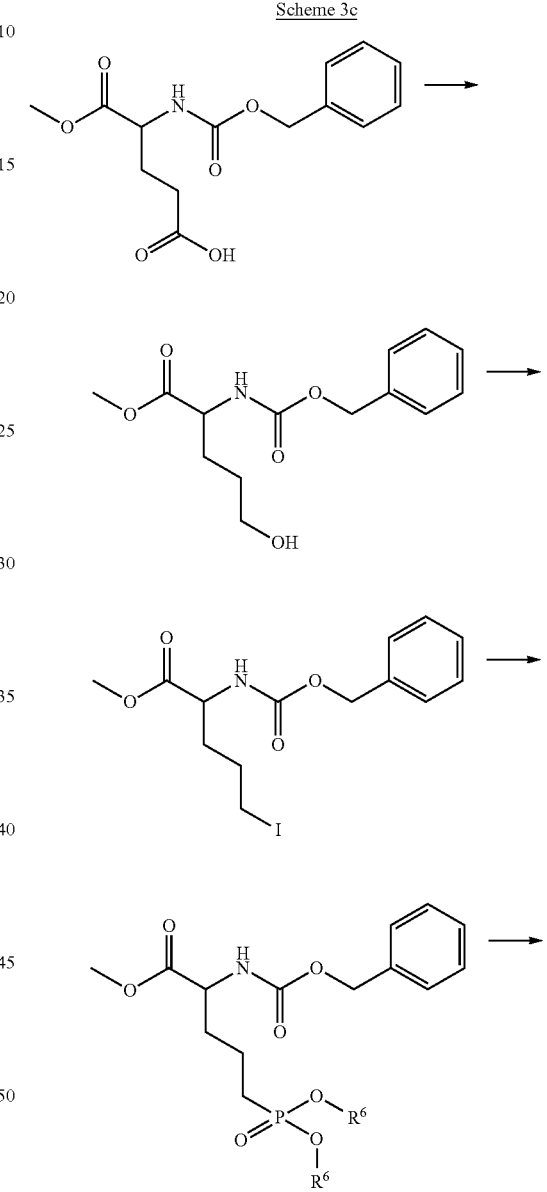

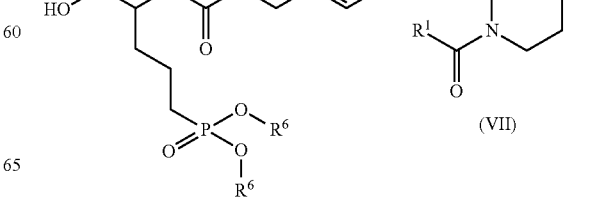

(VII)

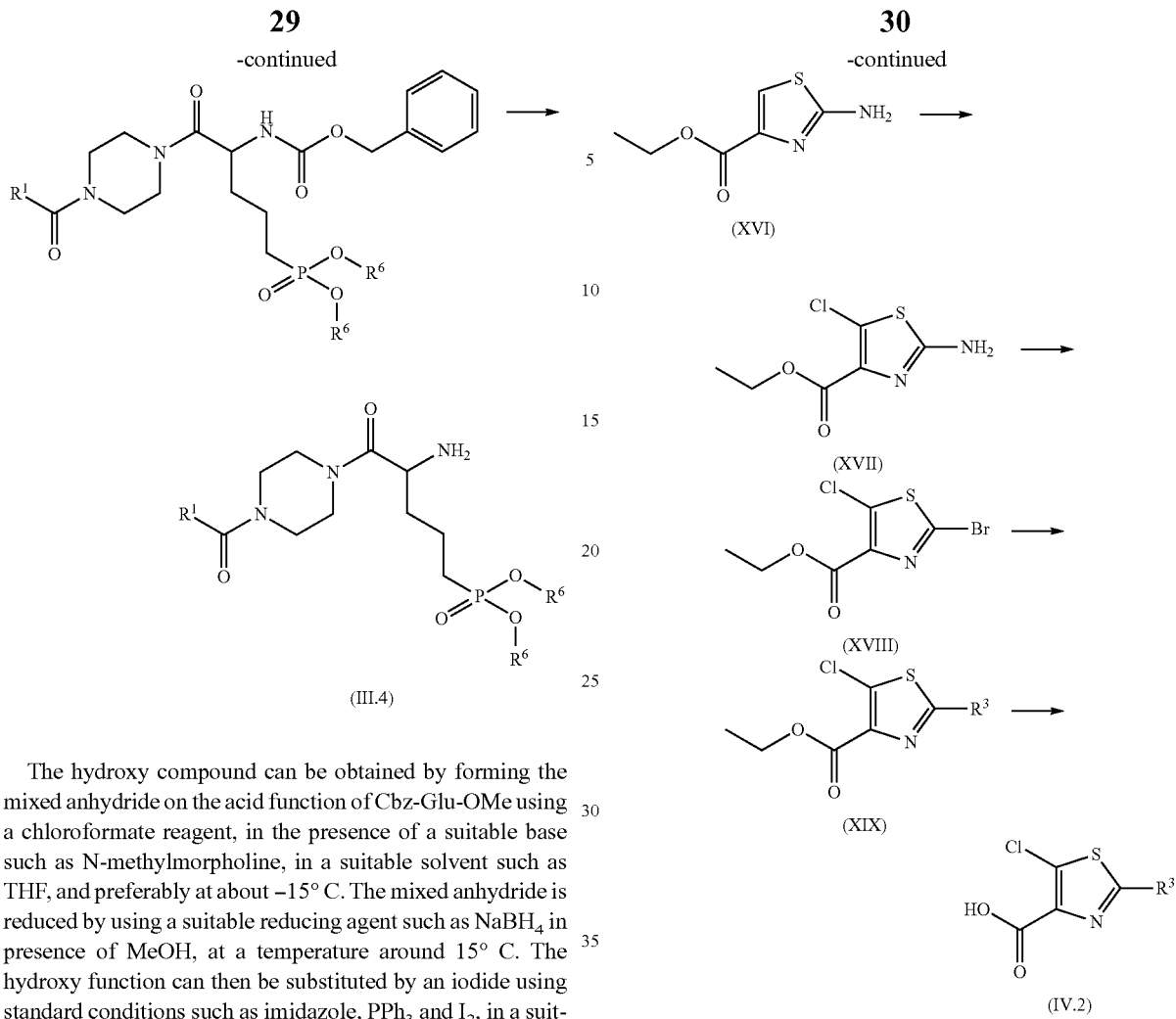

The hydroxy compound can be obtained by forming the mixed anhydride on the acid function of Cbz-Glu-OMe using a chloroformate reagent, in the presence of a suitable base such as N-methylmorpholine, in a suitable solvent such as THF, and preferably at about −15° C. The mixed anhydride is reduced by using a suitable reducing agent such as $NaBH_4$ in presence of MeOH, at a temperature around 15° C. The hydroxy function can then be substituted by an iodide using standard conditions such as imidazole, $PPh_3$ and $I_2$, in a suitable solvent such as THF, preferably between 0° C. and RT. The next three steps can be performed using conditions such as those already described for the synthesis of the compounds of formula VIII (see Scheme 3). The compounds of formula III.4 can then be obtained by standard conditions for the removal of a Cbz group that are well known to one skilled in the art (e.g. hydrogen, Pd/C in MeOH).

Preparation of the Compounds of Formula IV

The compounds of formula IV wherein $R^a$ represents halogen (notably chlorine or bromine) can be prepared using the route summarized in Scheme 4 hereafter. For $R^a$ representing bromine, direct bromination of commercially available compounds XV using a base such as n-BuLi and a brominating agent such as NBS in a solvent like THF, preferably at a temperature around −78° C. gives access to compounds IV.1.

Scheme 4

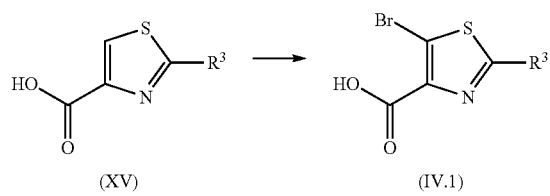

The compounds of formula IV.2 can be synthesized by chlorination of compound XVI using a chlorinating agent such as N-chlorosuccinimide in a solvent like $CH_3CN$. The conversion to the brominated intermediate XVIII can be achieved through a $CuBr_2$-mediated reaction in a solvent like $CH_3CN$ in the presence of e.g. isopentyl nitrite at a temperature of around 65° C. Compounds of formula XIX can be prepared from the bromide XVIII using a reagent of formula $R^3$—$B(OR^b)_2$, wherein $OR^b$ represents hydroxy or ($C_1$-$C_4$) alkoxy or the group $B(OR^b)_2$ represents a dioxaborolane ring which ring is unsubstituted or substituted with up to four methyl groups. The reaction may be performed using standard conditions for a Suzuki reaction, and preferably with a boronic acid or ester derivative as mentioned above in the presence of a suitable base such as $K_2CO_3$, in the presence of a suitable palladium catalyst such as $Pd(PPh_3)_4$, in a suitable solvent such as a $DME/H_2O$ mixture, and preferably heating between RT and 80° C. The compounds of formula IV.2 can be prepared by saponification of the compounds of formula XIX using standard basic conditions such as those already described for Scheme 1.

General Preparation Routes (Part II):

The various compounds of formula I, wherein W represents the group G2, can be for instance prepared using the general routes summarized in Scheme 5 hereafter.

Scheme 5
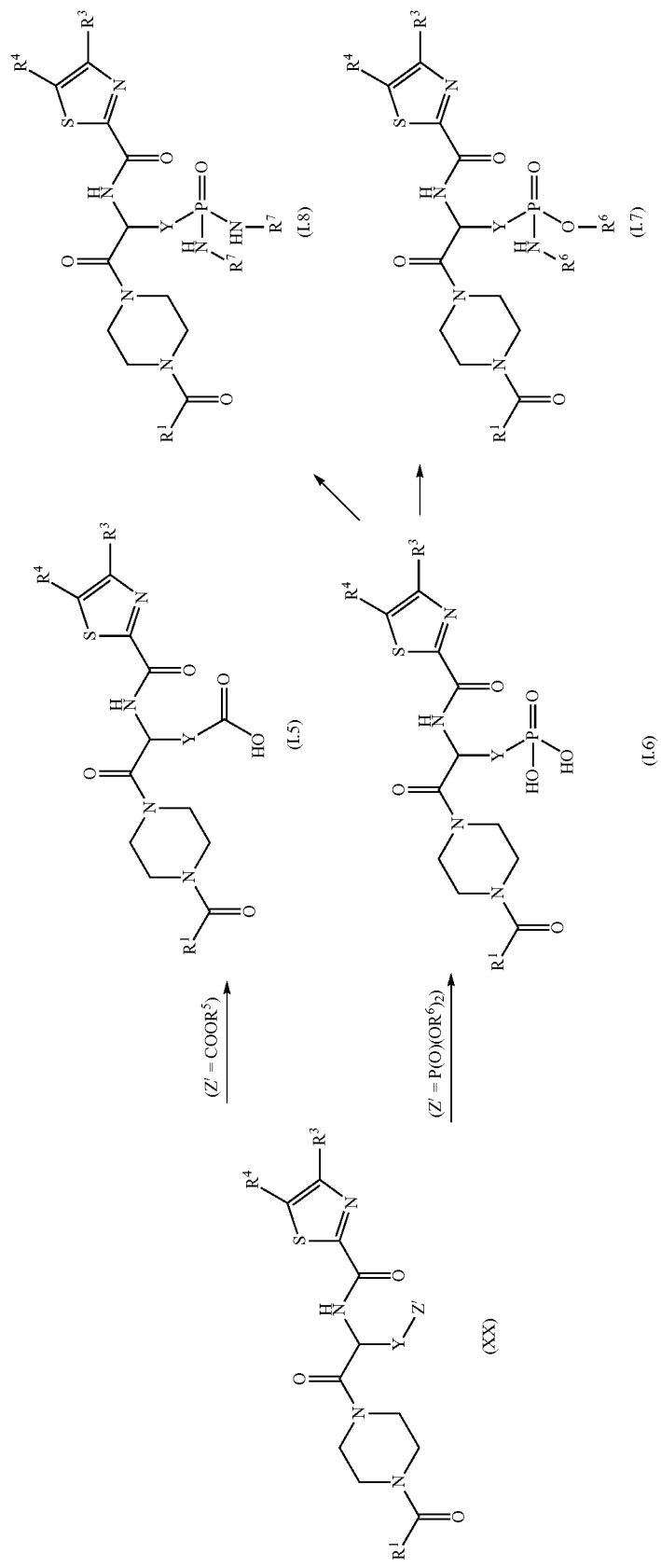

Compounds of formula I.5 to I.8 can be prepared from compounds of formula XX in analogy to compounds of formula I.1 to I.4 as described in Scheme 1 and in the general preparation routes (Part I).

Preparation of the Compounds of Formula XX

The compounds of formula XX (Scheme 6) can be prepared through amide coupling followed by aromatic substitution or metal-catalyzed cross-coupling reactions using conditions analogous to those already described for Scheme 2a.

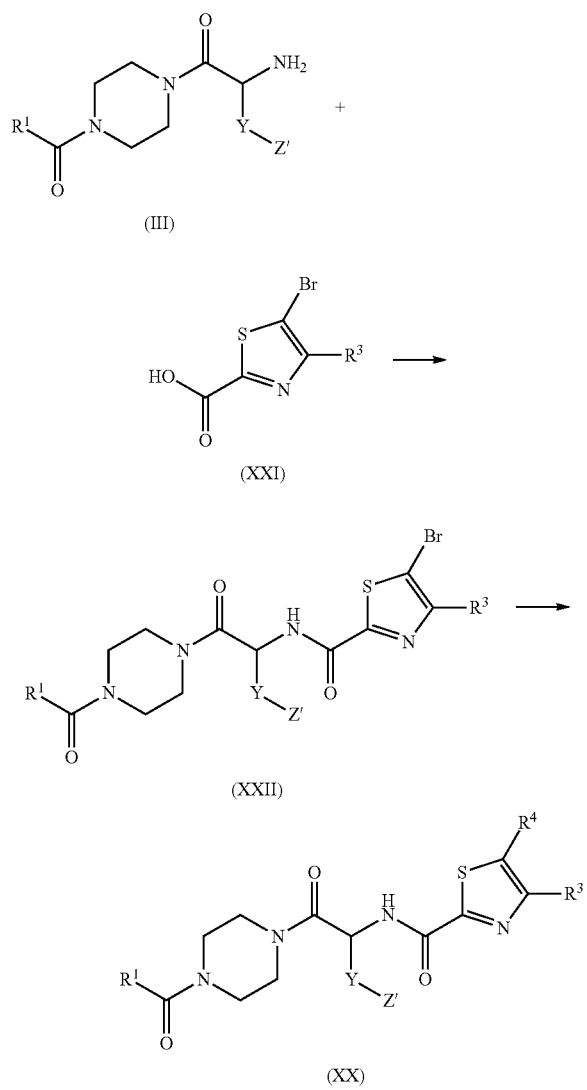

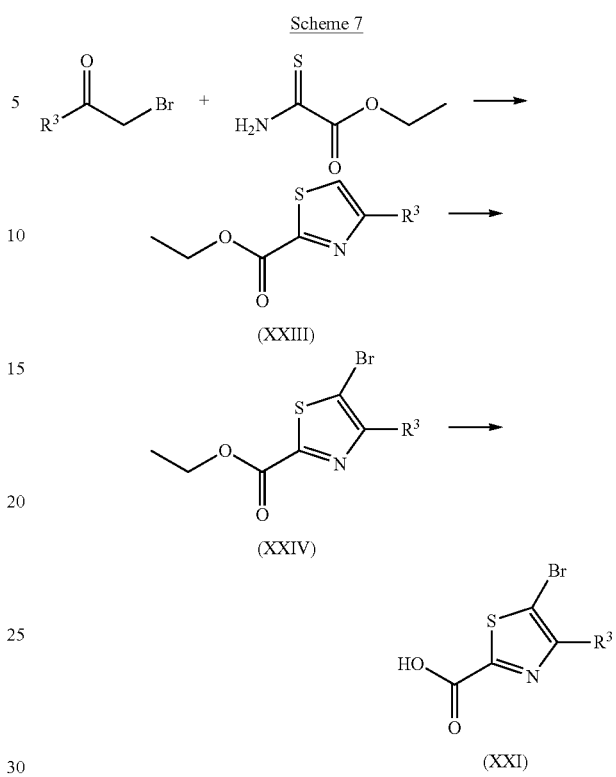

Preparation of the Compounds of Formula XXI

Compounds of formula XXIII ($R^3$=aryl) can be prepared (Scheme 7) by condensation of ethyl thiooxamate and a phenacylbromide derivative and heating around reflux in a solvent such as dioxane. Subsequently, the compounds of formula XXIV can be prepared by bromination of XXIII using NBS in a solvent like AcOH and at a temperature around 65° C. Saponification of XXIV using standard conditions like e.g. aq. KOH in MeOH at around 60° C. gives the acid derivatives XXI.

Whenever the compounds of formula (I) are obtained in the form of mixtures of enantiomers, the enantiomers can be separated using methods known to one skilled in the art: e.g. by formation and separation of diastereomeric salts or by HPLC over a chiral stationary phase such as a Regis Whelk-O1(R,R) (10 μm) column, a Daicel ChiralCel OD-H (5-10 μm) column, or a Daicel ChiralPak IA (10 μm) or AD-H (5 μm) column Typical conditions of chiral HPLC are an isocratic mixture of eluent A (EtOH, in presence or absence of an amine such as triethylamine or diethylamine) and eluent B (hexane), at a flow rate of 0.8 to 150 mL/min Particular embodiments of the invention are described in the following Examples, which serve to illustrate the invention in more detail without limiting its scope in any way.

EXAMPLES

Compounds are characterized by:
$^1$H-NMR (300 MHz, 400 MHz) (Varian/Bruker; chemical shifts are given in ppm relative to the solvent used; multiplicities: s=singlet, d=doublet, t=triplet, q=quartet, m=multiplet, br=broad, coupling constants are given in Hz).
Optical rotation was measured on a Jasco P-1030 polarimeter.
LC-MS: Thermo Finnigan MSQ or Dionex MSQPlus with HP 1100 Binary Pump and DAD, column: 4.6×50 mm, Zorbax SB-AQ, 5 μm, gradient: 5-95% $CH_3CN$ in $H_2O$, runtime: 1.45 min, with 0.04% TFA, flow: 4.5 mL/min. LC-MS marked with * refer to an LC run under basic conditions: Waters XBridge C18 5 μm, 4.6×50 mm with a gradient of 5-95% $CH_3CN$ in $H_2O$, runtime: 1.45 min, with 13 mM of $NH_4OH$, flow: 4.5 mL/min.
Compounds are purified by preparative HPLC using following methods/columns:

I) Phenomenex® column (Gemini 10 u C18 110 A Ax 50×21.2 mm); eluent: solvent A=$H_2O$+1% $HCO_2H$; solvent B=$CH_3CN$+1% $HCO_2H$; flow: 50 mL/min; The characteristics of the eluting mixture proportion in function of the time t from start of the elution are summarized in the tables below (a linear gradient being used between two consecutive time points):

| t (min) | 0 | 0.4 | 2.6 | 3 | 3.4 | 3.8 | 3.9 | 5 |
|---|---|---|---|---|---|---|---|---|
| Solvent A (%) | 75.1 | 75.1 | 55.1 | 55.1 | 4.5 | 4.5 | 75.1 | 75.1 |
| Solvent B (%) | 24.9 | 24.9 | 44.9 | 44.9 | 95.5 | 95.5 | 24.9 | 24.9 |

II) As I), with following gradient:

| t (min) | 0 | 0.6 | 3.3 | 3.9 | 4.5 | 5.1 | 5.2 | 6 |
|---|---|---|---|---|---|---|---|---|
| Solvent A (%) | 58 | 58 | 31.6 | 31.6 | 0 | 0 | 58 | 58 |
| Solvent B (%) | 42 | 42 | 68.4 | 68.4 | 100 | 100 | 42 | 42 |

III) Phenomenex® column (Luna C18 10 u 22.5×5 cm); eluent: solvent A=$H_2O$+0.5% $HCO_2H$; solvent B=$CH_3CN$+0.5% $HCO_2H$; flow: 50 mL/min;

| t (min) | 0 | 0.6 | 4.1 | 4.8 | 5.1 | 5.3 |
|---|---|---|---|---|---|---|
| Solvent A (%) | 80 | 80 | 5 | 5 | 80 | 80 |
| Solvent B (%) | 20 | 20 | 95 | 95 | 20 | 20 |

IV) XTerra RP18 (30×19 mm), 5 μm, gradient: 10-95% $CH_3CN$ in $H_2O$ with 0.5% $NH_4OH$ (25%)
V) XBridge C18 (50×19 mm), 5 μm, gradient: 10-95% $CH_3CN$ in $H_2O$ with 0.5% $NH_4OH$ (25%)
VI) As IV), but with a 5-95% gradient
VII) XBridge C18 (75×30 mm), 5 μm, gradient: 10-95% $CH_3CN$ in $H_2O$ with 0.5% $NH_4OH$ (25%)
VIII) XBridge C18 (30×19 mm), 5 μm, gradient: 10-95% $CH_3CN$ in $H_2O$ with 0.5% $NH_4OH$ (25%)
IX) Phenomenex® column (Luna C18 10 u 30×7.5 cm); eluent: solvent A=$H_2O$+0.5% $HCO_2H$; solvent B=$CH_3CN$+0.5% $HCO_2H$; flow: 100 mL/min;

| t (min) | 0 | 0.6 | 5.85 | 6.0 | 7.3 | 7.5 |
|---|---|---|---|---|---|---|
| Solvent A (%) | 60 | 60 | 5 | 5 | 60 | 60 |
| Solvent B (%) | 40 | 40 | 95 | 95 | 40 | 40 |

Stationary Phases Used for CC:
The purifications by CC have been performed using silica gel unless otherwise specified.

Example 1

4-{2-[(2-Phenyl-thiazole-4-carbonyl)-amino]-acetyl}-piperazine-1-carboxylic acid ethyl ester To a solution of 2-phenyl-1,3-thiazole-4-carboxylic acid (5.1 mg) and DIPEA (3 eq) in DMF (0.4 mL) was added TBTU (1.2 eq) in DMF (0.2 mL). Then, a solution of 4-(2-amino-acetyl)-piperazine-1-carboxylic acid ethyl ester (5.4 mg, prepared as described in WO2006114774) in DMF (0.2 mL) was added. After stirring overnight at RT, the reaction mixture was directly purified by preparative HPLC (IV) to give 4.9 mg of the desired product.
LC-MS*: $t_R$=0.82 min; [M+H]$^+$: 403.01.

Example 2

4-{(S)-4-Carboxy-2-[(2-phenyl-thiazole-4-carbonyl)-amino]-butyryl}-piperazine-1-carboxylic acid ethyl ester 2.1. 4-((S)-2-Amino-4-carboxy-butyryl)-piperazine-1-carboxylic acid ethyl ester trifluoroacetate salt To a solution of 4-((S)-2-amino-4-tert-butoxycarbonyl-butyryl)-piperazine-1-carboxylic acid ethyl ester (0.8 g, prepared as described in WO2006114774) in $CH_2Cl_2$ (15 mL) was added TFA (15 mL) and the reaction mixture stirred for 2 h at RT. The solution was evaporated to dryness to give 0.9 g of the desired product as clear oil.
LC-MS: $t_R$=0.50 min; [M+H]$^+$: 288.09.

2.2. 4-{(S)-4-Carboxy-2-[(2-phenyl-thiazole-4-carbonyl)-amino]-butyryl}-piperazine-1-carboxylic acid ethyl ester To a solution of 2-phenyl-1,3-thiazole-4-carboxylic acid (5.1 mg) and DIPEA (3 eq) in DMF (0.5 mL) was added TBTU (1.2 eq) in DMF (0.2 mL). Then, a solution of intermediate 2.1 (7.2 mg) in DMF (0.2 mL) was added. After stirring overnight at RT, 10 eq of aq. NaOH (2M) were added and the reaction mixture heated for 3 h at 55° C. The mixture was directly purified by preparative HPLC (VI) to give 5.7 mg of the desired product.
LC-MS*: $t_R$=0.59 min; [M+H]$^+$: 474.74.

Example 3

4-((S)-4-Carboxy-2-{[2-(2-phenoxy-phenyl)-thiazole-4-carbonyl]-amino}-butyryl)-piperazine-1-carboxylic acid butyl ester 3.1. (S)-2-tert-Butoxycarbonylamino-pentanedioic acid 5-ethyl ester To a solution of L-glutamic acid 5-ethyl ester (26.45 g) in dioxane (300 mL) was added sat. aq. $NaHCO_3$ (200 mL), followed by $Boc_2O$ (34.6 g), and the reaction mixture was stirred overnight at RT. The reaction mixture was acidified with an ice-cold aq. citric acid solution (5%), and the aq phase extracted with EtOAc (4×100 mL). The combined org. layers were washed with brine (2×), dried over $MgSO_4$ and evaporated to give 45.8 g of the crude product, which was used without further purification.
LC-MS*: $t_R$=0.54 min;

3.2. 4-((S)-2-tert-Butoxycarbonylamino-4-ethoxycarbonyl-butyryl)-piperazine-1-carboxylic acid butyl ester To a solution of intermediate 3.1 (8.75 g) in $CH_2Cl_2$ (50 mL)/THF (20 mL) was added HOBT (4.94 g). After 15 min, was added EDCI-HCl (6.70 g) and the reaction mixture further stirred for 20 min. Piperazine-1-carboxylic acid butyl ester (6.22 g, prepared as described in WO2008044217) was added and the reaction mixture stirred until reaction completion at RT. The mixture was poured onto an ice-cold aq. citric acid solution (5%), and the precipitate filtered off. The filtrate was extracted with Et$_2$O (3×200 mL), the org. phase washed with aq. citric acid (5%, 4×50 mL), sat. aq. Na$_2$CO$_3$ solution and brine. The combined org. layers were dried over MgSO$_4$ and evaporated to give 13.0 g of the desired product.
LC-MS: t$_R$=1.01 min; [M+H]$^+$: 444.49.

3.3. 4-((S)-2-Amino-4-ethoxycarbonyl-butyryl)-piperazine-1-carboxylic acid butyl ester hydrochloride salt To a solution of intermediate 3.2 (13 g) in iPrOH (50 mL) was added HCl in dioxane (4M, 15 mL) and the reaction mixture stirred at 50° C. until completion. The mixture was evaporated to dryness and the oily residue taken up in toluene and evaporated again to give 10.8 g of the desired product as a white solid.
LC-MS: t$_R$=0.74 min; [M+H]$^+$: 344.41.

3.4 4-{(S)-2-[(2-Bromo-thiazole-4-carbonyl)-amino]-4-ethoxycarbonyl-butyryl}-piperazine-1-carboxylic acid butyl ester This compound was prepared using a method analogous to that of Example 1, 2-bromo-thiazole-4-carboxylic acid replacing 2-phenyl-1,3-thiazole-4-carboxylic acid and intermediate 3.3 replacing 4-(2-amino-acetyl)-piperazine-1-carboxylic acid ethyl ester. Preparative HPLC (VII) gave the desired product.
LC-MS*: t$_R$=0.90 min; [M+H]$^+$: 532.82.

3.5. 4-((S)-4-Carboxy-2-{[2-(2-phenoxy-phenyl)-thiazole-4-carbonyl]-amino}-butyryl)-piperazine-1-carboxylic acid butyl ester Intermediate 3.4 (15.2 mg) and 2-phenoxyphenylboronic acid (6.4 mg, 1.2 eq) were dissolved at 40° C. in a degassed mixture of EtOH/toluene (0.5 mL, 1:1) and aq. Na$_2$CO$_3$ (2M, 0.35 mL). Next, [Pd(PPh$_3$)$_4$] (0.05 eq) was added and the reaction mixture heated to 75° C. for 18 h. After cooling to RT, the crude product was subjected to saponification with aq. LiOH (2M, 0.3 mL) for 3 h at RT. The reaction mixture was directly purified by preparative HPLC (V) to give 15.9 mg of the desired product.
LC-MS*: t$_R$=0.70 min; [M+H]$^+$: 594.87.

Example 4

4-((S)-4-Carboxy-2-{[2-(3-methoxy-phenyl)-thiazole-4-carbonyl]-amino}-butyryl)-piperazine-1-carboxylic acid butyl ester This compound was prepared using a method analogous to that of Example 3, step 3.5, 3-methoxyphenylboronic acid replacing 2-phenoxyphenylboronic acid.
LC-MS*: t$_R$=0.64 min; [M+H]$^+$: 532.78.

Example 5

4-((S)-4-Carboxy-2-{[2-(2-methoxy-phenyl)-thiazole-4-carbonyl]-amino}-butyryl)-piperazine-1-carboxylic acid butyl ester This compound was prepared using a method analogous to that of Example 3, step 3.5, 2-methoxyphenylboronic acid replacing 2-phenoxyphenylboronic acid.
LC-MS*: t$_R$=0.65 min; [M+H]$^+$: 532.91.

Example 6

4-{(S)-4-Carboxy-2-[(2-o-tolyl-thiazole-4-carbonyl)-amino]-butyryl}-piperazine-1-carboxylic acid butyl ester This compound was prepared using a method analogous to that of Example 3, step 3.5, 2-methylphenylboronic acid replacing 2-phenoxyphenylboronic acid.
LC-MS*: t$_R$=0.66 min; [M+H]$^+$: 516.89.

Example 7

4-{(S)-4-Carboxy-2-[(2-phenyl-thiazole-4-carbonyl)-amino]-butyryl}-piperazine-1-carboxylic acid butyl ester To a solution of 2-phenyl-1,3-thiazole-4-carboxylic acid (163 mg) in DMF (1 mL) and DIPEA (0.31 mL) was added TBTU (216 mg), followed by intermediate 3.3 (210 mg) in CH$_3$CN solution (1 mL). After completion of the amide coupling were added to the reaction mixture LiOH (2M, 0.3 mL) and DMSO (0.25 mL). After 1 h at RT the crude product was directly purified by preparative HPLC (VIII). The product-containing fractions were concentrated in vacuo, the residue dilute with H$_2$O and extracted with CH$_2$Cl$_2$ (3×50 mL), dried over MgSO$_4$ and evaporated to give 120 mg of the desired product as a yellowish foam.
LC-MS: t$_R$=0.97 min; [M+H]$^+$: 503.40.

Example 8

4-{(R)-3-(Diethoxy-phosphoryl)-2-[(2-phenyl-thiazole-4-carbonyl)-amino]-propionyl}-piperazine-1-carboxylic acid butyl ester

8.1. (R)-2-tert-butoxycarbonylamino-3-(diethoxy-phosphoryl)-propionic acid methyl ester Boc-3-iodo-L-Ala-OMe (9.4 g) was dissolved in triethyl phosphite (100 mL). The mixture was heated at 130° C. overnight and evaporated to dryness to give a yellow oil (8.37 g). The compound was used in the next step without further purification.
LC-MS: t$_R$=0.85 min; [M+H]$^+$: 340.09.

8.2. (R)-2-tert-butoxycarbonylamino-3-(diethoxy-phosphoryl)-propionic acid

An aq. solution of lithium hydroxide hydrate (2.07 g in 5 mL) was added to a solution of intermediate 8.1 (8.37 g) in THF (99 mL). The reaction mixture was stirred at RT overnight and CH$_2$Cl$_2$ and an aq. HCl solution (1M, 60 mL) was added. The phases were separated and the aq. phase was extracted with CH$_2$Cl$_2$ (3×). The org. phases were combined, dried (Na$_2$SO$_4$) and evaporated off to give 5.8 g of the desired product as a white powder.
LC-MS: t$_R$=0.77 min; [M+H]$^+$: 326.13.

8.3. 4-[(R)-2-tert-Butoxycarbonylamino-3-(diethoxy-phosphoryl)-propionyl]-piperazine-1-carboxylic acid butyl ester To a solution of intermediate 8.2 (7.37 g) in CH$_2$Cl$_2$ (95 mL), THF (24 mL) and DIPEA (16.3 mL) were added HOBT (3.83 g) and EDCI-HCl (4.78 g), and the reaction mixture was stirred at RT for 10 min. Subsequently, piperazine-1-carboxylic acid butyl ester (5.31 g) was added and the mixture stirred at RT for 2.5 h. The reaction mixture was diluted with $CH_2Cl_2$, the org. phase washed with sat. aq. $NaHCO_3$ and the aq. phase re-extracted with $CH_2Cl_2$. The combined org. phases were washed with brine, dried over $Na_2SO_4$, and concentrated to dryness. Purification by CC (EtOAc/MeOH 1:0 to 9:1) gave 7.66 g of the desired product.

LC-MS: $t_R$=0.94 min; $[M+H]^+$: 494.00.

8.4 4-[(R)-2-Amino-3-(diethoxy-phosphoryl)-propionyl]-piperazine-1-carboxylic acid butyl ester hydrochloride salt To a solution of intermediate 8.3 (7.66 g) in EtOAc (7.75 mL) was added HCl (15.5 mL, 4M in dioxane) and the reaction mixture stirred at RT until reaction completion. The mixture was concentrated to dryness and the residue dried overnight to give 6.59 g of the desired product, which was used without further purification.

LC-MS: $t_R$=0.73 min; $[M+H]^+$: 394.43.

8.5. 4-{(R)-3-(Diethoxy-phosphoryl)-2-[(2-phenyl-thiazole-4-carbonyl)-amino]-propionyl}-piperazine-1-carboxylic acid butyl ester To a solution of intermediate 8.4 (500 mg) in $CH_2Cl_2$ (3 mL), THF (0.9 mL) and DIPEA (0.8 mL) was added 2-phenyl-1,3-thiazole-4-carboxylic acid (231.2 mg) followed by HATU (1070.9 mg) and the reaction mixture was stirred at RT until reaction completion. The reaction mixture was diluted with $CH_2Cl_2$, washed with 1M aq. $NaHSO_4$ (2×5 mL). and the aq. layers were extracted with $CH_2Cl_2$ (1×). The combined org. layers were washed with brine, dried over $MgSO_4$ evaporated to dryness. CC (EtOAc/Hept 1:1, then $CH_2Cl_2$/MeOH 9:1) gave 495 mg of the desired product.

LC-MS: $t_R$=1.00 min; $[M+H]^+$: 581.56.

Example 9

4-{(R)-2-[(2-Phenyl-thiazole-4-carbonyl)-amino]-3-phosphono-propionyl}-piperazine-1-carboxylic acid butyl ester To a solution of intermediate 8.5 (424 mg) in $CH_3CN$ (14 mL) was added at 0° C. TMSBr (1.9 mL) and the mixture stirred at RT until completion of the reaction. $H_2O$ was added and the mixture further stirred up to 60 min. The org. solvent was evaporated and the aq. layer extracted with EtOAc (2×). The combined org. layers were evaporated to give 193 mg of the desired product. A pure analytical sample was obtained by purification with preparative HPLC (I).

LC-MS: $t_R$=0.85 min; $[M+H]^+$: 525.17.

Example 10

4-{(S)-3-[4-(Diethoxy-phosphoryl)-phenyl]-2-[(2-phenyl-thiazole-4-carbonyl)-amino]-propionyl}-piperazine-1-carboxylic acid butyl ester

10.1. 4-[(S)-2-tert-Butoxycarbonylamino-3-(4-iodo-phenyl)-propionyl]-piperazine-1-carboxylic acid butyl ester This compound was prepared using a method analogous to that of Example 8, step 8.5 Boc-Phe(4-I)-OH replacing 2-phenoxyphenylboronic acid and piperazine-1-carboxylic acid butyl ester replacing intermediate 8.4.

LC-MS: $t_R$=1.11 min; $[M+H]^+$: 560.45.

10.2. 4-{2-tert-Butoxycarbonylamino-3-[4-(diethoxy-phosphoryl)-phenyl]propionyl}-piperazine-1-carboxylic acid butyl ester To a solution of intermediate 10.1 (6.16 g) in $CH_3CN$ (120 mL) was added $[Pd(PPh_3)_4]$ (1.31 g) followed by $Et_3N$ (3.08 mL) and diethyl phosphite (2.15 mL). After heating the resulting suspension overnight at reflux under argon, the reaction mixture was allowed to cool down to RT and evaporated. The residue was taken up in EtOAc (100 mL) and washed with citric acid 10% (60 mL), aq. sat. $NaHCO_3$ (60 mL), $H_2O$ (60 mL) and brine (60 mL). The org. phase was dried over $MgSO_4$, filtrated off over celite, and the filtrate evaporated. The crude mixture was purified three times with CC($CH_2Cl_2$/[$CH_2Cl_2$/MeOH 8:2] 95:5 to 75:25) to give 4.21 g of the desired product.

LC-MS: $t_R$=1.00 min; $[M+H]^+$: 570.65.

10.3. 4-{(S)-2-Amino-3-[4-(diethoxy-phosphoryl)-phenyl]-propionyl}-piperazine-1-carboxylic acid butyl ester This compound was prepared using a method analogous to that of Example 8, step 8.3, intermediate 10.2 replacing intermediate 8.3. The crude was purified by CC (eluent: $CH_2Cl_2$/MeOH+0.1% $NEt_3$ 18:1 then 9:1) to give 3.9 g of the desired product as a pale yellow foam.

LC-MS: $t_R$=0.75 min; $[M+H]^+$: 470.54.

10.4. 4-{(S)-3-[4-(Diethoxy-phosphoryl)-phenyl]-2-[(2-phenyl-thiazole-4-carbonyl)-amino]-propionyl}-piperazine-1-carboxylic acid butyl ester This compound was prepared using a method analogous to that of Example 8, step 8.3, intermediate 10.3 replacing intermediate 8.4 and using preparative HPLC (II) instead of CC.

LC-MS: $t_R$=1.07 min; $[M+H]^+$: 657.10.

Example 11

4-[(S)-2-[(2-Phenyl-thiazole-4-carbonyl)-amino]-3-(4-phosphono-phenyl)-propionyl]-piperazine-1-carboxylic acid butyl ester This compound was prepared using a method analogous to that of Example 9, intermediate 10.4 replacing intermediate 8.5.

LC-MS: $t_R$=0.91 min; $[M+H]^+$: 601.63.

Example 12

4-{(S)-3-[4-(Diethoxy-phosphoryl)-phenyl]-2-[(2-phenyl-thiazole-4-carbonyl)-amino]-propionyl}-piperazine-1-carboxylic acid ethyl ester

12.1. 4-[(S)-2-tert-Butoxycarbonylamino-3-(4-iodo-phenyl)-propionyl]-piperazine-1-carboxylic acid ethyl ester This compound was prepared using a method analogous to that of Example 8, step 8.3, piperazine-1-carboxylic acid ethyl ester replacing piperazine-1-carboxylic acid butyl ester and Boc-Phe(4-I)-OH replacing intermediate 8.2.

LC-MS: $t_R$=1.04 min; $[M+H]^+$: 532.44.

12.2. 4-{(S)-2-tert-Butoxycarbonylamino-3-[4-(di-ethoxy-phosphoryl)-phenyl]-propionyl}-piperazine-1-carboxylic acid ethyl ester This compound was prepared using a method analogous to that of Example 10, step 10.2, intermediate 12.1 replacing intermediate 10.1.

LC-MS: $t_R$=0.94 min; [M+H]$^+$: 542.38.

12.3. 4-{(S)-2-Amino-3-[4-(diethoxy-phosphoryl)-phenyl]-propionyl}-piperazine-1-carboxylic acid ethyl ester hydrochloride salt This compound was prepared using a method analogous to that of Example 8, step 8.4, intermediate 12.2 replacing intermediate 8.3.

LC-MS: $t_R$=0.68 min; [M+H]$^+$: 442.34.

12.4. 4-{(S)-3-[4-(Diethoxy-phosphoryl)-phenyl]-2-[(2-phenyl-thiazole-4-carbonyl)-amino]-propionyl}-piperazine-1-carboxylic acid ethyl ester This compound was prepared using a method analogous to that of Example 8, step 8.3, intermediate 12.3 replacing intermediate 8.4 and using preparative HPLC (II) instead of CC.

LC-MS: $t_R$=1.01 min; [M+H]$^+$: 629.68.

Example 13

4-[(S)-2-[(2-Phenyl-thiazole-4-carbonyl)-amino]-3-(4-phosphono-phenyl)-propionyl]-piperazine-1-carboxylic acid ethyl ester This compound was prepared using a method analogous to that of Example 9, intermediate 12.4 replacing intermediate 8.5.

LC-MS: $t_R$=0.84 min; [M+H]$^+$: 573.51.

Example 14

4-{(S)-2-[(5-Bromo-2-phenyl-thiazole-4-carbonyl)-amino]-4-tert-butoxycarbonyl-butyryl}-piperazine-1-carboxylic acid butyl ester

14.1. 5-Bromo-2-phenyl-thiazole-4-carboxylic acid

To a solution of 2-phenyl-1,3-thiazole-4-carboxylic acid (3.2 g) in abs. THF (190 mL) was added at 78° C. over 10 min n-BuLi (25 mL, 1.6M in hexanes). After addition, Br$_2$ (1.3 mL) in cyclohexane (7.4 mL) was added over 10 min. The reaction mixture was allowed to warm up to RT and was stirred at this temperature for 3 h. The reaction mixture was then cooled to 0° C., carefully quenched with HCl (1M, 32 mL) and extracted with EtOAc (2×). The combined org. phases were washed with aq. sodium thiosulfate (20%), dried over MgSO$_4$ and evaporated to dryness to give 4.5 g of the desired product. The crude was used without further purification.

LC-MS: $t_R$=0.92 min; [M+H]$^+$: 284.09.

14.2. 4-((S)-2-Amino-4-tert-butoxycarbonyl-butyryl)-piperazine-1-carboxylic acid butyl ester A suspension of 4-((S)-2-benzyloxycarbonylamino-4-tert-butoxycarbonyl-butyryl)-piperazine-1-carboxylic acid butyl ester (4.00 g, prepared as described in WO2008050301) and Pd/C (5%, 0.42 g) in EtOH (15 mL) was hydrogenated at RT overnight. The reaction mixture was then stirred under H$_2$ overnight. The mixture was filtered through celite and evaporated off. HV drying afforded the desired compound as light brown oil (2.79 g).

LC-MS: $t_R$=0.79 min; [M+H]$^+$: 372.45.

14.3. 4-{(S)-2-[(5-Bromo-2-phenyl-thiazole-4-carbonyl)-amino]-4-tert-butoxycarbonyl-butyryl}-piperazine-1-carboxylic acid butyl ester This compound was prepared using a method analogous to that of Example 8, step 8.3, intermediate 14.1 replacing intermediate 8.2, intermediate 14.2 replacing piperazine-1-carboxylic acid butyl ester and using CH$_2$Cl$_2$ instead of CH$_2$Cl$_2$/THF. The compound was however purified by CC (EtOAc/Hept 0:1 to EtOAc/Hept 1:0).

LC-MS: $t_R$=1.17 min; [M+H]$^+$: 637.03.

Example 15

4-{(S)-2-[(5-Bromo-2-phenyl-thiazole-4-carbonyl)-amino]-4-carboxy-butyryl}-piperazine-1-carboxylic acid butyl ester To a solution of intermediate 14.3 (22.0 mg) in CH$_2$Cl$_2$ (0.25 mL) was added TFA (0.25 mL) and the reaction mixture stirred for 30 min at RT. The reaction mixture was diluted with toluene and evaporated to dryness. The residue was taken up in H$_2$O/sat. aq. NaHCO$_3$ and EtOAc and the aq. phase extracted with EtOAc (2×). The combined org. phases were dried over MgSO$_4$ and evaporated to dryness. Preparative HPLC (I) gave the desired product (10 mg) as yellow oil.

LC-MS: $t_R$=1.03 min; [M+H]$^+$: 581.09.

Example 16

4-{(S)-4-Carboxy-2-[(5-chloro-2-phenyl-thiazole-4-carbonyl)-amino]-butyryl}-piperazine-1-carboxylic acid butyl ester

16.1. 2-Amino-5-chloro-thiazole-4-carboxylic acid ethyl ester

To a solution of ethyl 2-aminothiazole-5-carboxylate (500.0 mg) in CH$_3$CN (6 mL) was added N-chlorosuccinimide (388 mg). The reaction mixture was stirred at 90° C. for 2.75 h Again, N-chlorosuccinimide (44.1 mg) was added and the reaction mixture stirred for further 2 h at reflux, and overnight at RT. The reaction mixture was cooled to 0° C., the precipitate filtrated and washed with cold iPrOH (2×12 mL). The HCl salt was taken up in H$_2$O (10 mL) and 1M NaOH, and the aq. phase extracted with CH$_2$Cl$_2$. The combined org. layers were dried over MgSO$_4$ and evaporated to dryness to give 635 mg of the desired product.

LC-MS: $t_R$=0.77 min; [M+H]$^+$: 207.40.

16.2. 2-Bromo-5-chloro-thiazole-4-carboxylic acid ethyl ester

To a suspension of CuBr$_2$ (250.8 mg) in CH$_3$CN (4 mL) was added at 5° C. isopentyl nitrite (0.23 mL). After stirring for 5 min was added in portions at 5° C. intermediate 16.1. ELN145-0048.2. (281.8 mg) and the reaction mixture was carefully heated to 65° C. for 1.5 h. The reaction mixture was evaporated to dryness, the residue diluted with H$_2$O and stirred at RT for 1 h. The precipitate was filtrated and washed with H$_2$O, CH$_2$Cl$_2$ (5×1.5 mL). The filtrate was evaporated, the residue taken up in Et$_2$O (4 mL) and stirred at RT overnight. The mixture was filtrated, taken up in Hept (1.5 mL), stirred for 1 h again, filtrated and evaporated to dryness to give 224 mg of the desired product.

$^1$H NMR δ, 4.46 (q, 2H), 1.44 (t, 3H).

16.3. 5-Chloro-2-phenyl-thiazole-4-carboxylic acid ethyl ester

To a solution of intermediate 16.2 (173 mg) in DME (1 mL) was added phenylboronic acid (67 mg), followed by [Pd(PPh$_3$)$_4$] (129 mg) and a solution of K$_2$CO$_3$ (80.0 mg) in H$_2$O (0.4 mL). The reaction mixture was heated at reflux for 2 h. The reaction mixture was allowed to cool down to RT and was extracted with EtOAc (3×). The combined org. layers were dried over MgSO$_4$ and evaporated to dryness. CC (EtOAc/Hept 0:1 to EtOAc/Hept 1:0) gave 93 mg of the desired product as yellowish oil.

LC-MS: $t_R$=1.07 min; [M+H]$^+$: 268.16.

16.4. 5-Chloro-2-phenyl-thiazole-4-carboxylic acid

To intermediate 16.3 (90 mg) in MeOH (1 mL) was added 1M NaOH (0.5 mL) and the reaction mixture was stirred at RT until reaction completion. The reaction mixture was acidified with 1N HCl, and the aq. phase extracted with EtOAc (3×). The combined org. layers were washed with brine, dried over MgSO$_4$, and evaporated to dryness to give 79 mg of the desired product.

LC-MS: $t_R$=0.90 min; [M+H]$^+$: 240.24.

16.5. 4-{(S)-4-tert-Butoxycarbonyl-2-[(5-chloro-2-phenyl-thiazole-4-carbonyl)-amino]-butyryl}-piperazine-1-carboxylic acid butyl ester This compound was prepared using a method analogous to that of Example 14, step 14.3, intermediate 16.4 replacing intermediate 14.1.

LC-MS: $t_R$=1.16 min; [M+H]$^+$: 595.11.

16.6. 4-{(S)-4-Carboxy-2-[(5-chloro-2-phenyl-thiazole-4-carbonyl)-amino]-butyryl}-piperazine-1-carboxylic acid butyl ester This compound was prepared using a method analogous to that of Example 15, intermediate 16.5 replacing intermediate 14.3. However, no preparative HPLC purification was done.

LC-MS: $t_R$=1.02 min; [M+H]$^+$: 537.23.

Example 17

4-{(S)-4-Carboxy-2-[(2,5-diphenyl-thiazole-4-carbonyl)-amino]-butyryl}-piperazine-1-carboxylic acid butyl ester

17.1. 4-{(S)-4-tert-Butoxycarbonyl-2-[(2,5-diphenyl-thiazole-4-carbonyl)-amino]-butyryl}-piperazine-1-carboxylic acid butyl ester To a mixture of intermediate 14.3 (51 mg) in DME (0.5 mL) was added phenylboronic acid (10 mg) followed by [Pd(PPh$_3$)$_4$] (19 mg) and by a solution of K$_2$CO$_3$ (12 mg) in H$_2$O (0.2 mL). The reaction mixture was stirred at 90° C. for 4 h. Phenylboronic acid (5.4 mg) was added again, and the mixture was stirred at 90° C. overnight. The reaction mixture was allowed to cool to RT, and was extracted with EtOAc (3×). The combined org. layers were dried over MgSO$_4$ and evaporated to dryness. CC (EtOAc/Hept 0:1 to EtOAc/Hept 1:0) gave 41 mg of the desired product as yellowish oil.

LC-MS: $t_R$=1.22 min; [M+H]$^+$: 635.48.

17.2. 4-{(S)-4-Carboxy-2-[(2,5-diphenyl-thiazole-4-carbonyl)-amino]-butyryl}-piperazine-1-carboxylic acid butyl ester To a solution of intermediate 17.1 (40 mg) in CH$_2$Cl$_2$ (0.45 mL) was added TFA (0.45 mL). After stirring for 1 h at RT, the reaction mixture was diluted with toluene and concentrated to dryness.

LC-MS: $t_R$=1.08 min; [M+H]$^+$: 579.45.

Example 18

4-((S)-4-Carboxy-2-{[5-((1S,2S)-2-methoxymethyl-cyclopropyl)-2-phenyl-thiazole-4-carbonyl]-amino}-butyryl)-piperazine-1-carboxylic acid butyl ester

18.1. (E)-3-tributylstannanyl-prop-2-en-1-ol

To neat propargyl alcohol (1.77 mL) were added tributyltin hydride (10.3 mL) followed by 1,1'-azobis(cyclohexanecarbonitrile) (378 mg). The mixture was heated for 2.5 h at 80° C., cooled to RT and directly purified by CC (EtOAc/Hept 5:95) to afford the desired compound (5.4 g).

$^1$H-NMR (CDCl$_3$): 6.22 (m, 2H); 4.20 (m, 2H); 1.57-1.28 (m, 18H); 0.92 (t, 9H).

18.2. ((1R,2S)-2-tributylstannanyl-cyclopropyl)-methanol

To a solution of DME (1.8 mL) in anh. CH$_2$Cl$_2$ (70 mL) cooled at −13° C. under argon was slowly added Et$_2$Zn (18.5 mL), followed by CH$_2$I$_2$ (3 mL) in CH$_2$Cl$_2$ (20 mL) over a 30 min period while keeping the internal temperature around −12.5° C. After completion of the addition, the resulting solution was stirred for 30 min at −10° C. A solution of (4R,5R)-2-butyl-N,N,N',N'-tetramethyl-1,3,2-dioxaborolane-4,5-dicarboxamide in CH$_2$Cl$_2$ (25 mL) was added slowly to keep internal temperature below −10° C., immediately followed by a solution of intermediate 18.1 (3.2 g) in CH$_2$Cl$_2$ (25 mL) dropwise (internal temperature between −10° C. and −8° C.). The cooling bath was removed, and the reaction mixture was allowed to warm to RT and was stirred overnight at RT. The reaction was quenched with an aq. NH$_4$Cl solution (10 mL), and a 1M aq. HCl solution (10 mL). The mixture was diluted with H$_2$O, the org. phase separated and the aq. phase was extracted with CH$_2$Cl$_2$ and Et$_2$O. The combined org. phases were dried over MgSO$_4$ and evaporated off. CC (Hept/EtOAc 100:0 to 95:5) gave 3.18 g of the desired compound.

$^1$H-NMR (CDCl$_3$): 3.55 (m, 1H); 3.39 (m, 1H); 1.54-1.44 (m, 6H); 1.36-1.24 (m, 6H); 1.14-1.03 (m, 1H); 0.90 (t, 9H); 0.83-0.78 (m, 6H); 0.75-0.69 (m, 1H); 0.55-0.50 (m, 2H); −0.20-−0.30 (m, 1H).

Optical rotation (589 nm, CHCl$_3$, 26.6° C., l=10 cm, 99.6 mg in 10 mL, c=1.0): specific optical rotation=+14.74.

18.3. Tributyl-((1S,2R)-2-methoxymethyl-cyclopropyl)-stannane

To a solution of intermediate 18.2 (9.5 g) in THF (200 mL) was added NaH (2.27 g, 60% in mineral oil) at RT, and the mixture stirred 30 min at RT. MeI (7.55 mL) was added and stirring was continued at RT overnight. The reaction mixture was diluted with H$_2$O and extracted with CH$_2$Cl$_2$. The combined org. phases were dried over MgSO$_4$ and evaporated off to afford the desired compound as pale yellow oil (10.49 g).
$^1$H-NMR (CDCl$_3$): 3.45 (dd, 1H); 3.38 (s, 3H); 3.12 (dd, 1H); 1.55-1.47 (m, 6H); 1.37-1.28 (m, 6H); 1.05 (m, 1H); 0.91 (t, 9H); 0.83 (m, 6H); 0.56 (m, 2H); −0.30 (m, 1H).

18.4. 4-((S)-4-tert-Butoxycarbonyl-2-{[5-((1S,2S)-2-methoxymethyl-cyclopropyl)-2-phenyl-thiazole-4-carbonyl]-amino}-butyryl)-piperazine-1-carboxylic acid butyl ester A degassed mixture of intermediate 14.3 (50 mg), intermediate 18.3 (30 mg) and [Pd(PPh$_3$)$_4$] (5.1 mg) in toluene (2.0 mL) was heated to reflux overnight. To drive the reaction to completion, intermediate 18.3 (13.4 mg and 30 mg after 40 h) and after 18 h [Pd(PPh$_3$)$_4$] (0.05 eq) were added. After 48 h at reflux the reaction mixture was evaporated and the crude mixture purified by CC (EtOAc/Hept 0:1 to EtOAc/Hept 1:0).
LC-MS: $t_R$=1.18 min; [M+H]$^+$: 643.13.

18.5. 4-((S)-4-Carboxy-2-{[5-((1S,2S)-2-methoxymethyl-cyclopropyl)-2-phenyl-thiazole-4-carbonyl]-amino}-butyryl)-piperazine-1-carboxylic acid butyl ester This compound was prepared using a method analogous to that of Example 17, intermediate 18.4 replacing intermediate 17.1. In addition, a preparative TLC purification (CH$_2$Cl$_2$/MeOH 9:1) was done.
LC-MS: $t_R$=1.04 min; [M+H]$^+$: 587.53.

Example 19

4-((S)-4-Carboxy-2-{[5-((E)-2-carboxy-vinyl)-2-phenyl-thiazole-4-carbonyl]-amino}-butyryl)-piperazine-1-carboxylic acid butyl ester To a mixture of Example 15 (152 mg) in dioxane (1.5 mL) was added 2-ethoxycarbonylvinylboronic acid pinacol ester (64 mg) followed by [Pd(PPh$_3$)$_4$] (32 mg) and a solution of K$_2$CO$_3$ (50 mg) in H$_2$O (1.0 mL) and the reaction mixture was stirred at 90° C. for 1.5 h. The crude mixture was evaporated and the residue taken up in EtOH (2 mL). LiOH (50 mg) in MeOH/H$_2$O (7:3, 1 mL) was added and the reaction mixture stirred at RT for 1 h. The reaction mixture was acidified to pH 3 with 1N HCl and extracted with CH$_2$Cl$_2$ (3×). The combined org. phase were evaporated to dryness and purified by CC (EtOAc, then CH$_2$Cl$_2$/MeOH 9:1) to give 91 mg of the desired product.
LC-MS: $t_R$=0.98 min; [M+H]$^+$: 573.29.

Example 20

4-((S)-4-Carboxy-2-{[5-(2-carboxy-ethyl)-2-phenyl-thiazole-4-carbonyl]-amino}-butyryl)-piperazine-1-carboxylic acid butyl ester A suspension of Example 19 (53 mg) and Pd/C (10%, 62 mg) in MeOH (2 mL) was stirred at RT under H$_2$ atmosphere until reaction completion. The reaction mixture was filtrated over celite and the filtrate evaporated to dryness. Preparative HPLC (I) gave 18 mg of the desired product as yellow foam.
LC-MS: $t_R$=0.96 min; [M+H]$^+$: 574.92.

Example 21

4-((S)-4-Carboxy-2-{[5-((E)-3-methoxy-propenyl)-2-phenyl-thiazole-4-carbonyl]-amino}-butyryl)-piperazine-1-carboxylic acid butyl ester 21.1. 4-((S)-4-tert-Butoxycarbonyl-2-{[5-((E)-3-methoxy-propenyl)-2-phenyl-thiazole-4-carbonyl]-amino}-butyryl)-carboxylic acid butyl ester This compound was prepared using a method analogous to that of Example 17, step 17.1, (E)-2-(3-methoxy-1-propen-1-yl)-4,4,5,5-tetramethyl-1,3,2-dioxaborolane replacing phenylboronic acid.
LC-MS: $t_R$=1.19 min; [M+H]$^+$: 629.96.

21.2. 4-((S)-4-Carboxy-2-{[5-((E)-3-methoxy-propenyl)-2-phenyl-thiazole-4-carbonyl]-amino}-butyryl)-piperazine-1-carboxylic acid butyl ester This compound was prepared using a method analogous to that of Example 17, step 17.1, intermediate 21.1 replacing intermediate 17.1. However, a preparative HPLC (I) purification was carried out instead of CC.
LC-MS: $t_R$=1.05 min; [M+H]$^+$: 573.39.

Example 22

4-((S)-4-Carboxy-2-{[5-(3-methoxy-propyl)-2-phenyl-thiazole-4-carbonyl]-amino}-butyryl)-piperazine-1-carboxylic acid butyl ester 22.1. 4-((S)-4-tert-Butoxycarbonyl-2-{[5-(3-methoxy-propyl)-2-phenyl-thiazole-4-carbonyl]-amino}-butyryl)-piperazine-1-carboxylic acid butyl ester A suspension of intermediate 21.1 (52 mg), Pd/C (10%, 44 mg) and DIPEA (0.05 mL) in MeOH (1.5 mL) was stirred at RT under H$_2$ atmosphere for 1 h. The reaction mixture was filtrated over celite and the filtrate evaporated to dryness. The desired compound (49 mg) was used without further purification.
LC-MS: $t_R$=1.18 min; [M+H]$^+$: 631.94.

22.2. 4-((S)-4-Carboxy-2-{[5-(3-methoxy-propyl)-2-phenyl-thiazole-4-carbonyl]-amino}-butyryl)-piperazine-1-carboxylic acid butyl ester This compound was prepared using a method analogous to that of Example 15, intermediate 22.1 replacing intermediate 14.3.
LC-MS: $t_R$=1.04 min; [M+H]$^+$: 575.11.

Example 23

4-{(S)-4-Carboxy-2-[(5-morpholin-4-yl-2-phenyl-thiazole-4-carbonyl)-amino]-butyryl}-piperazine-1-carboxylic acid butyl ester 23.1. 4-{(S)-4-tert-Butoxycarbonyl-2-[(5-morpholin-4-yl-2-phenyl-thiazole-4-carbonyl)-amino]-butyryl}-piperazine-1-carboxylic acid butyl ester To a solution of intermediate 14.3 in morpholine (0.7 mL) was added Cs$_2$CO$_3$ (36 mg), and the reaction mixture stirred at 60° C. overnight, and at 90° C. for additional 6 h. The reaction mixture was diluted with H$_2$O extracted with EtOAc (3×). The combined org. phases were dried over MgSO$_4$, filtrated, evaporated to dryness and used without further purification.
LC-MS: $t_R$=1.14 min; [M+H]$^+$: 644.43.

23.2. 4-{(S)-4-Carboxy-2-[(5-morpholin-4-yl-2-phenyl-thiazole-4-carbonyl)-amino]-butyryl}-piperazine-1-carboxylic acid butyl ester This compound was prepared using a method analogous to that of Example 17, intermediate 23.1 replacing intermediate 17.1. However, a preparative HPLC (I) purification was carried out instead of CC.
LC-MS: $t_R$=0.99 min; [M+H]$^+$: 588.66.

Example 24

4-{(S)-4-Carboxy-2-[(2-phenyl-5-pyrrolidin-1-yl-thiazole-4-carbonyl)-amino]-butyryl}-piperazine-1-carboxylic acid butyl ester

24.1. 4-{(S)-4-tert-Butoxycarbonyl-2-[(2-phenyl-5-pyrrolidin-1-yl-thiazole-4-carbonyl)-amino]-butyryl}-piperazine-1-carboxylic acid butyl ester This compound was prepared using a method analogous to that of Example 23, pyrrolidine replacing morpholine.
LC-MS: $t_R$=1.20 min; [M+H]$^+$: 628.95.

24.2. 4-{(S)-4-Carboxy-2-[(2-phenyl-5-pyrrolidin-1-yl-thiazole-4-carbonyl)-amino]-butyryl}-piperazine-1-carboxylic acid butyl ester This compound was prepared using a method analogous to that of Example 15, intermediate 24.1 replacing intermediate 14.3.
LC-MS: $t_R$=1.05 min; [M+H]$^+$: 572.51.

Example 25

4-((S)-4-Carboxy-2-{[5-((S)-3-methoxy-pyrrolidin-1-yl)-2-phenyl-thiazole-4-carbonyl]-amino}-butyryl)-piperazine-1-carboxylic acid butyl ester To a solution of Example 15 (50 mg) in CH$_3$CN (1 mL) was added (S)-3-methoxypyrrolidine hydrochloride (WO2008044217, 103 mg) and Cs$_2$CO$_3$ (70 mg), and the reaction mixture was stirred at 80° C. for 24 h. To the reaction mixture was added H$_2$O and EtOAc, the phases were separated and the aq. phase was extracted with EtOAc (2×). The org. phases were dried over MgSO$_4$, filtrated and evaporated to dryness. Preparative TLC (EtOAc+0.1% AcOH) gave 11 mg of the desired product.
LC-MS: $t_R$=1.02 min; [M+H]$^+$: 602.53.

Example 26

4-{2-[(2-Phenyl-thiazole-4-carbonyl)-amino]-acetyl}-piperazine-1-carboxylic acid butyl ester

26.1. 4-(2-tert-Butoxycarbonylamino-acetyl)-piperazine-1-carboxylic acid butyl ester This compound was prepared using a method analogous to that of Example 3, step 3.2, Boc-Glycine replacing intermediate 3.1 and using CH$_2$Cl$_2$ instead of CH$_2$Cl$_2$/THF.
LC-MS: $t_R$=0.92 min; [M+H]$^+$: 344.27.

26.2. 4-(2-Amino-acetyl)-piperazine-1-carboxylic acid butyl ester

To a solution of intermediate 26.1 (4620 mg) in CH$_2$Cl$_2$ (20 mL) was added TFA (20 mL). The reaction mixture was stirred at RT for 2 h and the solvents were evaporated off. The crude was redissolved in CH$_2$Cl$_2$ (20 mL) and washed with 1N NaOH and brine, dried (MgSO$_4$) and evaporated off to afford 3120 mg of the desired compound as yellowish oil.
LC-MS: $t_R$=0.63 min; [M+H]$^+$: 243.49.

26.3. 4-{2-[(2-Phenyl-thiazole-4-carbonyl)-amino]-acetyl}-piperazine-1-carboxylic acid butyl ester This compound was prepared using a method analogous to that of Example 3, step 3.2, 2-phenyl-1.3-thiazole-4-carboxylic acid replacing intermediate 3.1 and intermediate 26.2 replacing piperazine-1-carboxylic acid butyl ester.
LC-MS: $t_R$=1.03 min; [M+H]$^+$: 431.58.

Example 27

4-(2-{[5-(3-Hydroxy-propylamino)-2-phenyl-thiazole-4-carbonyl]-amino}-acetyl)-piperazine-1-carboxylic acid butyl ester

27.1. 4-{2-[(5-Bromo-2-phenyl-thiazole-4-carbonyl)-amino]-acetyl}-piperazine-1-carboxylic acid butyl ester This compound was prepared using a method analogous to that of Example 14, step 14.3, intermediate 26.3 replacing (S)-4-(2-Amino-4-tert-butoxycarbonyl-butyryl)-piperazine-1-carboxylic acid butyl ester.
LC-MS: $t_R$=1.08 min; [M+H]$^+$: 509.03.

27.2. 4-(2-{[5-(3-Hydroxy-propylamino)-2-phenyl-thiazole-4-carbonyl]-amino}-acetyl)-piperazine-1-carboxylic acid butyl ester Intermediate 27.1 (500 mg) was stirred in 3-aminopropanol (3 mL) at 120° C. for 1 h. The reaction mixture was allowed to cool to RT and was diluted with CH$_2$Cl$_2$. The org. phase was washed with HCl (1M, 3×) and brine. The org. phase was then dried over Na$_2$SO$_4$ and concentrated in vacuo. Purification by CC(CH$_2$Cl$_2$/MeOH 95:5) gave 285 mg of the desired product.
LC-MS: $t_R$=1.01 min; [M+H]$^+$: 504.45.

Example 28

4-(2-{[5-(3-Methoxy-propylamino)-2-phenyl-thiazole-4-carbonyl]-amino}-acetyl)-piperazine-1-carboxylic acid butyl ester This compound was prepared using a method analogous to that of Example 27, step 27.2, 3-methoxypropylamine replacing 3-aminopropanol. However, the reaction mixture was stirred at 80° C. overnight.
LC-MS: $t_R$=1.06 min; [M+H]$^+$: 518.21.

Example 29

4-(2-{[5-(3-Fluoro-phenyl)-2-phenyl-thiazole-4-carbonyl]-amino}-acetyl)-piperazine-1-carboxylic acid butyl ester A mixture of intermediate 27.1 (25 mg), 3-fluorophenylboronic acid (11 mg), [Pd(PPh$_3$)$_4$] (3 mg) in 1N NaHCO$_3$ (0.5 mL) and CH$_3$CN (0.5 mL) was heated to reflux overnight. The org. phase was separated, filtrated and directly purified by preparative HPLC (IV) to give 12 mg of the desired product.
LC-MS: $t_R$=1.15 min; [M+H]$^+$: 525.29.

Example 30

4-(2-{[5-((E)-2-Ethoxycarbonyl-vinyl)-2-phenyl-thiazole-4-carbonyl]-amino}-acetyl)-piperazine-1-carboxylic acid butyl ester To a mixture of intermediate 27.1 (300 mg) in DME (3 mL) was added 2-ethoxycarbonylvinylboronic acid pinacol ester (133 mg) followed by [Pd(PPh$_3$)$_4$] (34 mg) and a solution of K$_2$CO$_3$ (81 mg) in H$_2$O (1.5 mL). The flask was evacuated and backfilled with argon and the mixture was stirred at 90° C. for 40 h. To drive the reaction to completion the boronic ester (3×1 eq) was added at different interval, as well as an additional portion of cat. (1×0.05 eq). The reaction mixture was allowed to cool to RT and was extracted with EtOAc (3×). The combined org. layers were dried over MgSO$_4$ evaporated to dryness. Purification by CC (EtOAc/Hept 0:1 to EtOAc/Hept 7:3) followed by preparative HPLC (I) gave 66 mg of the desired product.
LC-MS: $t_R$=1.15 min; [M+H]$^+$: 529.35.

Example 31

4-(2-{[5-((E)-2-Carboxy-vinyl)-2-phenyl-thiazole-4-carbonyl]-amino}-acetyl)-piperazine-1-carboxylic acid butyl ester This compound was prepared using a method analogous to that of Example 28, Example 30 replacing intermediate 27.2. In addition, preparative TLC with CH$_2$Cl$_2$/MeOH 95:5+1% AcOH was carried out.
LC-MS: $t_R$=1.02 min; [M+H]$^+$: 501.30.

Example 32

4-(2-{[5-(2-Ethoxycarbonyl-ethyl)-2-phenyl-thiazole-4-carbonyl]-amino}-acetyl)-piperazine-1-carboxylic acid butyl ester This compound was prepared using a method analogous to that of Example 20, Example 30 replacing Example 19. Purification by preparative TLC (EtOAc/Hept 7:3) instead of preparative HPLC (I) was carried out.
LC-MS: $t_R$=1.10 min; [M+H]$^+$: 531.53.

Example 33

4-(2-{[5-(2-Carboxy-ethyl)-2-phenyl-thiazole-4-carbonyl]-amino}-acetyl)-piperazine-1-carboxylic acid butyl ester This compound was prepared using a method analogous to that of Example 28, Example 32 replacing intermediate 27.2.
LC-MS: $t_R$=0.99 min; [M+H]$^+$: 503.60.

Example 34

4-(2-{[5-(3-Methoxy-propenyl)-2-phenyl-thiazole-4-carbonyl]-amino}-acetyl)-piperazine-1-carboxylic acid butyl ester This compound was prepared using a method analogous to that of Example 16, step 16.3, intermediate 27.1 replacing intermediate 16.2, (E)-2-(3-methoxy-1-propen-1-yl)-4,4,5,5-tetramethyl-1,3,2-dioxaborolane replacing phenylboronic acid.
LC-MS: $t_R$=1.11 min; [M+H]$^+$: 501.44.

Example 35

4-(2-{[5-(3-Methoxy-propyl)-2-phenyl-thiazole-4-carbonyl]-amino}-acetyl)-piperazine-1-carboxylic acid butyl ester This compound was prepared using a method analogous to that of Example 22, step 22.1, Example 34 replacing intermediate 21.1. In addition, a purification by preparative TLC (CH$_2$Cl$_2$/MeOH 95:5) was carried out.
LC-MS: $t_R$=1.09 min; [M+H]$^+$: 503.54.

Example 36

4-{(S)-3-Methyl-2-[(2-phenyl-thiazole-4-carbonyl)-amino]-butyryl}-piperazine-1-carboxylic acid butyl ester This compound was prepared using a method analogous to that of Example 8, step 8.3, 4-((S)-2-amino-3-methyl-butyryl)-piperazine-1-carboxylic acid butyl ester (prepared as described in WO2008044217) replacing piperazine-1-carboxylic acid butyl ester, phenyl-1,3-thiazole-4-carboxylic acid replacing intermediate 8.2 and using CH$_2$Cl$_2$ instead of CH$_2$Cl$_2$/THF. The compound was however purified by CC (EtOAc/Hept 0:1 to EtOAc/Hept 1:0).
LC-MS: $t_R$=1.09 min; [M+H]$^+$: 473.25.

Example 37

4-{(S)-2-[(5-Bromo-2-phenyl-thiazole-4-carbonyl)-amino]-3-hydroxy-propionyl}-piperazine-1-carboxylic acid butyl ester

37.1. 4-(2-Amino-3-hydroxy-propionyl)-piperazine-1-carboxylic acid butyl ester hydrochloride To a solution of 4-((S)-2-tert-butoxycarbonylamino-3-hydroxy-propionyl)-piperazine-1-carboxylic acid butyl ester (1.79 g, as described in WO2008044217) in CH$_2$Cl$_2$ (22 mL) was added HCl (4M in dioxane, 8.3 mL) and the reaction mixture was stirred for 2 h at RT. The suspension was diluted with Et$_2$O (1000 mL) and the white cake was filtered, washed with Et$_2$O and dried at HV overnight. The crude (1.19 g) was used without purification.
LC-MS: $t_R$=0.63 min; [M+H]$^+$: 274.40.

37.2. 4-{(S)-2-[(5-Bromo-2-phenyl-thiazole-4-carbonyl)-amino]-3-hydroxy-propionyl}-piperazine-1-carboxylic acid butyl ester A solution of intermediate 14.1 (310 mg) in CH$_2$Cl$_2$ (20 mL) and DIPEA (0.43 mL) was treated with PyBOP (632 mg)

and the reaction mixture stirred for 10 min at RT. Then intermediate 37.1 (354 mg) was added and the mixture stirred for 3 h at RT. The mixture was evaporated to dryness and directly purified by CC (EtOAc/Hept 6:4) to give 400 mg of the desired product.

LC-MS: $t_R$=1.02 min; [M+H]$^+$: 538.99.

Example 38

4-{(S)-3-Hydroxy-2-[(2-phenyl-thiazole-4-carbonyl)-amino]-propionyl}-piperazine-1-carboxylic acid butyl ester This compound was prepared using a method analogous to that of Example 37, 2-phenyl-1,3-thiazole-4-carboxylic acid replacing intermediate 14.1 and using preparative HPLC (III) instead of CC.

LC-MS: $t_R$=0.92 min; [M+H]$^+$: 461.01.

Example 39

4-((S)-2-{[5-((E)-2-Carboxy-vinyl)-2-phenyl-thiazole-4-carbonyl]-amino}-3-hydroxy-propionyl)-piperazine-1-carboxylic acid butyl ester Example 39

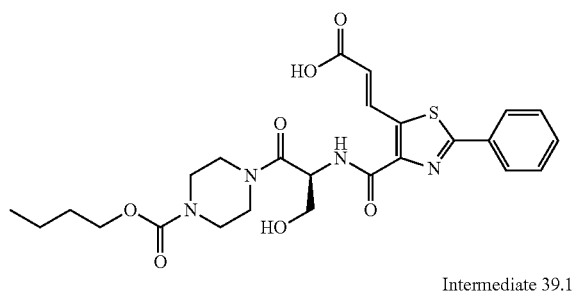

Intermediate 39.1

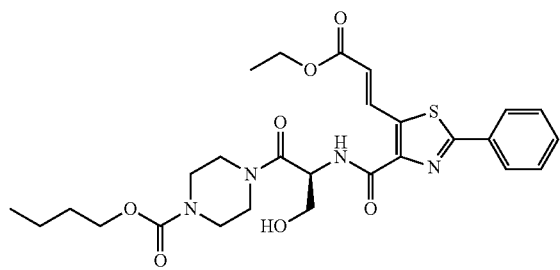

To a mixture of intermediate 37.2 (295 mg), ethoxycarbonylvinylboronic acid pinacol ester (148 mg) and [Pd(PPh$_3$)$_4$] (32 mg) was added aq. K$_2$CO$_3$ (2M, 0.38 mL) and DME (3 mL) and the reaction mixture stirred overnight at 90° C. The mixture was evaporated to dryness and directly purified by CC (EtOAc/Hept 1:1, then EtOAc, 1% HOAc) to give two fractions: The first eluting fraction gave after evaporation 196 mg of a yellow solid. This corresponded to the desired ethyl ester (Intermediate 39.1). A second eluting fraction was repurified by preparative TLC(CH$_2$Cl$_2$/MeOH 9:1) to give 9 mg of the desired acid (Example 39).

LC-MS: $t_R$=1.09 min; [M+H]$^+$: 559.44 (ester).
LC-MS: $t_R$=0.92 min; [M+H]$^+$: 531.03 (acid).

Example 40

4-((S)-2-{[5-(2-Carboxy-ethyl)-2-phenyl-thiazole-4-carbonyl]-amino}-3-hydroxy-propionyl)-piperazine-1-carboxylic acid butyl ester This compound was prepared using a method analogous to that of Example 16, step 16.4, intermediate 39.1 replacing intermediate 16.3. In addition, a preparative HPLC (III) was carried out.

LC-MS: $t_R$=0.94 min; [M+H]$^+$: 533.73.

Example 41

4-((R)-2-{[2-(4-Fluoro-phenyl)-thiazole-4-carbonyl]-amino}-3-phosphono-propionyl)-piperazine-1-carboxylic acid butyl ester 41.1. 4-[(R)-2-[(2-Bromo-thiazole-4-carbonyl)-amino]-3-(diethoxy-phosphoryl)-propionyl]-piperazine-1-carboxylic acid butyl ester This compound was prepared using a method analogous to that of Example 8, step 8.5, 2-bromo-4-thiazolecarboxylic acid replacing 2-phenyl-1,3-thiazole-4-carboxylic acid.

LC-MS: $t_R$=0.93 min; [M+H]$^+$: 583.43.

41.2. 4-((R)-3-(Diethoxy-phosphoryl)-2-{[2-(4-fluoro-phenyl)-thiazole-4-carbonyl]-amino}-propionyl)-piperazine-1-carboxylic acid butyl ester To a mixture of intermediate 41.1 (117 mg) in CH$_3$CN (1.1 mL) was added 4-fluorobenzeneboronic acid (29 mg) and PdCl$_2$(PPh$_3$)$_2$ (8.3 mg) followed by aq. Na$_2$CO$_3$ (1N, 1.1 mL). After stirring the reaction mixture at 85° C. overnight, 4-fluorobenzeneboronic acid (3.1 mg) and PdCl$_2$(PPh$_3$)$_2$ (1.5 mg) were added again the reaction mixture stirred for additional 24 h. After evaporation, the residue was extracted with EtOAc (3×) and the combined org. layers were evaporated to dryness. Purification by CC(CH$_2$Cl$_2$/MeOH 97:3 to 95:5) gave 77 mg of the desired product.

LC-MS: $t_R$=1.01 min; [M+H]$^+$: 599.86.

41.3. 4-((R)-2-{[2-(4-Fluoro-phenyl)-thiazole-4-carbonyl]-amino}-3-phosphono-propionyl)-piperazine-1-carboxylic acid butyl ester This compound was prepared using a method analogous to that of Example 9, intermediate 41.2 replacing intermediate 8.5. However, the reaction mixture was stirred first 1 h at 0° C., then 2 h at RT and the crude was purified by preparative HPLC (III) instead of (I).

LC-MS: $t_R$=0.86 min; [M+H]$^+$: 542.82.

Example 42

4-{(R)-3-(Diethoxy-phosphoryl)-2-[(2,5-diphenyl-thiazole-4-carbonyl)-amino]-propionyl}-piperazine-1-carboxylic acid butyl ester 42.1. 4-[(R)-2-[(5-Bromo-2-phenyl-thiazole-4-carbonyl)-amino]-3-(diethoxy-phosphoryl)-propionyl]-piperazine-1-carboxylic acid butyl ester This compound was prepared using a method analogous to that of Example 8, step 8.5, intermediate 14.1 replacing 2-phenyl-1,3-thiazole-4-carboxylic acid.

LC-MS: $t_R$=1.06 min; [M+H]$^+$: 658.95.

42.2. 4-{(R)-3-(Diethoxy-phosphoryl)-2-[(2,5-diphenyl-thiazole-4-carbonyl)-amino]-propionyl}-piperazine-1-carboxylic acid butyl ester A mixture of intermediate 42.1 (122 mg), phenylboronic acid (34 mg), [Pd(PPh$_3$)$_4$] (11 mg), CH$_3$CN (1.0 mL) and aq. Na$_2$CO$_3$ (1N, 1 mL) was heated at 80° C. for 2.5 h. The org. solvent was evaporated and the residue diluted with H$_2$O and extracted with EtOAc (3×). The org. phase was dried over MgSO$_4$, and evaporated. CC (EtOAc/Hept 1:1 to 1:0) gave 121 mg of the desired product.
LC-MS: $t_R$=1.11 min; [M+H]$^+$: 656.80.

Example 43

4-{(R)-2-[(2,5-Diphenyl-thiazole-4-carbonyl)-amino]-3-phosphono-propionyl}-piperazine-1-carboxylic acid butyl ester This compound was prepared using a method analogous to that of Example 9, intermediate 42.2 replacing intermediate 8.5. Purification with preparative HPLC (III) instead of (I) gave the desired compound.
LC-MS: $t_R$=0.96 min; [M+H]$^+$: 601.13.

Example 44

4-((R)-3-(Diethoxy-phosphoryl)-2-{[5-(4-methyl-piperazin-1-yl)-2-phenyl-thiazole-4-carbonyl]-amino}-propionyl)-piperazine-1-carboxylic acid butyl ester A mixture of intermediate 42.1 (100 mg), N-methylmorpholine (1.5 mL) and Cs$_2$CO$_3$ (67 mg) was heated at 70° C. until reaction completion. The reaction mixture was diluted with sat. aq. Na$_2$CO$_3$ and extracted with EtOAc. The combined org. phases were dried over MgSO$_4$ and evaporated. Purification by CC (Hept to Hept/EtOAc 8:2) gave 42 mg of the desired product.
LC-MS: $t_R$=0.84 min; [M+H]$^+$: 679.79.

Example 45

4-((R)-2-{[5-(4-Methyl-piperazin-1-yl)-2-phenyl-thiazole-4-carbonyl]-amino}-3-phosphono-propionyl)-piperazine-1-carboxylic acid butyl ester; hydrochloride This compound was prepared using a method analogous to that of Example 9, Example 44 replacing intermediate 8.5. Purification with preparative HPLC (III) instead of (I) gave the desired compound. The residue was taken up in HCl (4M in dioxane) and evaporated to dryness to give the corresponding HCl salt.
LC-MS: $t_R$=0.75 min; [M+H]$^+$: 622.86.

Example 46

4-[(R)-2-{[5-(Butyl-methyl-amino)-2-phenyl-thiazole-4-carbonyl]-amino}-3-(diethoxy-phosphoryl)-propionyl]-piperazine-1-carboxylic acid butyl ester This compound was prepared using a method analogous to that of Example 44, methylbutylamine replacing N-methylmorpholine. Purification by preparative HPLC (I) instead of CC gave the desired product.
LC-MS: $t_R$=1.12 min; [M+H]$^+$: 666.83.

Example 47

4-((R)-2-{[5-(Butyl-methyl-amino)-2-phenyl-thiazole-4-carbonyl]-amino}-3-phosphono-propionyl)-piperazine-1-carboxylic acid butyl ester This compound was prepared using a method analogous to that of Example 9, Example 46 replacing intermediate 8.5. Purification with preparative HPLC (III) instead of (I) gave the desired compound.
LC-MS: $t_R$=0.98 min; [M+H]$^+$: 610.65.

Example 48

4-{(R)-2-[(5-Bromo-4-phenyl-thiazole-2-carbonyl)-amino]-3-phosphono-propionyl}-piperazine-1-carboxylic acid butyl ester 48.1. 4-Phenyl-thiazole-2-carboxylic acid ethyl ester A solution of ethyl thiooxamate (1.30 g) and phenacylbromide (1.94 g) in dioxane (25 mL) was heated to reflux for 1 h. The reaction mixture was evaporated, diluted with H$_2$O, and the aq. phase extracted with 3×CH$_2$Cl$_2$ and washed with 2× aq. sat. NaHCO$_3$. The combined org. layers were dried over MgSO$_4$, filtrated off, evaporated and dried at HV. Purification by CC (Hept/EtOAc 9:1 to 1:1) gave 802 mg of the desired product.
LC-MS: $t_R$=1.06 min; [M+H]$^+$: 234.55.

48.2. 5-Bromo-4-phenyl-thiazole-2-carboxylic acid ethyl ester

To a solution of intermediate 48.1 (982 mg) in AcOH (20 mL) was added NBS (1577 mg) at RT. The resulting suspension was heated to 65° C. for 23 h30. The reaction mixture was evaporated and diluted with H$_2$O. The aq. phase was extracted with EtOAc (3×) and washed with aq. sat. NaHCO$_3$ and brine. The combined org. layers were dried over MgSO$_4$, filtrated off, evaporated and dried at HV. The crude was triturated with diethyl ether and filtrated off, washed with diethyl ether, evaporated and dried at HV. CC (Hept/EtOAc 95:5 to 7:3) followed by additional triturations with Hept gave 512 mg of the desired product.
LC-MS: $t_R$=1.19 min; [M+H]$^+$: 311.96.

48.3. 5-Bromo-4-phenyl-thiazole-2-carboxylic acid

To a solution of intermediate 48.2 (200 mg) in MeOH (10 mL) was added aq. KOH (1M, 1.9 mL), and the reaction mixture was stirred at 60° C. for 15 min. The reaction mixture was evaporated and the residue diluted with water and acidified (pH 2) with aq. HCl (1M, 2 mL) under ice-bath cooling. The resulting precipitate was filtrated off, washed with water and dried at HV to give 119 mg of the desired product.
LC-MS: $t_R$=0.96 min; [M+H]$^+$: 284.10.

48.4. 4-[(R)-2-[(5-Bromo-4-phenyl-thiazole-2-carbonyl)-amino]-3-(diethoxy-phosphoryl)-propionyl]-piperazine-1-carboxylic acid butyl ester This compound was prepared using a method analogous to that of Example 8, step 8.5, intermediate 48.3 replacing 5-bromo-4-phenyl-thiazole-2-carboxylic acid.
LC-MS: $t_R$=1.14 min; [M+H]$^+$: 658.82.

48.5. 4-{(R)-2-[(5-Bromo-4-phenyl-thiazole-2-carbonyl)-amino]-3-phosphono-propionyl}-piperazine-1-carboxylic acid butyl ester This compound was prepared using a method analogous to that of Example 9, intermediate 48.4 replacing intermediate 8.5. Purification with preparative HPLC (III) instead of (I) gave the desired compound.

LC-MS: $t_R$=0.96 min; $[M+H]^+$: 602.70.

Example 49

4-{(R)-2-[(4,5-Diphenyl-thiazole-2-carbonyl)-amino]-3-phosphono-propionyl}-piperazine-1-carboxylic acid butyl ester This compound was prepared using a method analogous to that of Example 9, Example 48 replacing intermediate 8.5. Purification with preparative HPLC (III) instead of (I) gave the desired compound.

LC-MS: $t_R$=1.01 min; $[M+H]^+$: 600.89.

Example 50

4-{2-[(4,5-Diphenyl-thiazole-2-carbonyl)-amino]-acetyl}-piperazine-1-carboxylic acid butyl ester

50.1. 4-{2-[(5-Bromo-4-phenyl-thiazole-2-carbonyl)-amino]-acetyl}-piperazine-1-carboxylic acid butyl ester This compound was prepared using a method analogous to that of Example 8, step 8.5, intermediate 48.3 replacing 5-bromo-4-phenyl-thiazole-2-carboxylic acid and intermediate 26.2 replacing intermediate 8.4.

LC-MS: $t_R$=1.15 min; $[M+H]^+$: 509.01.

50.2. 4-{2-[(4,5-Diphenyl-thiazole-2-carbonyl)-amino]acetyl}-piperazine-1-carboxylic acid butyl ester This compound was prepared using a method analogous to that of Example 42, step 42.2, intermediate 50.1 replacing intermediate 42.1. Purification with preparative HPLC (III) instead of CC gave the desired compound.

LC-MS: $t_R$=1.20 min; $[M+H]^+$: 507.53.

Example 51

4-(2-{[5-((E)-3-Methoxy-propenyl)-4-phenyl-thiazole-2-carbonyl]-amino}-acetyl)-piperazine-1-carboxylic acid butyl ester To a solution of intermediate 50.1 (100 mg) in EtOH/toluene (2 mL, 1:1) was added (E)-2-(3-methoxy-1-propen-1-yl)-4,4,5,5-tetramethyl-1,3,2-dioxaborolane (41 mg) followed by [Pd(PPh$_3$)$_4$] (11 mg) and a solution of K$_2$CO$_3$ (41 mg) in H$_2$O (0.5 mL) at RT. The reaction mixture was stirred for 2 h15 at 80° C. under argon and evaporated to dryness. Purification by preparative HPLC (III) gave 44 mg of the desired product LC-MS: $t_R$=1.11 min; $[M+H]^+$: 501.08.

Example 52

4-(2-{[5-(3-Methoxy-propyl)-4-phenyl-thiazole-2-carbonyl]-amino}-acetyl)-piperazine-1-carboxylic acid butyl ester This compound was prepared using a method analogous to that of Example 20, Example 51 replacing Example 19. No preparative HPLC was carried out.

LC-MS: $t_R$=1.11 min; $[M+H]^+$: 503.70.

Example 53

4-(2-{[5-((E)-2-Ethoxycarbonyl-vinyl)-4-phenyl-thiazole-2-carbonyl]-amino}-acetyl)-piperazine-1-carboxylic acid butyl ester This compound was prepared using a method analogous to that of Example 51, 2-ethoxycarbonylvinylboronic acid pinacol ester replacing (E)-2-(3-methoxy-1-propen-1-yl)-4,4,5,5-tetramethyl-1,3,2-dioxaborolane.

LC-MS: $t_R$=1.16 min; $[M+H]^+$: 529.53.

Example 54

4-(2-{[5-(2-Methoxycarbonyl-ethyl)-4-phenyl-thiazole-2-carbonyl]-amino}-acetyl)-piperazine-1-carboxylic acid butyl ester This compound was prepared using a method analogous to that of Example 52, Example 53 replacing Example 51. In addition, the crude was dissolved in MeOH (ca 0.1 mM) and stirred at 50° C. for 30 min. The reaction mixture was evaporated to dryness to give the desired product.

LC-MS: $t_R$=1.07 min; $[M+H]^+$: 517.46.

Example 55

4-(2-{[5-(2-Carboxy-ethyl)-4-phenyl-thiazole-2-carbonyl]-amino}-acetyl)-piperazine-1-carboxylic acid butyl ester To a solution of Example 54 (59 mg) in MeOH (3 mL) was added aq. NaOH (1M, 2 mL) and the reaction mixture stirred at RT for 1 h25. The reaction mixture was diluted with H$_2$O and extracted with 3× EtOAc. The combined org layers were dried over MgSO$_4$, and concentrated to dryness. Purification by preparative TLC (CH$_2$Cl$_2$/MeOH 7:3) gave 13 mg of the desired product.

LC-MS: $t_R$=0.98 min; $[M+H]^+$: 503.31.

Example 56

4-{(S)-2-[(5-Bromo-4-phenyl-thiazole-2-carbonyl)-amino]-4-carboxy-butyryl}-piperazine-1-carboxylic acid butyl ester

56.1. 4-{(S)-2-[(5-Bromo-4-phenyl-thiazole-2-carbonyl)-amino]-4-tert-butoxycarbonyl-butyryl}-piperazine-1-carboxylic acid butyl ester This compound was prepared using a method analogous to that of Example 8, step 8.5, intermediate 48.3 replacing 5-bromo-4-phenyl-thiazole-2-carboxylic acid and (S)-4-(2-amino-4-tert-butoxycarbonyl-butyryl)-piperazine-1-carboxylic acid butyl ester replacing intermediate 8.4.

LC-MS: $t_R$=1.33 min; $[M+H]^+$: 638.75.

56.2. 4-{(S)-2-[(5-Bromo-4-phenyl-thiazole-2-carbonyl)-amino]-4-carboxy-butyryl}-piperazine-1-carboxylic acid butyl ester This compound was prepared using a method analogous to that of Example 15, intermediate 56.1 replacing Example 15. Purification by preparative HPLC (III) instead of (I) gave the desired product.

LC-MS: $t_R$=1.10 min; $[M+H]^+$: 581.15.

Example 57

4-{(R)-3-[Bis-(acetoxymethoxy)-phosphoryl]-2-[(2-phenyl-thiazole-4-carbonyl)-amino]-propionyl}-piperazine-1-carboxylic acid butyl ester A solution of Example 9 (145 mg) in anh. NMP (0.8 mL) and NEt$_3$ (0.15 mL) was stirred for 20 min at RT. Then, bromomethyl acetate (0.3 mL) followed by NaI (50 mg) was added and the reaction mixture stirred at 45° C. overnight. The reaction mixture was diluted with toluene and washed with H$_2$O (5×). The organic phase was dried over MgSO$_4$ and evaporated to dryness. Purification by CC (EtOAc/Hept 0:1 to 1:0, then EtOAc/MeOH 9:1) gave 54 mg of the desired product.

LC-MS: $t_R$=1.00 min; $[M+H]^+$: 669.38.

Example 58

N,N'-Bis-((S)-1-Ethoxycarbonylethyl)-(R)-2-[(2-phenyl-thiazole-4-carbonyl)-amino]-3-oxo-3-(4-butoxy-carbonyl-piperazin-1-yl)-propyl-phosphonic acid diamide A mixture of Example 9 (100 mg), L-alanine ethyl ester hydrochloride (88 mg), NEt$_3$ (0.159 mL) in anh. pyridine (0.57 mL) was heated to 60° C. for 10 min. A freshly prepared yellow solution of 2,2'-dipyridyl disulfide (147 mg) and triphenylphosphine (175 mg) in anh. pyridine (0.57 mL) was added to the above mixture. The reaction mixture was stirred at 60° C. overnight, cooled to RT and concentrated. The residue was partitioned between CH$_2$Cl$_2$ and sat. aq. NaHCO$_3$. The organic phase was washed with brine, dried over Na$_2$SO$_4$ and evaporated to dryness. The crude was purified by CC(CH$_2$Cl$_2$/MeOH 0:1 to 94:6) gave 23 mg of the desired product.

LC-MS: $t_R$=1.00 min; $[M+H]^+$: 723.02.

Example 59

4-{(R)-3-[Bis-(ethoxycarbonyloxymethoxy)-phosphoryl]-2-[(2-phenyl-thiazole-4-carbonyl)-amino]-propionyl}-piperazine-1-carboxylic acid butyl ester A solution of Example 9 (100 mg) and NEt$_3$ (0.08 mL) in DMPU (0.35 mL) was stirred for 10 min at RT. Then, NaI (35 mg) and carbonic acid chloromethyl ester ethyl ester (0.76 mg, prepared as described in WO2004092189) were added. The mixture was stirred overnight at 50° C. under argon. The reaction mixture was washed with H$_2$O and the aq. phase extracted with toluene (3×). The combined org. phases were dried over Na$_2$SO$_4$ and concentrated to dryness. CC purification (EA/[CH$_2$Cl$_2$/MeOH 8:2] 1:0 to 3:1) gave 55 mg of the desired product.

LC-MS: $t_R$=1.07 min; $[M+H]^+$: 729.28.

Example 60

4-(2-{[5-(Hexyl-methyl-amino)-4-phenyl-thiazole-2-carbonyl]-amino}-acetyl)-piperazine-1-carboxylic acid butyl ester To a solution of intermediate 50.1 (76 mg) in N-hexylmethylamine (0.5 mL) was added Cs$_2$CO$_3$ (58 mg) at RT and the reaction mixture was stirred at 130° C. for 4 d. The reaction mixture was diluted with EtOAc (3×) and washed with aq. sat. Na$_2$CO$_3$, H$_2$O and brine. The combined org. layers were dried over MgSO4 and evaporated to dryness. Preparative HPLC (IX) to give 4 mg of the desired product.

LC-MS: $t_R$=1.35 min; $[M+H]^+$: 544.68.

Example 61

4-(2-{[5-(2-Carboxy-ethylamino)-2-phenyl-thiazole-4-carbonyl]-amino}-acetyl)-piperazine-1-carboxylic acid butyl ester To a suspension of Example 27 (25 mg) in H$_2$O/CH$_3$CN (0.2 mL, 1:1) was added at 0° C. diacetoxyiodobenzene (35 mg) and 2,2,6,6-tetramethylpiperidine-1-oxyl (3 mg), and the reaction mixture was stirred at 0° C. for 2 h. The reaction mixture was diluted with H$_2$O, acidified with aq. HCl (1M, 0.5 mL) and extracted with EtOAc (3×5 mL) The combined organic layers were dried over Na$_2$SO$_4$ and concentrated to dryness. Purification by CC (CH$_2$Cl$_2$/MeOH 97:3) gave 8 mg of the desired product.

LC-MS: $t_R$=0.59 min; $[M+H]^+$: 518.26.

Example 62

4-(2-{[5-(2-Ethoxycarbonyl-ethylamino)-2-phenyl-thiazole-4-carbonyl]-amino}-acetyl)-piperazine-1-carboxylic acid butyl ester To a solution of Example 61 (6 mg) in EtOH (0.2 mL) was added concentrated H$_2$SO$_4$ (20 μL), and the reaction mixture was stirred at RT for 1 h. The reaction mixture was diluted with H$_2$O and extracted with EtOAc (2×). The combined org. layers were dried over Na$_2$SO$_4$ and concentrated to dryness. Purification by CC(CH$_2$Cl$_2$/MeOH 97:3) gave 3 mg of the desired product.

LC-MS: $t_R$=1.11 min; $[M+H]^+$: 546.61.

Biological Tests

P2Y$_{12}$ Receptor Binding Assay

Procedure

Chinese Hamster Ovary (CHO) cells with recombinant expression of the human P2Y$_{12}$ receptor were cultured in 24 well cell-culture plates. Cells were washed three times with binding buffer (50 mM Tris pH 7.4, 100 mM NaCl, 1 mM EDTA, 0.5% BSA). The cells were then incubated with 0.5 ml per well binding buffer containing tritium-labeled 2-methyl-thio-adenosine 5'-diphosphate (2-methyl-S-ADP) (between 100'000 and 300'000 dpm per well) and various concentrations of test compounds. After incubation at RT for 2 hours, cells were washed three times with binding buffer. Then, cells were solubilized by addition of 0.5 ml solubilization buffer (SDS, NaOH, EDTA). The content of each well was then transferred into beta-counter vials and 2.0 ml of Ultima Gold Scintillation liquid was added. After quantification of the cell-associated signal, extent of inhibition was calculated relative to maximal possible inhibition demonstrated by addition of excess of cold 2-methyl-S-ADP.

Results Obtained for the Compounds of Formula I

The following results could be obtained for the Example compounds of formula I using the procedure described above for the P2Y$_{12}$ receptor binding assay:

| Example No. | IC$_{50}$ at P2Y$_{12}$ receptor binding assay (nM) |
| --- | --- |
| 1 | 9150 |
| 2 | 246 |
| 3 | 1470 |
| 4 | 249 |
| 5 | 464 |
| 6 | 334 |
| 7 | 16 |
| 8 | 502 |
| 9 | 2 |
| 10 | 635 |
| 11 | 1 |
| 12 | 4936 |
| 13 | 2 |
| 14 | 1224 |
| 15 | 41 |
| 16 | 7 |
| 17 | 43 |
| 18 | 11 |
| 19 | 6 |
| 20 | 13 |
| 21 | 19 |
| 22 | 28 |
| 23 | 39 |
| 24 | 7 |
| 25 | 3 |
| 26 | 94 |
| 27 | 34 |
| 28 | 47 |
| 29 | 525 |
| 30 | 268 |
| 31 | 19 |
| 32 | 157 |
| 33 | 31 |
| 34 | 85 |
| 35 | 99 |
| 36 | 104 |
| 37 | 696 |
| 38 | 71 |
| 39 | 35 |
| 40 | 43 |
| 41 | 6 |
| 42 | 2191 |
| 43 | 13 |
| 44 | 4179 |
| 45 | 3 |
| 46 | 821 |
| 47 | 3 |
| 48 | 6 |
| 49 | 152 |
| 50 | 1162 |
| 51 | 380 |
| 52 | 743 |
| 53 | 513 |
| 54 | 547 |
| 55 | 314 |
| 56 | 45 |
| 57 | 5 |
| 58 | 1218 |
| 59 | 15 |
| 60 | 1558 |
| 61 | 71 |
| 62 | 134 |

Compounds of formula I, wherein Z represents —P(O)(OR$^6$)$_2$, —P(O)(NHR$^7$)$_2$ or phenyl, wherein the phenyl is substituted with —P(O)(OR$^8$)$_2$, may be cleaved under aqueous or physiological conditions to the respective compounds of formula I, wherein Z represents —P(O)(OH)$_2$ or phenyl, wherein the phenyl is substituted with —P(O)(OH)$_2$.

The invention claimed is:
1. A compound of formula I

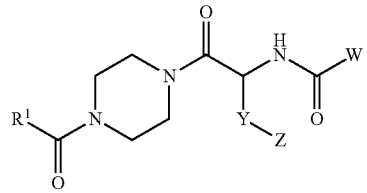

wherein
R$^1$ represents (C$_1$-C$_6$)alkoxy;
Y represents a bond and Z represents hydrogen; or
Y represents (C$_1$-C$_3$)alkandiyl and Z represents hydrogen, hydroxy, —COOH, —COOR$^5$, —P(O)(OH)$_2$, —P(O)(OR$^6$)$_2$, —P(O)(NHR$^7$)$_2$ or phenyl, wherein the phenyl is substituted with —P(O)(OH)$_2$ or —P(O)(OR$^8$)$_2$;
W represents a group selected from

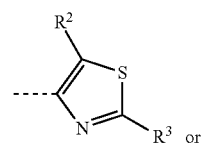

(G1)

or

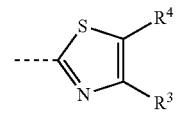

(G2)

R$^2$ represents hydrogen; halogen; (C$_1$-C$_4$)alkyl which is monosubstituted with (C$_1$-C$_4$)alkoxy, —COOH or —COOR$^9$; (C$_2$-C$_4$)alkenyl which is monosubstituted with (C$_1$-C$_4$)alkoxy, —COOH or —COOR$^9$; phenyl which is unsubstituted or monosubstituted with halogen; (C$_1$-C$_4$)alkyl-amino, wherein the alkyl-group is monosubstituted with hydroxy, (C$_1$-C$_4$)alkoxy, —COOH or —COOR$^9$; di-(C$_1$-C$_4$)alkyl-amino; heterocyclyl which is unsubstituted or monosubstituted with (C$_1$-C$_4$)alkyl or (C$_1$-C$_4$)alkoxy; or 2-methoxymethyl-cycloprop-1-yl;
R$^3$ represents aryl which is unsubstituted or mono- or di-substituted, wherein the substituents are independently selected from the group consisting of halogen, (C$_1$-C$_4$)alkyl, (C$_1$-C$_4$)alkoxy and phenoxy;
R$^4$ represents halogen; (C$_1$-C$_4$)alkyl which is monosubstituted with (C$_1$-C$_4$)alkoxy, —COOH, or —COOR$^9$; (C$_2$-C$_4$)alkenyl which is monosubstituted with (C$_1$-C$_4$)alkoxy or —COOR$^9$; phenyl; or di-(C$_1$-C$_6$)alkyl-amino;
R$^5$ represents (C$_1$-C$_4$)alkyl;
R$^6$ represents (C$_1$-C$_4$)alkyl, (C$_1$-C$_4$)alkyl-C(O)—OCH$_2$— or (C$_1$-C$_4$)alkoxy-C(O)—OCH$_2$—;
R$^7$ represents (C$_1$-C$_4$)alkoxy-C(O)—(C$_1$-C$_4$)alkyl-;
R$^8$ represents (C$_1$-C$_4$)alkyl;
R$^9$ represents (C$_1$-C$_4$)alkyl;
or a pharmaceutically acceptable salt of such a compound.
2. The compound of formula I according to claim 1, wherein
R$^1$ represents (C$_1$-C$_4$)alkoxy;
Y represents (C$_1$-C$_3$)alkandiyl and Z represents —P(O)(OH)$_2$, —P(O)(OR$^6$)$_2$, —P(O)(NHR$^7$)$_2$ or phenyl, wherein the phenyl is substituted with —P(O)(OH)$_2$ or —P(O)(OR$^8$)$_2$;

W represents a group selected from G1 or G2;
R² represents hydrogen; phenyl; di-($C_1$-$C_4$)alkyl-amino; or heterocyclyl which is mono-substituted with ($C_1$-$C_4$)alkyl;
R³ represents aryl which is unsubstituted or mono-substituted with halogen;
R⁴ represents halogen or phenyl;
R⁶ represents ($C_1$-$C_4$)alkyl, ($C_1$-$C_4$)alkyl-C(O)—OCH₂— or ($C_1$-$C_4$)alkoxy-C(O)—OCH₂—;
R⁷ represents ($C_1$-$C_4$)alkoxy-C(O)—($C_1$-$C_4$)alkyl-;
R⁸ represents ($C_1$-$C_4$)alkyl;
or a pharmaceutically acceptable salt of such a compound.

3. The compound of formula I according to claim 2, wherein
W represents the group G1;
or a pharmaceutically acceptable salt of such a compound.

4. The compound of formula I according to claim 1, wherein
Y represents ($C_1$-$C_3$)alkandiyl and Z represents hydroxy or —COOH;
or a pharmaceutically acceptable salt of such a compound.

5. The compound of formula I according to claim 1, wherein
Y represents ($C_1$-$C_3$)alkandiyl and Z represents —P(O)(OH)₂, —P(O)(OR⁶)₂, —P(O)(NHR⁷)₂ or phenyl, wherein the phenyl is substituted with —P(O)(OH)₂ or —P(O)(OR⁸)₂;
or a pharmaceutically acceptable salt of such a compound.

6. The compound of formula I according to claim 1, wherein
Y represents ($C_1$-$C_3$)alkandiyl and Z represents —P(O)(OH)₂ or phenyl, wherein the phenyl is substituted with —P(O)(OH)₂;
or a pharmaceutically acceptable salt of such a compound.

7. The compound of formula I according to claim 1, wherein
W represents the group G1;
or a pharmaceutically acceptable salt of such a compound.

8. The compound of formula I according to claim 1, wherein
R² represents hydrogen; halogen; ($C_1$-$C_4$)alkyl which is monosubstituted with ($C_1$-$C_4$)alkoxy or —COOH; ($C_2$-$C_4$)alkenyl which is monosubstituted with ($C_1$-$C_4$)alkoxy or —COOH; phenyl; ($C_1$-$C_4$)alkyl-amino, wherein the alkyl-group is monosubstituted with hydroxy, ($C_1$-$C_4$)alkoxy or —COOH; di-($C_1$-$C_4$)alkyl-amino; heterocyclyl which is unsubstituted or monosubstituted with ($C_1$-$C_4$)alkyl or ($C_1$-$C_4$)alkoxy; or (1S,2S)-2-methoxymethyl-cycloprop-1-yl;
or a pharmaceutically acceptable salt of such a compound.

9. The compound of formula I according to claim 1, wherein
R² represents hydrogen; phenyl; or di-($C_1$-$C_4$)alkyl-amino;
or a pharmaceutically acceptable salt of such a compound.

10. The compound of formula I according to claim 1, wherein
R³ represents aryl which is unsubstituted or mono-substituted with halogen;
or a pharmaceutically acceptable salt of such a compound.

11. The compound of formula I according to claim 1, wherein
R⁴ represents halogen or phenyl;
or a pharmaceutically acceptable salt of such a compound.

12. The compound of formula I according to claim 1, which is selected from the group consisting of:

4-{2-[(2-Phenyl-thiazole-4-carbonyl)-amino]-acetyl}-piperazine-1-carboxylic acid ethyl ester;

4-{(S)-4-Carboxy-2-[(2-phenyl-thiazole-4-carbonyl)-amino]-butyryl}-piperazine-1-carboxylic acid ethyl ester;

4-((S)-4-Carboxy-2-{[2-(2-phenoxy-phenyl)-thiazole-4-carbonyl]-amino}-butyryl)-piperazine-1-carboxylic acid butyl ester;

4-((S)-4-Carboxy-2-{[2-(3-methoxy-phenyl)-thiazole-4-carbonyl]-amino}-butyryl)-piperazine-1-carboxylic acid butyl ester;

4-((S)-4-Carboxy-2-{[2-(2-methoxy-phenyl)-thiazole-4-carbonyl]-amino}-butyryl)-piperazine-1-carboxylic acid butyl ester;

4-{(S)-4-Carboxy-2-[(2-o-tolyl-thiazole-4-carbonyl)-amino]-butyryl}-piperazine-1-carboxylic acid butyl ester;

4-{(S)-4-Carboxy-2-[(2-phenyl-thiazole-4-carbonyl)-amino]-butyryl}-piperazine-1-carboxylic acid butyl ester;

4-{(R)-3-(Diethoxy-phosphoryl)-2-[(2-phenyl-thiazole-4-carbonyl)-amino]-propionyl}-piperazine-1-carboxylic acid butyl ester;

4-{(R)-2-[(2-Phenyl-thiazole-4-carbonyl)-amino]-3-phosphono-propionyl}-piperazine-1-carboxylic acid butyl ester;

4-{(S)-3-[4-(Diethoxy-phosphoryl)-phenyl]-2-[(2-phenyl-thiazole-4-carbonyl)-amino]-propionyl}-piperazine-1-carboxylic acid butyl ester;

4-[(S)-2-[(2-Phenyl-thiazole-4-carbonyl)-amino]-3-(4-phosphono-phenyl)-propionyl]-piperazine-1-carboxylic acid butyl ester;

4-{(S)-3-[4-(Diethoxy-phosphoryl)-phenyl]-2-[(2-phenyl-thiazole-4-carbonyl)-amino]-propionyl}-piperazine-1-carboxylic acid ethyl ester;

4-[(S)-2-[(2-Phenyl-thiazole-4-carbonyl)-amino]-3-(4-phosphono-phenyl)-propionyl]-piperazine-1-carboxylic acid ethyl ester;

4-{(S)-2-[(5-Bromo-2-phenyl-thiazole-4-carbonyl)-amino]-4-tert-butoxycarbonyl-butyryl}-piperazine-1-carboxylic acid butyl ester;

4-{(S)-2-[(5-Bromo-2-phenyl-thiazole-4-carbonyl)-amino]-4-carboxy-butyryl}-piperazine-1-carboxylic acid butyl ester;

4-{(S)-4-Carboxy-2-[(5-chloro-2-phenyl-thiazole-4-carbonyl)-amino]-butyryl}-piperazine-1-carboxylic acid butyl ester;

4-{(S)-4-Carboxy-2-[(2,5-diphenyl-thiazole-4-carbonyl)-amino]-butyryl}-piperazine-1-carboxylic acid butyl ester;

4-((S)-4-Carboxy-2-{[5-((1S,2S)-2-methoxymethyl-cyclopropyl)-2-phenyl-thiazole-4-carbonyl]-amino}-butyryl)-piperazine-1-carboxylic acid butyl ester;

4-((S)-4-Carboxy-2-{[5-((E)-2-carboxy-vinyl)-2-phenyl-thiazole-4-carbonyl]amino}-butyryl)-piperazine-1-carboxylic acid butyl ester;

4-((S)-4-Carboxy-2-{[5-(2-carboxy-ethyl)-2-phenyl-thiazole-4-carbonyl]-amino}-butyryl)-piperazine-1-carboxylic acid butyl ester;

4-((S)-4-Carboxy-2-{[5-((E)-3-methoxy-propenyl)-2-phenyl-thiazole-4-carbonyl]-amino}-butyryl)-piperazine-1-carboxylic acid butyl ester;

4-((S)-4-Carboxy-2-{[5-(3-methoxy-propyl)-2-phenyl-thiazole-4-carbonyl]-amino}-butyryl)-piperazine-1-carboxylic acid butyl ester;

4-{(S)-4-Carboxy-2-[(5-morpholin-4-yl-2-phenyl-thiazole-4-carbonyl)-amino]-butyryl}-piperazine-1-carboxylic acid butyl ester;
4-{(S)-4-Carboxy-2-[(2-phenyl-5-pyrrolidin-1-yl-thiazole-4-carbonyl)-amino]-butyryl}-piperazine-1-carboxylic acid butyl ester;
4-((S)-4-Carboxy-2-{[5-((S)-3-methoxy-pyrrolidin-1-yl)-2-phenyl-thiazole-4-carbonyl]-amino}-butyryl)-piperazine-1-carboxylic acid butyl ester;
4-{2-[(2-Phenyl-thiazole-4-carbonyl)-amino]-acetyl}-piperazine-1-carboxylic acid butyl ester;
4-(2-{[5-(3-Hydroxy-propylamino)-2-phenyl-thiazole-4-carbonyl]-amino}-acetyl)-piperazine-1-carboxylic acid butyl ester;
4-(2-{[5-(3-Methoxy-propylamino)-2-phenyl-thiazole-4-carbonyl]-amino}-acetyl)-piperazine-1-carboxylic acid butyl ester;
4-(2-{[5-(3-Fluoro-phenyl)-2-phenyl-thiazole-4-carbonyl]-amino}-acetyl)-piperazine-1-carboxylic acid butyl ester;
4-(2-{[5-((E)-2-Ethoxycarbonyl-vinyl)-2-phenyl-thiazole-4-carbonyl]amino}-acetyl)-piperazine-1-carboxylic acid butyl ester;
4-(2-{[5-((E)-2-Carboxy-vinyl)-2-phenyl-thiazole-4-carbonyl]-amino}-acetyl)-piperazine-1-carboxylic acid butyl ester;
4-(2-{[5-(2-Ethoxycarbonyl-ethyl)-2-phenyl-thiazole-4-carbonyl]-amino}-acetyl)-piperazine-1-carboxylic acid butyl ester;
4-(2-{[5-(2-Carboxy-ethyl)-2-phenyl-thiazole-4-carbonyl]-amino}-acetyl)-piperazine-1-carboxylic acid butyl ester;
4-(2-{[5-(3-Methoxy-propenyl)-2-phenyl-thiazole-4-carbonyl]-amino}-acetyl)-piperazine-1-carboxylic acid butyl ester;
4-(2-{[5-(3-Methoxy-propyl)-2-phenyl-thiazole-4-carbonyl]-amino}-acetyl)-piperazine-1-carboxylic acid butyl ester;
4-{(S)-3-Methyl-2-[(2-phenyl-thiazole-4-carbonyl)-amino]-butyryl}-piperazine-1-carboxylic acid butyl ester;
4-{(S)-2-[(5-Bromo-2-phenyl-thiazole-4-carbonyl)-amino]-3-hydroxy-propionyl}-piperazine-1-carboxylic acid butyl ester;
4-{(S)-3-Hydroxy-2-[(2-phenyl-thiazole-4-carbonyl)-amino]-propionyl}-piperazine-1-carboxylic acid butyl ester;
4-((S)-2-{[5-((E)-2-Carboxy-vinyl)-2-phenyl-thiazole-4-carbonyl]-amino}-3-hydroxy-propionyl)-piperazine-1-carboxylic acid butyl ester;
4-((S)-2-{[5-(2-Carboxy-ethyl)-2-phenyl-thiazole-4-carbonyl]amino}-3-hydroxy-propionyl)-piperazine-1-carboxylic acid butyl ester;
4-((R)-2-{[2-(4-Fluoro-phenyl)-thiazole-4-carbonyl]-amino}-3-phosphono-propionyl)-piperazine-1-carboxylic acid butyl ester;
4-{(R)-3-(Diethoxy-phosphoryl)-2-[(2,5-diphenyl-thiazole-4-carbonyl)-amino]-propionyl}-piperazine-1-carboxylic acid butyl ester;
4-{(R)-2-[(2,5-Diphenyl-thiazole-4-carbonyl)-amino]-3-phosphono-propionyl}-piperazine-1-carboxylic acid butyl ester;
4-((R)-3-(Diethoxy-phosphoryl)-2-{[5-(4-methyl-piperazin-1-yl)-2-phenyl-thiazole-4-carbonyl]-amino}-propionyl)-piperazine-1-carboxylic acid butyl ester;
4-((R)-2-{[5-(4-Methyl-piperazin-1-yl)-2-phenyl-thiazole-4-carbonyl]-amino}-3-phosphono-propionyl)-piperazine-1-carboxylic acid butyl ester;
4-[(R)-2-{[5-(Butyl-methyl-amino)-2-phenyl-thiazole-4-carbonyl]-amino}-3-(diethoxy-phosphoryl)-propionyl]-piperazine-1-carboxylic acid butyl ester;
4-((R)-2-{[5-(Butyl-methyl-amino)-2-phenyl-thiazole-4-carbonyl]-amino}-3-phosphono-propionyl)-piperazine-1-carboxylic acid butyl ester;
4-{(R)-2-[(5-Bromo-4-phenyl-thiazole-2-carbonyl)-amino]-3-phosphono-propionyl}-piperazine-1-carboxylic acid butyl ester;
4-{(R)-2-[(4,5-Diphenyl-thiazole-2-carbonyl)-amino]-3-phosphono-propionyl}-piperazine-1-carboxylic acid butyl ester;
4-{2-[(4,5-Diphenyl-thiazole-2-carbonyl)-amino]-acetyl}-piperazine-1-carboxylic acid butyl ester;
4-(2-{[5-((E)-3-Methoxy-propenyl)-4-phenyl-thiazole-2-carbonyl]amino}-acetyl)-piperazine-1-carboxylic acid butyl ester;
4-(2-{[5-(3-Methoxy-propyl)-4-phenyl-thiazole-2-carbonyl]-amino}-acetyl)-piperazine-1-carboxylic acid butyl ester;
4-(2-{[5-((E)-2-Ethoxycarbonyl-vinyl)-4-phenyl-thiazole-2-carbonyl]amino}-acetyl)-piperazine-1-carboxylic acid butyl ester;
4-(2-{[5-(2-Methoxycarbonyl-ethyl)-4-phenyl-thiazole-2-carbonyl]-amino}-acetyl)-piperazine-1-carboxylic acid butyl ester;
4-(2-{[5-(2-Carboxy-ethyl)-4-phenyl-thiazole-2-carbonyl]-amino}-acetyl)-piperazine-1-carboxylic acid butyl ester;
4-{(S)-2-[(5-Bromo-4-phenyl-thiazole-2-carbonyl)-amino]-4-carboxy-butyryl}-piperazine-1-carboxylic acid butyl ester;
4-{(R)-3-[Bis-(acetoxymethoxy)-phosphoryl]-2-[(2-phenyl-thiazole-4-carbonyl)-amino]propionyl}-piperazine-1-carboxylic acid butyl ester;
N,N'-Bis-((S)-1-Ethoxycarbonylethyl)-(R)-2-[(2-phenyl-thiazole-4-carbonyl)-amino]-3-oxo-3-(4-butoxy-carbonyl-piperazin-1-yl)-propyl-phosphonic acid diamide;
4-{(R)-3-[Bis-(ethoxycarbonyloxymethoxy)-phosphoryl]-2-[(2-phenyl-thiazole-4-carbonyl)-amino]-propionyl}-piperazine-1-carboxylic acid butyl ester;
4-(2-{[5-(Hexyl-methyl-amino)-4-phenyl-thiazole-2-carbonyl]-amino}-acetyl)-piperazine-1-carboxylic acid butyl ester;
4-(2-{[5-(2-Carboxy-ethylamino)-2-phenyl-thiazole-4-carbonyl]-amino}-acetyl)-piperazine-1-carboxylic acid butyl ester; and
4-(2-{[5-(2-Ethoxycarbonyl-ethylamino)-2-phenyl-thiazole-4-carbonyl]-amino}-acetyl)-piperazine-1-carboxylic acid butyl ester;
or a pharmaceutically acceptable salt of such a compound.

13. A pharmaceutical composition containing at least one compound of formula I as defined in claim 1, or a pharmaceutically acceptable salt thereof, and one or more pharmaceutically acceptable carriers, diluents or excipients.

14. A method for the treatment of myocardial infarction, arterial thrombosis, transient ischaemic attacks, peripheral vascular disease or stable or unstable angina, comprising the administration to a patient in need thereof of an effective amount of the compound of formula I according to claim 1, or a pharmaceutically acceptable salt of such a compound.

* * * * *

UNITED STATES PATENT AND TRADEMARK OFFICE
CERTIFICATE OF CORRECTION

PATENT NO.        : 8,664,203 B2
APPLICATION NO.   : 13/265493
DATED             : March 4, 2014
INVENTOR(S)       : Caroff et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 189 days.

Signed and Sealed this
Twenty-ninth Day of September, 2015

Michelle K. Lee
*Director of the United States Patent and Trademark Office*